United States Patent
Chen et al.

(10) Patent No.: US 11,453,705 B2
(45) Date of Patent: Sep. 27, 2022

(54) MULTIVALENT PARTICLES COMPOSITIONS AND METHODS OF USE

(71) Applicant: Achelois BioPharma, Inc., Redwood City, CA (US)

(72) Inventors: Chang-Zheng Chen, Palo Alto, CA (US); Guoqiang Dong, Union City, CA (US); Yiling Luo, South San Francisco, CA (US); Hua Zhou, San Mateo, CA (US); Tian-Qiang Sun, San Francisco, CA (US); Michael Chen, Palo Alto, CA (US)

(73) Assignee: ACHELOIS BIOPHARMA, INC., Redwood City, CA (US)

( * ) Notice: Subject to any disclaimer, the term of this patent is extended or adjusted under 35 U.S.C. 154(b) by 0 days.

(21) Appl. No.: 17/514,572

(22) Filed: Oct. 29, 2021

(65) Prior Publication Data

US 2022/0135626 A1  May 5, 2022

Related U.S. Application Data

(60) Provisional application No. 63/108,105, filed on Oct. 30, 2020, provisional application No. 63/191,245, filed on May 20, 2021.

(51) Int. Cl.
*C07K 14/165* (2006.01)
*C12N 9/48* (2006.01)

(52) U.S. Cl.
CPC ............ *C07K 14/165* (2013.01); *C12N 9/485* (2013.01); *C07K 2319/03* (2013.01); *C12Y 304/17023* (2013.01)

(58) Field of Classification Search
None
See application file for complete search history.

(56) References Cited

U.S. PATENT DOCUMENTS

| | | |
|---|---|---|
| 10,787,501 B1 | 9/2020 | Babb et al. |
| 2004/0082496 A1 | 4/2004 | Acton et al. |
| 2006/0257852 A1 | 11/2006 | Rappuoli et al. |
| 2009/0022762 A1 | 1/2009 | Galarza et al. |

OTHER PUBLICATIONS

PCT/US2021/057368 International Search Report and Written Opinion dated Mar. 28, 2022.
PCT/US2021/057368 Invitation to Pay Additional Fees dated Jan. 20, 2022.
Rao et al. Decoy nanoparticles protect against COVID-19 by concurrently adsorbing viruses and inflammatory cytokines. PNAS USA 117(44):27141-27147 (2020).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1997).
Chua et al. Hepatitis C VLPs Delivered to Dendritic Cells by a TLR2 Targeting Lipopeptide Results in Enhanced Antibody and Cell-Mediated Responses. PLoS One 7(10):e47492 (2012).
Cubas et al. Chimeric Trop2 virus-like particles: a potential immunotherapeutic approach against pancreatic cancer. J Immunother 34(3):251-63 (2011).
Garg et al. Virus Like Particles (VLP) as multivalent vaccine candidate against Chikungunya, Japanese Encephalitis, Yellow Fever and Zika Virus. Sci Rep 10(1):4017 (2020).
Gleiter et al. Cell-Type Specific Targeting and Gene Expression Using a Variant of Polyoma VP1 Virus-Like Particles. Biol Chem 384(2):247-55 (2003).
INAL. Decoy ACE2-expressing extracellular vesicles that competitively bind SARS-CoV-2 as a possible COVID-19 therapy. Clinical Science 134:301-1304 (2020).
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87:2264-2268 (1990).
Lévy et al. Surface engineering of lentiviral vectors for gene transfer into gene therapy target cells. Curr Opin Pharmacol 24:79-85 (2015).
Mohsen et al. Virus-like particles for vaccination against cancer. Wiley Interdiscip Rev Nanomed Nanobiotechnol 12(1):e1579 (2020).
Ong et al. Virus like particles as a platform for cancer vaccine development. PeerJ 5:e4053 (2017).
Rohovie et al. Virus-like particles: Next-generation nanoparticles for targeted therapeutic delivery. Bioeng Transl Med 2(1):43-57 (2017).
Roldao et al. Viruses and Virus-Like Particles in Biotechnology: Fundamentals and Applications. Comprehensive Biotechnology 2011:625 (2011).
Seow et al. Biological Gene Delivery Vehicles: Beyond Viral Vectors. Molecular Therapy 17(5):767-777 (2009).
Viral Receptor-Envelope Protein Pair Table (Sep. 19, 2020) (5 pgs).
Wootton et al. Statistics of local complexity in amino acid sequences and sequence databases. Computers & Chemistry 17(2):149-163 (Jun. 1993).

*Primary Examiner* — Suzanne M Noakes
*Assistant Examiner* — Jae W Lee
(74) *Attorney, Agent, or Firm* — Wilson Sonsini Goodrich & Rosati

(57) ABSTRACT

Provided herein are multivalent particles and compositions of multivalent particles for blocking viral infection.

16 Claims, 41 Drawing Sheets

Specification includes a Sequence Listing.

| Inhibitors | IC$_{50}$ [M] |
|---|---|
| 1 ◆ ACE2-VGTM MVPs | (2.32 ± 0.93) ×10$^{-13}$ |
| 2 ◆ RGN989 | (3.49 ± 2.13) ×10$^{-11}$ |
| 3 ◆ RGN933 | (6.00 ± 3.12) ×10$^{-11}$ |

FIG. 2D

| CoV-2 Spike Mutation | IC$_{50}$[pM] |
|---|---|
| 1 ◆ Wild type | 0.4 ± 0.3 |
| 2 ◆ D614G | 0.7 ± 0.3 |
| 3 ◆ N439K | 1.7 ± 1.7 |
| 4 ◆ N501Y | 0.43 ± 0.04 |
| 5 ◆ E484K | 1.7 ± 0.4 |
| 6 ◆ E484Q + L452R | 1.0 ± 1.1 |

| Inhibitor | IC₅₀ |
|---|---|
| 1 ◆ DPP4-MVP | 2.96 ± 1.33 pM |
| 2 ◆ Recombinant-DPP4 | >48 nM |
| □ Bald Particles | N.D. |

PVP spikes: MERS CoV
Target cells: H1650 cells

| Decoy-MVPs | IC₅₀ [fM] |
|---|---|
| 1 ◆ WT/ACE2-VGTM | 211 ± 93.7 |
| 2 ◆ H2A/ACE2-VGTM | 377 ± 79.4 |

PVP spikes: SAR CoV-2
Target cells: 293T/ACE2 cells

PVP spikes: SAR CoV-1
Target cells: VERO-E6 cells

| Decoy ACE2 MVP | | $IC_{50}$ [fM] |
|---|---|---|
| 1 | WT-ACE2-VGTM | 440 ± 139 |
| 2 | H2A-ACE2-VGTM | 890 ± 237 |
| 3 | WT-ACE2-D4VG | 204 ± 73.7 |
| 4 | H2A-ACE2-D4VG | 428 ± 87.6 |

FIG. 7B

| Particle Type | Mean Particle Diameter (nm) |
|---|---|
| ACE2-D4VG EV | 131 ± 29 |

FIG. 13A

| Antivirus | Display | IC$_{50}$[fM] |
|---|---|---|
| ACE2-D4VG EV | Trimeric | 26 ± 12 |

FIG. 13B

MULTIVALENT PARTICLES COMPOSITIONS AND METHODS OF USE

CROSS-REFERENCE

This application claims the benefit of U.S. Provisional Application No. 63/108,105 filed Oct. 30, 2020; and U.S. Provisional Application No. 63/191,245 filed May 20, 2021, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 25, 2021, is named 48295-701_201_SL.txt and is 107,373 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Disclosed herein, in certain embodiments, are multivalent particle comprising a fusion protein that comprises a mammalian polypeptide that binds to a viral protein and a transmembrane polypeptide wherein the fusion protein is expressed at least about 10 copies on a surface of the multivalent particle. In some embodiments, the viral protein is from SARS-CoV-1, SARS-CoV-2, MERS-CoV, Respiratory syncytial virus, HIV, or combinations thereof. In some embodiments, the mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the mammalian polypeptide comprises an extracellular domain of the receptor. In some embodiments, the mammalian polypeptide comprises a ligand or a secreted protein. In some embodiments, the mammalian polypeptide comprises ACE2, TRMPSS2, DPP4, CD4, CCR5, CXCR4, CD209, or CLEC4M. In some embodiments, the mammalian polypeptide comprises an amino acid sequence of at least 90% sequence identity to an amino acid sequence according to SEQ ID NO: 1. In some embodiments, the mammalian polypeptide comprises an amino acid sequence of at least 90% sequence identity to an amino acid sequence according to SEQ ID NO: 2.

In some embodiments, the transmembrane polypeptide anchors the fusion protein to a bilayer of the multivalent particle. In some embodiments, the transmembrane polypeptide comprises a spike glycoprotein transmembrane region, a mammalian membrane protein, an envelope protein, a nucleocapsid protein, or a cellular transmembrane protein. In some embodiments, the transmembrane polypeptide comprises a VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120. In some embodiments, the VSVG transmembrane region comprises full length VSVG transmembrane region or a truncated VSVG transmembrane region. In some embodiments, the transmembrane polypeptide comprises the VSVG transmembrane region and a VSVG cytoplasmic tail. In some embodiments, the transmembrane polypeptide comprises an amino acid sequence at least about 90% identical to that set forth in SEQ ID NO: 3 In some embodiments, the transmembrane polypeptide comprises an amino acid sequence at least about 90% identical to that set forth in SEQ ID NO: 4.

In some embodiments, the fusion protein is expressed at least about 50 copies on a surface of the multivalent particle. In some embodiments, the fusion protein is expressed at least about 75 copies on a surface of the multivalent particle. In some embodiments, the fusion protein is expressed at least about 100 copies on a surface of the multivalent particle. In some embodiments, the fusion protein is expressed at least about 150 copies on a surface of the multivalent particle. In some embodiments, the fusion protein is expressed at least about 200 copies on a surface of the multivalent particle.

In some embodiments, the mammalian polypeptide comprises ACE2 and the transmembrane polypeptide comprises a VSVG transmembrane region. In some embodiments, the mammalian polypeptide comprises ACE2 and the transmembrane polypeptide comprises a spike protein S2 transmembrane region. In some embodiments, the mammalian polypeptide comprises ACE2 and the transmembrane polypeptide comprises a surface glycoprotein transmembrane region of an enveloped virus. In some embodiments, the mammalian polypeptide comprises DPP4 and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the multivalent particle further comprises a second fusion protein that comprises a second mammalian polypeptide that binds to the viral protein and a second transmembrane polypeptide wherein the second fusion protein is expressed at least about 10 copies on the surface of the multivalent particle. In some embodiments, the second mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the second mammalian polypeptide comprises an extracellular domain of the receptor. In some embodiments, the second mammalian polypeptide comprises a ligand or a secreted protein. In some embodiments, the second mammalian polypeptide comprises ACE2, TRMPSS2, DPP4, CD4, CCR5, CXCR4, CD209, or CLEC4M.

In some embodiments, the second mammalian polypeptide comprises an amino acid sequence of at least 90% sequence identity to an amino acid sequence according to SEQ ID NO: 1. In some embodiments, the second mammalian polypeptide comprises an amino acid sequence of at least 90% sequence identity to an amino acid sequence according to SEQ ID NO: 2. In some embodiments, the second transmembrane polypeptide comprises a transmembrane anchoring protein. In some embodiments, the second transmembrane polypeptide comprises a spike glycoprotein transmembrane region, a mammalian membrane protein, an envelope protein, a nucleocapsid protein, or a cellular transmembrane protein. In some embodiments, the second transmembrane polypeptide comprises VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120. In some embodiments, the VSVG transmembrane region comprises full length VSVG transmembrane region or a truncated VSVG transmembrane region. In some embodiments, the transmembrane polypeptide comprises a VSVG transmembrane region and a VSVG cytoplasmic tail. In some embodiments, the second transmembrane polypeptide comprises an amino acid sequence at least about 90% identical to that set forth in SEQ ID NO: 3. In some embodiments, the second transmembrane polypeptide comprises an amino acid sequence at least about 90% identical to that set forth in SEQ ID NO: 4.

In some embodiments, the second fusion protein is expressed at least about 50 copies on a surface of the multivalent particle. In some embodiments, the second fusion protein is expressed at least about 75 copies on a surface of the multivalent particle. In some embodiments, the second fusion protein is expressed at least about 100 copies on a surface of the multivalent particle. In some embodiments, the second fusion protein is expressed at least about 150 copies on a surface of the multivalent particle. In some embodiments, the second fusion protein is expressed at least about 200 copies on a surface of the multivalent particle.

In some embodiments, the second mammalian polypeptide comprises ACE2 and the second transmembrane polypeptide comprises VSVG transmembrane region. In some embodiments, the second mammalian polypeptide comprises ACE2 and the second transmembrane polypeptide comprises spike protein S2 transmembrane region. In some embodiments, the second mammalian polypeptide comprises ACE2 and the second transmembrane polypeptide comprises a surface glycoprotein of an enveloped virus. In some embodiments, the second mammalian polypeptide comprises DPP4 and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the mammalian polypeptide comprises a viral entry receptor and the second mammalian polypeptide comprises a viral attachment receptor. In some embodiments, the mammalian polypeptide comprises ACE2, the transmembrane polypeptide comprises VSVG transmembrane region, spike protein S1 transmembrane region, spike protein S2 transmembrane region, or a surface glycoprotein of an enveloped virus, the second mammalian polypeptide comprises a heparan sulfate proteoglycan, and the second transmembrane polypeptide comprises VSVG transmembrane region, spike protein S1 transmembrane region, spike protein S2 transmembrane region, or a surface glycoprotein of an enveloped virus. In some embodiments, the mammalian polypeptide comprises CD4 and the second mammalian peptide comprises, CCR5, CXCR4, or both.

In some embodiments, the multivalent particle comprises an IC50 of less than 5 picomolar (pM) in a neutralization assay. In some embodiments, the multivalent particle comprises an IC50 of less than 2.5 picomolar (pM) in a neutralization assay. In some embodiments, the multivalent particle comprises an IC50 of less than 1 picomolar (pM) in a neutralization assay. In some embodiments, the multivalent particle does not comprise viral genetic material. In some embodiments, the multivalent particle is synthetic. In some embodiments, the multivalent particle is recombinant.

In some embodiments, the multivalent particle is a viral-like a particle. In some embodiments, the multivalent particle is an extracellular vesicle. In some embodiments, the multivalent particle is an exosome. In some embodiments, the multivalent particle is an ectosome. In some embodiments, the fusion protein further comprises an oligomerization domain. In some embodiments, in the oligomerization domain is a dimerization domain. In some embodiments, the dimerization domain comprises a leucine zipper dimerization domain. In some embodiments, the oligomerization domain is a trimerization domain. In some embodiments, the trimerization domain comprises a post-fusion oligomerization domain of viral surface protein. In some embodiments, the trimerization domain comprises a D4 post-fusion trimerization domain of VSV-G protein. In some embodiments, the trimerization domain comprises a Dengue E protein post-fusion trimerization domain. In some embodiments, the trimerization domain comprises a foldon trimerization domain. In some embodiments, the trimerization domain comprises human C-propeptide of α1(I) collagen. In some embodiments, the oligomerization domain is a tetramerization domain. In some embodiments, the tetramerization domain comprises an influenza neuraminidase stem domain.

In some embodiments, the oligomerization domain comprises an amino acid sequence that has at least 95% sequence identity to an amino acid sequence according to SEQ ID NOs: 5-18, or 28. In some embodiments, when the fusion protein is expressed on the surface of the multivalent particle, the oligomerization domain is outside of the multivalent particle. In some embodiments, when the fusion protein is expressed on the surface of the multivalent particle, the oligomerization domain is outside of the multivalent particle and adjacent to a signal peptide. In some embodiments, when the fusion protein is expressed on the surface of the multivalent particle, the oligomerization domain is inside of the multivalent particle. In some embodiments, when the fusion protein is expressed on the surface of the multivalent particle, the oligomerization domain is inside of the multivalent particle and adjacent to the transmembrane polypeptide. In some embodiments, the fusion protein comprises a signal peptide.

In some embodiments, domains of the fusion protein are arranged from the N-terminus to the C-terminus in the following orders:

(a) signal peptide, extracellular domain of a viral entry receptor which binds to a surface protein of a virus, oligomerization domain, transmembrane polypeptide, and cytosolic domain;

(b) signal peptide, extracellular domain of a viral entry receptor which binds to a surface protein of a virus, transmembrane polypeptide, oligomerization domain, and cytosolic domain; or (c) signal peptide, oligomerization domain, extracellular domain of a viral entry receptor, transmembrane polypeptide, and cytosolic domain.

Disclosed herein, in certain embodiments are compositions comprising a first nucleic acid sequence encoding a multivalent particle comprising a fusion protein that comprises an extracellular domain of a viral entry receptor that binds to a viral protein and a transmembrane polypeptide wherein the fusion protein is expressed at least about 10 copies on a surface of the multivalent particle when the multivalent particle is expressed; and an excipient. In some embodiments, the viral protein is from SARS-CoV-1, SARS-CoV-2, MERS-CoV, Respiratory syncytial virus, HIV, or combinations thereof. In some embodiments, the composition further comprises a second nucleic acid sequence that encodes one or more packaging viral proteins. In some embodiments, the one or more packaging viral proteins is a lentiviral protein, a retroviral protein, an adenoviral protein, or combinations thereof. In some embodiments, the one or more packaging viral proteins comprises gag, pol, pre, tat, rev, or combinations thereof. In some embodiments, the composition further comprises a third nucleic acid sequence that encodes a replication incompetent viral genome, a reporter, a therapeutic molecule, or combinations thereof.

In some embodiments, the viral genome is derived from vesicular stomatitis virus, measles virus, Hepatitis virus, influenza virus, or combinations thereof. In some embodiments, the reporter is a fluorescent protein or luciferase. In some embodiments, the fluorescent protein is green fluorescent protein. In some embodiments, the therapeutic molecule is an immune modulating protein, a cellular signal modulating molecule, a proliferation modulating molecule, a cell death modulating molecule, or combinations thereof. In some embodiments, the mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the mammalian polypeptide comprises an extracellular domain of the receptor. In some embodiments, the mammalian polypeptide comprises a ligand or a secreted protein. In some embodiments, the mammalian polypeptide comprises ACE2, TRMPSS2, DPP4, CD4, CCR5, CXCR4, CD209, or CLEC4M. In some embodiments, the mammalian polypeptide comprises an amino acid sequence of at least 90% sequence identity to an amino acid sequence according to SEQ ID NO: 1. In some embodiments, the mammalian polypeptide comprises an amino acid sequence of at least 90% sequence identity to an amino acid sequence according to SEQ ID NO: 2.

In some embodiments, the transmembrane polypeptide comprises a transmembrane anchoring protein. In some embodiments, the transmembrane polypeptide comprises a spike glycoprotein transmembrane region, a mammalian membrane protein, an envelope protein, a nucleocapsid protein, or a cellular transmembrane protein. In some embodiments, the transmembrane polypeptide comprises VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120. In some embodiments, the VSVG transmembrane region comprises full length VSVG transmembrane region or a truncated VSVG transmembrane region. In some embodiments, the transmembrane polypeptide comprises a VSVG transmembrane region and a VSVG cytoplasmic tail. In some embodiments, the transmembrane polypeptide comprises an amino acid sequence at least about 90% identical to that set forth in SEQ ID NO: 3. In some embodiments, the transmembrane polypeptide comprises an amino acid sequence at least about 90% identical to that set forth in SEQ ID NO: 4

In some embodiments, the fusion protein further comprises an oligomerization domain. In some embodiments, the oligomerization domain is a dimerization domain. In some embodiments, the dimerization domain comprises a leucine zipper dimerization domain. In some embodiments, the oligomerization domain is a trimerization domain. In some embodiments, the trimerization domain comprises a post-fusion oligomerization domain of viral surface protein. In some embodiments, the trimerization domain comprises a D4 post-fusion trimerization domain of VSV-G protein. In some embodiments, the trimerization domain comprises a Dengue E protein post-fusion trimerization domain. In some embodiments, the trimerization domain comprises a foldon trimerization domain. In some embodiments, the trimerization domain comprises human C-propeptide of α1(I) collagen. In some embodiments, the oligomerization domain is a tetramerization domain. In some embodiments, the tetramerization domain comprises an influenza neuraminidase stem domain. In some embodiments, the oligomerization domain comprises an amino acid sequence that has at least 95% sequence identity to an amino acid sequence according to SEQ ID NOs: 5-18, or 28.

In some embodiments, when the fusion protein is expressed on the surface of the multivalent particle, the oligomerization domain is outside of the multivalent particle. In some embodiments, when the fusion protein is expressed on the surface of the multivalent particle, the oligomerization domain is outside of the multivalent particle and adjacent to a signal peptide. In some embodiments, when the fusion protein is expressed on the surface of the multivalent particle, the oligomerization domain is inside of the multivalent particle. In some embodiments, when the fusion protein is expressed on the surface of the multivalent particle, the oligomerization domain is inside of the multivalent particle and adjacent to the transmembrane polypeptide. In some embodiments, the fusion protein is expressed at least about 50 copies on a surface of the multivalent particle when it is expressed. In some embodiments, the fusion protein is expressed at least about 75 copies on a surface of the multivalent particle when it is expressed. In some embodiments, the fusion protein is expressed at least about 100 copies on a surface of the multivalent particle when it is expressed. In some embodiments, the fusion protein is expressed at least about 150 copies on a surface of the multivalent particle when it is expressed. In some embodiments, the fusion protein is expressed at least about 200 copies on a surface of the multivalent particle when it is expressed.

In some embodiments, the mammalian polypeptide comprises ACE2 and the transmembrane polypeptide comprises VSVG transmembrane region. In some embodiments, the mammalian polypeptide comprises ACE2 and the transmembrane polypeptide comprises spike protein S2 transmembrane region. In some embodiments, the mammalian polypeptide comprises ACE2 and the transmembrane polypeptide comprises a surface glycoprotein of an enveloped virus. In some embodiments, the mammalian polypeptide comprises DPP4 and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the composition further comprises a fourth nucleic acid sequence encoding a second fusion protein that comprises a second mammalian polypeptide that binds to the viral protein and a second transmembrane polypeptide wherein the second fusion protein is expressed at least about 10 copies on the surface of the multivalent particle when it is expressed.

In some embodiments, the second mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the second mammalian polypeptide comprises an extracellular domain of the receptor. In some embodiments, the second mammalian polypeptide comprises a ligand or a secreted protein. In some embodiments, the second mammalian polypeptide comprises ACE2, TRMPSS2, DPP4, CD4, CCR5, CXCR4, CD209, or CLEC4M. In some embodiments, the second mammalian polypeptide comprises an amino acid sequence of at least 90% sequence identity to an amino acid sequence according to SEQ ID NO: 1. In some embodiments, the second mammalian polypeptide comprises an amino acid sequence of at least 90% sequence identity to an amino acid sequence according to SEQ ID NO: 2.

In some embodiments, the second transmembrane polypeptide comprises a transmembrane anchoring protein. In some embodiments, the second transmembrane polypeptide comprises a spike glycoprotein transmembrane region, a mammalian membrane protein, an envelope protein, a nucleocapsid protein, or a cellular transmembrane protein. In some embodiments, the second transmembrane polypeptide comprises VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120. In some embodiments, the VSVG transmembrane region comprises full length VSVG transmembrane region or a truncated VSVG transmembrane region. In some embodiments, the VSVG transmembrane region comprises a VSVG transmembrane region and a VSVG cytoplasmic tail. In some embodiments, the second transmembrane polypeptide comprises an amino acid sequence at least about 90% identical to that set forth in SEQ ID NO: 3. In some embodiments, the second transmembrane polypeptide comprises an amino acid sequence at least about 90% identical to that set forth in SEQ ID NO: 4.

In some embodiments, the second fusion protein further comprises an oligomerization domain. In some embodiments, the oligomerization domain is a dimerization domain. In some embodiments, the dimerization domain comprises a leucine zipper dimerization domain. In some embodiments, the oligomerization domain is a trimerization domain. In some embodiments, the trimerization domain comprises a post-fusion oligomerization domain of viral surface protein. In some embodiments, the trimerization domain comprises a D4 post-fusion trimerization domain of VSV-G protein. In some embodiments, the trimerization domain comprises a Dengue E protein post-fusion trimerization domain. In some embodiments, the trimerization domain comprises a foldon trimerization domain. In some embodiments, the trimerization domain comprises human C-propeptide of α1(I) collagen. In some embodiments, the oligomerization domain is a tetramerization domain. In some embodiments, the tetramerization domain comprises an influenza neuraminidase stem domain. In some embodiments, the oligomerization domain comprises an amino acid sequence that has at least 95% sequence identity to an amino acid sequence according to SEQ ID NOs: 5-18, or 28.

In some embodiments, when the second fusion protein is expressed on the surface of the multivalent particle, the oligomerization domain is outside of the multivalent particle. In some embodiments, when the second fusion protein is expressed on the surface of the multivalent particle, the oligomerization domain is outside of the multivalent particle and adjacent to a signal peptide. In some embodiments, when the second fusion protein is expressed on the surface of the multivalent particle, the oligomerization domain is inside of the multivalent particle. In some embodiments, when the second fusion protein is expressed on the surface of the multivalent particle, the oligomerization domain is inside of the multivalent particle and adjacent to the transmembrane polypeptide. In some embodiments, the second fusion protein is expressed at least about 50 copies on a surface of the multivalent particle when it is expressed. In some embodiments, the second fusion protein is expressed at least about 75 copies on a surface of the multivalent particle when it is expressed. In some embodiments, the second fusion protein is expressed at least about 100 copies on a surface of the multivalent particle when it is expressed. In some embodiments, the second fusion protein is expressed at least about 150 copies on a surface of the multivalent particle when it is expressed. In some embodiments, the second fusion protein is expressed at least about 200 copies on a surface of the multivalent particle when it is expressed.

In some embodiments, the second mammalian polypeptide comprises ACE2 and the second transmembrane polypeptide comprises VSVG transmembrane region. In some embodiments, the second mammalian polypeptide comprises ACE2 and the second transmembrane polypeptide comprises spike protein S2 transmembrane region. In some embodiments, the second mammalian polypeptide comprises ACE2 and the second transmembrane polypeptide comprises a surface glycoprotein of an enveloped virus. In some embodiments, the second mammalian polypeptide comprises DPP4 and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the mammalian polypeptide comprises a viral entry receptor and the second mammalian polypeptide comprises a viral attachment receptor.

In some embodiments, the mammalian polypeptide comprises ACE2, the transmembrane polypeptide comprises VSVG transmembrane region, spike protein S1 transmembrane region, spike protein S2 transmembrane region, or a surface glycoprotein of an enveloped virus, the second mammalian polypeptide comprises a heparan sulfate proteoglycan, and the second transmembrane polypeptide comprises VSVG transmembrane region, spike protein S1 transmembrane region, spike protein S2 transmembrane region, or a surface glycoprotein of an enveloped virus. In some embodiments, the mammalian polypeptide comprises CD4 and the second mammalian peptide comprises, CCR5, CXCR4, or both. In some embodiments, the first nucleic acid sequence, the second nucleic acid sequence, and the third nucleic acid sequence are within a same vector. In some embodiments, the first nucleic acid sequence, the second nucleic acid sequence, and the third nucleic acid sequence are within different vectors. In some embodiments, the first nucleic acid sequence, the second nucleic acid sequence, the third nucleic acid sequence, and the fourth nucleic acid sequence are within a same vector. In some embodiments, the first nucleic acid sequence, the second nucleic acid sequence, third nucleic acid sequence, and the fourth nucleic acid sequence are within different vectors. In some embodiments, the nucleic acid sequence that encodes the first fusion protein and the second fusion protein and the second nucleic acid sequence and the third nucleic acid sequence are mRNAs. In some embodiments, the nucleic acid sequence that encodes the first fusion protein and the second fusion protein and the second nucleic acid sequence and the third nucleic acid sequence are DNA. In some embodiments, the composition comprises a vector, wherein the vector is a lentivirus vector, an adenovirus vector, or an adeno-associated virus vector.

Disclosed herein, in certain embodiments, are pharmaceutical compositions comprising the multivalent particles disclosed herein and a pharmaceutically acceptable excipient.

Disclosed herein, in certain embodiments are methods of treating a viral infection in a subject in need thereof, comprising administering to the subject the multivalent particle of the disclosure or the compositions of the disclosure. In some embodiments, the multivalent particle is administered intravenously. In some embodiments, the multivalent particle is administered through inhalation. In some embodiments, the multivalent particle is administered by an intraperitoneal injection. In some embodiments, the multivalent particle is administered by a subcutaneous injection. In some embodiments, the viral infection comprises an infection by SARS CoV-2, SARS CoV-1, MERS CoV. In some embodiments, the composition is administered intravenously. In some embodiments, the composition is administered through inhalation. In some embodiments, the composition is administered by an intraperitoneal injection. In some embodiments, the composition is administered by a subcutaneous injection. In some embodiments, the composition comprises a liposome. In some embodiments, the composition comprises an adeno-associated virus (AAV). In some embodiments, the composition comprises a lipid nanoparticle. In some embodiments, the composition comprises a polymer. In some embodiments, the SARS CoV-2, SARS CoV-1, MERS CoV are effectively neutralized in vivo by the multivalent particle or the composition. In some embodiments, the multivalent particle or the composition inhibits a respiratory symptom of the viral infection. In some embodiments, the multivalent particle or the composition induces robust immunity against different strains of the viral infection. In some embodiments, the viral infection comprises infection by SARS CoV-2, and the multivalent particle or the composition induces robust immunity against Delta variant of SARS CoV-2.

Disclosed herein, in certain embodiments, are methods of producing immunity against a viral infection in a subject in need thereof, comprising administering to the subject the multivalent particles of the disclosure or the compositions of the disclosure and a virus of the viral infection. In some embodiments, the multivalent particle is administered intravenously. In some embodiments, the multivalent particle is administered through inhalation. In some embodiments, the multivalent particle is administered by an intraperitoneal injection. In some embodiments, the multivalent particle is administered by a subcutaneous injection. In some embodiments, the viral infection comprises an infection by SARS CoV-2, SARS CoV-1, MERS CoV. In some embodiments, the composition is administered intravenously. In some embodiments, the composition is administered through inhalation. In some embodiments, the composition is administered by an intraperitoneal injection. In some embodiments, the composition is administered by a subcutaneous injection. In some embodiments, the composition comprises a liposome. In some embodiments, the composition comprises an adeno-associated virus (AAV). In some embodiments, the composition comprises a lipid nanoparticle. In some embodiments, the composition comprises a polymer.

In some embodiments, the SARS CoV-2, SARS CoV-1, MERS CoV are effectively neutralized in vivo by the multivalent particle or the composition. In some embodiments, the multivalent particle or the composition inhibits a respiratory symptom of the viral infection. In some embodiments, the multivalent particle or the composition induces robust immunity against different strains of the viral infection. In some embodiments, the viral infection comprises infection by SARS CoV-2, and the multivalent particle or the composition induces robust immunity against Delta variant of SARS CoV-2.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2D depicts results of a microneutralization assay using a decoy ACE2-MVP and two neutralizing antibodies.

FIG. 3E shows a comparison of the neutralizing activities of the ACE2-VGTM MVPs against a variety of SARS CoV-2 variants in pseudovirus infection assay using 293T/ACE2 cells as target cells.

FIG. 4A depicts a schematic of a decoy DPP4-MVP with fusion protein comprising a hemagglutinin envelope protein from measles virus (HCΔ18) and the DPP4 extracellular domain. FIG. 4C depicts the neutralizing activities of DDP4-MVPs were tested against lentiviruses pseudotyped with MERS spike (MERS-PVPs) in a microneutralization assay using H1650 cells as target cells. FIG. 4D shows the design and production of NA75-DPP4 MVPs. The schematic illustrates the DPP4-displaying constructs with DPP4 extracellular domain fused to the neuraminidase transmembrane domain from influenza virus. NA75-DPP4 MVPs were generated by co-transfecting NA75-DPP4-displaying constructs with a lentiviral packaging construct and lentiviral reporter construct. FIG. 4E shows the neutralizing activities of NA75-DPP4 MVPs determined in a MERS pseudovirus infection assay using H1650 cells as target cells.

FIG. 5 depicts decoy-MVPs displaying enzymatic-inactive H2A-ACE2, designated as H2A/ACE2-MVPs, have a reduced neutralizing activity against CoV-2 pseudovirus. The neutralizing activities of decoy-MVPs displaying either wild-type ACE2 or enzymatic-inactive H2A/ACE2 were determined in a SARS CoV-2 pseudovirus infection assay using 293T/ACE2 cells as target cells.

FIG. 6A-6E depict oligomerized display of wild-type and enzymatic-inactive ACE2 on multivalent particles. FIG. 6A depicts the structure of post-fusion VSV-G with D4 domain as the trimerization domain. FIG. 6B depicts schematics illustrating the oligomerized ACE2-displaying constructs with ACE2 extracellular domain fused to the VSVG transmembrane domain (ACE2-VGTN) for monomeric display or to the D4 post-fusion trimerization domain and VSVG transmembrane domain (ACE2-D4VG) for trimeric display. Decoy-MVPs displaying wild-type ACE2 (WT-ACE2) and enzymatic-inactive ACE2 (H2A/ACE2) were generated by co-transfecting corresponding ACE2-displaying constructs with a lentiviral packaging construct and lentiviral reporter construct. FIG. 6C depicts the copy number of ACE2 molecules on the decoy-MVPs were determined by quantitative Western-blot analyses. FIG. 6D shows representative TRPS analysis of ACE2-D4VG MVPs. FIG. 6E shows a representative Electron Microscopy image of H2A/ACE2-D4VG MVPs at nominal magnification of 150,000×.

FIG. 7A-7C depict augmenting the neutralizing activity of decoy-MVPs through oligomerized display of enzymatically-inactive H2A/ACE2 on MVPs. FIG. 7A depicts the neutralizing activities of the monomeric and trimeric wild-type ACE2-MVPs and enzymatically-inactive H2A/ACE2 MVPs as determined in a SARS CoV-2 pseudovirus infection assay using 293T/ACE2 cells as target cells. FIG. 7B depicts the neutralizing activities of the monomeric and trimeric wild-type ACE2 MVPs and enzymatically-inactive H2A/ACE2 MVPs as determined in a SARS CoV-1 pseudovirus infection assay using VERO-E6 cells as target cells. FIG. 7C compares the neutralizing activities of the H2A/ACE2-D4VG MVPs against a variety of SARS CoV-2 variants in pseudovirus infection assay using 293T/ACE2 cells as target cells.

FIG. 10A depicts the effect of trimeric H2A/ACE2-MVPs treatment on weight loss and FIG. 10B depicts the effect of trimeric H2A/ACE2-MVPs treatment on viral load in lung.

FIG. 11A depicts the effect of trimeric H2A/ACE-MVPs treatment on survival of SARS CoV-2 infected hACE2 transgenic mice. FIG. 11B shows the effects of the weight loss in hACE2 transgenic mice infected with the original WA strain of SARS CoV-2.

FIG. 12A shows the effect of SARS CoV-2 re-challenge on the body weight of infected hACE2 transgenic mice. FIG. 12B shows the effect of SARS CoV-2 re-challenge on the survival of infected hACE2 transgenic mice. FIG. 12C shows the effect of Delta variant re-challenge on the body weight of infected hACE2 transgenic mice. FIG. 12D shows the effect of Delta variant re-challenge on the survival of infected hACE2 transgenic mice.

FIG. 13A-13D show the characterization and in vitro neutralizing efficacy of EV-based ACE2-D4VG MVPs. FIG. 13A shows the particle size distribution of EV-based ACE2-D4VG MVP determined by Tunable Resistive Pulse Sensing Analysis using a qNano instrument. FIG. 13B shows the neutralizing activity of EV-based ACE2-D4VG MVP determined in a SARS CoV-2 pseudovirus infection assay using 293T/ACE2 cells as target cells. FIG. 13C shows the neutralizing activity of EV-based ACE2-D4VG MVPs determined in a SARS CoV-2 live virus neutralization assay. FIG. 13D shows the cytotoxicity of EV-based ACE2-D4VG MVPs in the same live virus neutralization assay described in FIG. 19C.

FIG. 15A shows monomeric decoy-MVP production by pseudo-typing ACE2 receptors on the lentiviral-based viral-like particles with viral genome. FIG. 15B shows Monomeric decoy-MVP production by pseudo-typing ACE2 receptors on the lentiviral-based viral-like particles without viral genome. FIG. 15C shows monomeric decoy-MVP production by pseudo-typing extracellular vesicles with ACE2 receptors.

FIG. 16A-16C show in vitro production of trimeric decoy-MVPs. FIG. 16A shows trimeric decoy-MVP production by pseudo-typing ACE2 receptors onto the lentiviral-based viral-like particles with viral genome. FIG. 16B shows trimeric decoy-MVP production by pseudo-typing ACE2 receptors onto the lentiviral-based viral-like particles without viral genome. FIG. 16C shows trimeric decoy-MVP production by pseudo-typing extracellular vesicles with ACE2 receptors.

FIG. 17A shows mixed monomeric and trimeric decoy-MVP production by pseudo-typing viral-entry receptors onto the lentiviral-based viral-like particles with viral genome. FIG. 17B shows mixed monomeric and trimeric decoy-MVP production by pseudo-typing viral-entry receptors onto the lentiviral-based viral-like particles without viral genome. FIG. 17C shows mixed monomeric and trimeric decoy-MVP production by pseudo-typing extracellular vesicles with viral-entry receptors.

FIG. 18A depicts the decoy receptor display configuration with the D4 trimerization domain located outside of the decoy-MVP and adjacent to the transmembrane domain. FIG. 18B depicts the decoy receptor display configuration with the D4 trimerization domain located inside of the decoy-MVP and adjacent to the transmembrane domain. FIG. 18C depicts the decoy receptor display configuration with the D4 trimerization domain located outside of the decoy-MVP and after the signal peptide. FIG. 18D depicts the D4 truncations for trimeric display of decoy receptors on decoy-MVPs. FIG. 18E shows the neutralizing activities of ACE2-D4VG MVPs with varied D4 location and length determined in a SARS CoV-2 pseudovirus infection assay using 293T/ACE2 cells as target cells.

FIG. 19A depicts the decoy receptor display configuration with the oligomerization domain located outside of the decoy-MVP and adjacent to the transmembrane domain. FIG. 19B depicts the decoy receptor display configuration with the oligomerization domain located inside of the decoy-MVP and adjacent to the transmembrane domain. FIG. 19C depicts the decoy receptor display configuration with the oligomerization domain located outside of the decoy-MVP and after the signal peptide.

DETAILED DESCRIPTION

Figure 1A:
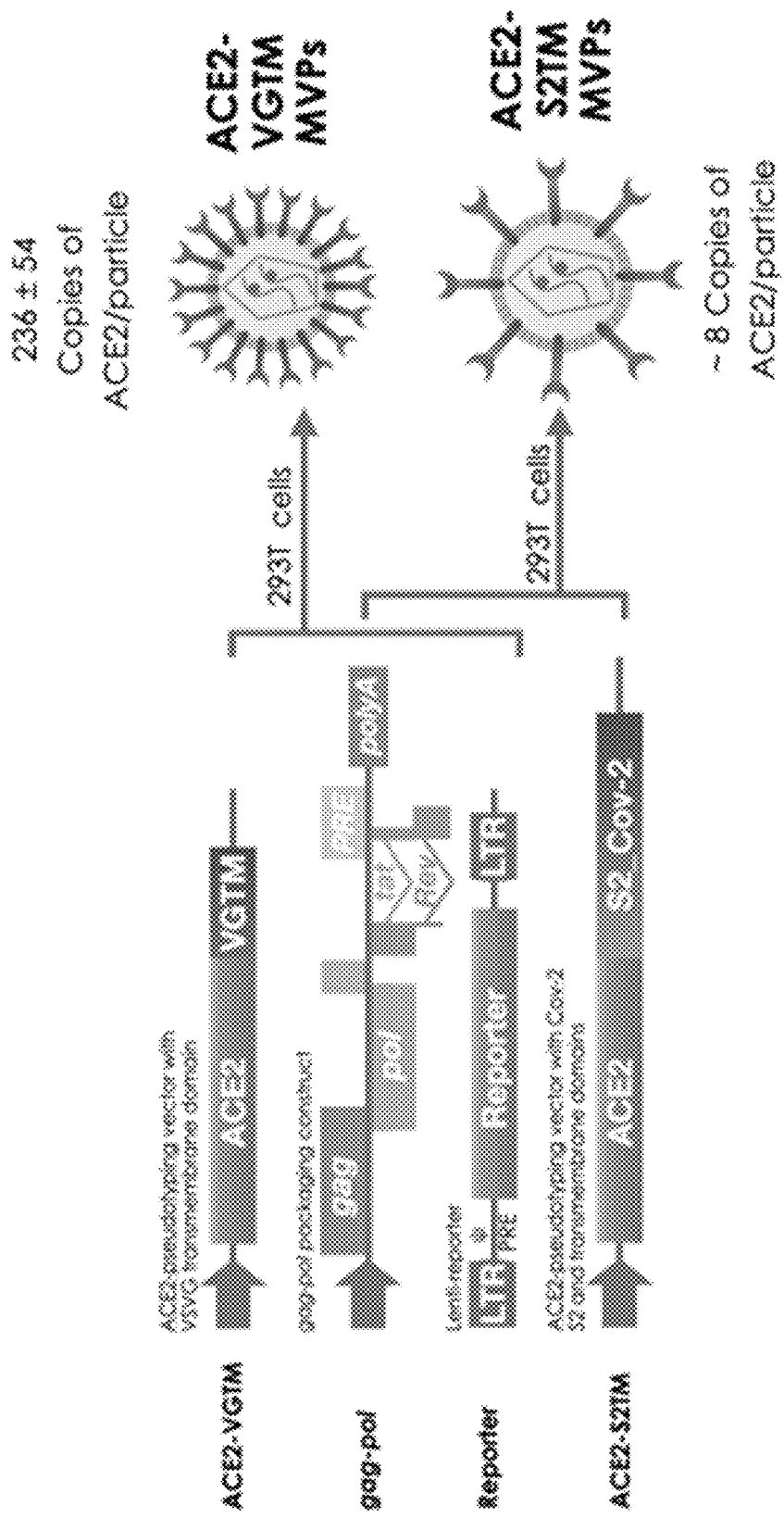
FIG. 1A depicts a schematic of pseudotyped lentiviral particles with a fusion protein consisting of the ACE2 extracellular domain and the membrane anchoring segment of a viral envelop protein.

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Multivalent Particles

The COVID-19 pandemic has caused tremendous losses in human life and economic activities. Current strategies such as antibody therapies for neutralizing viruses are not entirely effective. This is in part due to viruses being able to adapt strategies to effectively gain entry of host cells while evading the control by host immune systems. Nearly all viruses utilize a multivalent strategy for attachment and entry of host cells. Each virion display hundreds of copies of spike proteins, which can simultaneously interact with multiple copies of host cell receptors and attachment proteins.

In the case of coronaviruses, SARS CoV-2 virions display hundreds of copies of trimeric spike proteins, and utilize local trimeric as well as global multivalent interactions between spike and host cell proteins for attachment and entry. For example, host cell receptors angiotensin-converting enzyme 2 (ACE2) and dipeptidyl peptidase 4 (DPP4) are used as entry receptors for SARS CoV-1/2 and MERS coronaviruses, respectively. The densely packed spike proteins on the virions enable them to interact with multiple copies of ACE2 or DPP4 on the host cell surface. The boost in functional affinity that viruses receive through multivalent interactions is exponential, and nearly all enveloped and non-enveloped viruses use this multivalent strategy for attachment and host-cell entry. This provides a tremendous advantage to viruses. Most notably, the multivalent strategy enables viruses to turn relatively weak monovalent interactions with millimolar binding affinities into super-strong multivalent interactions with functional affinities in the nanomolar to picomolar range, in turn creating a high threshold for low or monovalent binders, such as neutralizing antibodies and recombinant protein inhibitors, to overcome. Moreover, viruses harness high mutation rates and multivalent binding to host cells to facilitate immune evasion. Spike mutagenesis and novel glycosylation patterns can effectively disrupt the neutralizing function of antibodies and other low-valency viral-blocking agents with little impact on viral attachment and entry. The current development of viral neutralization molecules does not address the multivalent nature of virions and host cell interaction. Mutations that are resistant to current combinations of clinically-tested neutralization antibodies have emerged and render existing therapies ineffective or less effective.

Given that trimeric and multivalent spike presentation on virions underlies SASR CoV-2's ability to escape immune control through rapid mutagenesis, here we describe multivalent particles (MVPs) displaying multiple copies of viral entry receptors, such as ACE2 and DPP4, that mirror the trimeric multivalent pattern of spike proteins on the virions. We showed that the MVPs effectively counteracts the multivalent interactions between viruses and host cell proteins and have improved potency against viruses such as coronavirus. Most importantly, the MVPs are insensitive to spike mutagenesis and therefore are variant-proof neutralizing therapeutics. Finally, treatment of SARS CoV-2 infection in representative animal models can effectively rescue lethal infection and induced robust immunity against dominant SARS CoV-2 strains including the Delta variant.

Described herein, in some embodiments, are MVPs displaying the ACE2 entry receptors as neutralizing decoys for SARS CoV-1/2. In some embodiments, the ACE2 MVPs inhibit the infection of the SARS CoV-2 viruses with a sub-picomolar $IC_{50}$ in pseudo-virus and live-virus neutralization assays. In some embodiments, the ACE2 MVPs are more potent than a ACE2 recombinant protein or a therapeutic neutralizing antibody. In some embodiments, each ACE2 MVP neutralizes at least about 10 pseudotyped SARS CoV-2 virions, and MVPs with higher ACE2 density can inhibit virus infection more completely. In some embodiments, the ACE2 MVPs of the disclosure can neutralize SARS CoV-2 variants and SARS CoV-1 at sub-picomolar $IC_{50}$s, and are thus broadly neutralizing against evolving SARS Coronaviruses utilizing ACE2 as an entry receptor. In some embodiments, the ACE2 MVPs are insensitive to spike mutagenesis and therefore are variant-proof neutralizing therapeutics. In some embodiments, MVPs displaying dipeptidyl peptidase 4 (DPP4-MVPs), the entry receptor for MERS CoV, can inhibit the infection of MERS pseudovirus at a picomolar $IC_{50}$. In some embodiments, the ACE2 MVPs are effective in rescue animals from lethal SARS CoV-2 infection. In some embodiments, treatment of SARS CoV-2 infection with the ACE2 MVPs are effective in inducing robust immunity against dominant SARS CoV-2 strains including the Delta variant.

Described herein, in some embodiments, are multivalent particles comprising a fusion protein that comprises a transmembrane polypeptide and a mammalian polypeptide that binds to a viral protein. In some embodiments, the viral protein is from SARS-CoV-1, SARS-CoV-2, MERS-CoV, Respiratory syncytial virus, HIV, or combinations thereof. In some embodiments, the viral protein is from SARS-CoV-2. In some embodiments, the viral protein is from MERS-CoV. In some embodiments, the viral protein is from SARS-CoV-1.

Various multivalent particles are contemplated herein. In some embodiments, the multivalent particle is synthetic. In some embodiments, the multivalent particle is recombinant. In some embodiments, the multivalent particle does not comprise viral genetic material. In some embodiments, the multivalent particle is a viral-like particle or virus-like particle. As used herein, viral-like particle and virus-like particle interchangeably. In some embodiments, the viral-like particle is synthetic. In some embodiments, the viral-like particle is recombinant. In some embodiments, the viral-like particle does not comprise viral genetic material. In some embodiments, the multivalent particle is an extracellular vesicle. In some embodiments, the multivalent particle is an exosome. In some embodiments, the multivalent particle is an ectosome.

Multivalent particles as described herein, in some embodiments, comprise a fusion protein, wherein the fusion protein is expressed at multiple copies on a surface of the multivalent particle. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the multivalent particle. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the multivalent particle. In some embodiments, the fusion protein is expressed at least or about 10 copies on a surface of the multivalent particle. In some embodiments, the fusion protein is expressed at least or about 25 copies on a surface of the multivalent particle. In some embodiments, the fusion protein is expressed at least or about 50 copies on a surface of the multivalent particle. In some embodiments, the fusion protein is expressed at least or about 75 copies on a surface of the multivalent particle. In some embodiments, the fusion protein is expressed at least or about 100 copies on a surface of the multivalent particle. In some embodiments, the fusion protein is expressed at least or about 125 copies on a surface of the multivalent particle. In some embodiments, the fusion protein is expressed at least or about 150 copies on a surface of the multivalent particle. In some embodiments, the fusion protein is expressed at least or about 175 copies on a surface of the multivalent particle. In some embodiments, the fusion protein is expressed at least or about 200 copies on a surface of the multivalent particle. In some embodiments, the fusion protein is expressed at least or about 225 copies on a surface of the multivalent particle. In some embodiments, the fusion protein is expressed at least or about 250 copies on a surface of the multivalent particle. In some embodiments, the fusion protein is expressed at least or about 275 copies on a surface of the multivalent particle. In some embodiments, the fusion protein is expressed at least or about 300 copies on a surface of the multivalent particle.

In some embodiments, the multivalent particle is a viral-like particle. The viral-like particle as described herein, in some embodiments, comprise a fusion protein, wherein the fusion protein is expressed at multiple copies on a surface of the viral-like particle. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the viral-like particle. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the viral-like particle. In some embodiments, the fusion protein is expressed at least or about 10 copies on a surface of the viral-like particle. In some embodiments, the fusion protein is expressed at least or about 25 copies on a surface of the viral-like particle. In some embodiments, the fusion protein is expressed at least or about 50 copies on a surface of the viral-like particle. In some embodiments, the fusion protein is expressed at least or about 75 copies on a surface of the viral-like particle. In some embodiments, the fusion protein is expressed at least or about 100 copies on a surface of the viral-like particle. In some embodiments, the fusion protein is expressed at least or about 125 copies on a surface of the viral-like particle. In some embodiments, the fusion protein is expressed at least or about 150 copies on a surface of the viral-like particle. In some embodiments, the fusion protein is expressed at least or about 175 copies on a surface of the viral-like particle. In some embodiments, the fusion protein is expressed at least or about 200 copies on a surface of the viral-like particle. In some embodiments, the fusion protein is expressed at least or about 225 copies on a surface of the viral-like particle. In some embodiments, the fusion protein is expressed at least or about 250 copies on a surface of the viral-like particle. In some embodiments, the fusion protein is expressed at least or about 275 copies on a surface of the viral-like particle. In some embodiments, the fusion protein is expressed at least or about 300 copies on a surface of the viral-like particle.

In some embodiments, the multivalent particle is an extracellular vesicle. The extracellular vesicle as described herein, in some embodiments, comprise a fusion protein, wherein the fusion protein is expressed at multiple copies on a surface of the extracellular vesicle. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the extracellular vesicle. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the extracellular vesicle. In some embodiments, the fusion protein is expressed at least or about 10 copies on a surface of the extracellular vesicle. In some embodiments, the fusion protein is expressed at least or about 25 copies on a surface of the extracellular vesicle. In some embodiments, the fusion protein is expressed at least or about 50 copies on a surface of the extracellular vesicle. In some embodiments, the fusion protein is expressed at least or about 75 copies on a surface of the extracellular vesicle. In some embodiments, the fusion protein is expressed at least or about 100 copies on a surface of the extracellular vesicle. In some embodiments, the fusion protein is expressed at least or about 125 copies on a surface of the extracellular vesicle. In some embodiments, the fusion protein is expressed at least or about 150 copies on a surface of the extracellular vesicle. In some embodiments, the fusion protein is expressed at least or about 175 copies on a surface of the extracellular vesicle. In some embodiments, the fusion protein is expressed at least or about 200 copies on a surface of the extracellular vesicle. In some embodiments, the fusion protein is expressed at least or about 225 copies on a surface of the extracellular vesicle. In some embodiments, the fusion protein is expressed at least or about 250 copies on a surface of the extracellular vesicle. In some embodiments, the fusion protein is expressed at least or about 275 copies on a surface of the extracellular vesicle. In some embodiments, the fusion protein is expressed at least or about 300 copies on a surface of the extracellular vesicle.

In some embodiments, the multivalent particle is an exosome. The exosome as described herein, in some embodiments, comprise a fusion protein, wherein the fusion protein is expressed at multiple copies on a surface of the exosome. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the exosome. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the exosome. In some embodiments, the fusion protein is expressed at least or about 10 copies on a surface of the exosome. In some embodiments, the fusion protein is expressed at least or about 25 copies on a surface of the exosome. In some embodiments, the fusion protein is expressed at least or about 50 copies on a surface of the exosome. In some embodiments, the fusion protein is expressed at least or about 75 copies on a surface of the exosome. In some embodiments, the fusion protein is expressed at least or about 100 copies on a surface of the exosome. In some embodiments, the fusion protein is expressed at least or about 125 copies on a surface of the exosome. In some embodiments, the fusion protein is expressed at least or about 150 copies on a surface of the exosome. In some embodiments, the fusion protein is expressed at least or about 175 copies on a surface of the exosome. In some embodiments, the fusion protein is expressed at least or about 200 copies on a surface of the exosome. In some embodiments, the fusion protein is expressed at least or about 225 copies on a surface of the exosome. In some embodiments, the fusion protein is expressed at least or about 250 copies on a surface of the exosome. In some embodiments, the fusion protein is expressed at least or about 275 copies on a surface of the exosome. In some embodiments, the fusion protein is expressed at least or about 300 copies on a surface of the exosome.

In some embodiments, the multivalent particle is an ectosome. The ectosome as described herein, in some embodiments, comprise a fusion protein, wherein the fusion protein is expressed at multiple copies on a surface of the ectosome. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the ectosome. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the ectosome. In some embodiments, the fusion protein is expressed at least or about 10 copies on a surface of the ectosome. In some embodiments, the fusion protein is expressed at least or about 25 copies on a surface of the ectosome. In some embodiments, the fusion protein is expressed at least or about 50 copies on a surface of the ectosome. In some embodiments, the fusion protein is expressed at least or about 75 copies on a surface of the ectosome. In some embodiments, the fusion protein is expressed at least or about 100 copies on a surface of the ectosome. In some embodiments, the fusion protein is expressed at least or about 125 copies on a surface of the ectosome. In some embodiments, the fusion protein is expressed at least or about 150 copies on a surface of the ectosome. In some embodiments, the fusion protein is expressed at least or about 175 copies on a surface of the ectosome. In some embodiments, the fusion protein is expressed at least or about 200 copies on a surface of the ectosome. In some embodiments, the fusion protein is expressed at least or about 225 copies on a surface of the ectosome. In some embodiments, the fusion protein is expressed at least or about 250 copies on a surface of the ectosome. In some embodiments, the fusion protein is expressed at least or about 275 copies on a surface of the ectosome. In some embodiments, the fusion protein is expressed at least or about 300 copies on a surface of the ectosome.

In some embodiments, the multivalent particle is a replication competent virus. The replication competent virus as described herein, in some embodiments, comprise a fusion protein, wherein the fusion protein is expressed at multiple copies on a surface of the replication competent virus. In some embodiments, the fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the replication competent virus. In some embodiments, the fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the replication competent virus. In some embodiments, the fusion protein is expressed at least or about 10 copies on a surface of the replication competent virus. In some embodiments, the fusion protein is expressed at least or about 25 copies on a surface of the replication competent virus. In some embodiments, the fusion protein is expressed at least or about 50 copies on a surface of the replication competent virus. In some embodiments, the fusion protein is expressed at least or about 75 copies on a surface of the replication competent virus. In some embodiments, the fusion protein is expressed at least or about 100 copies on a surface of the replication competent virus. In some embodiments, the fusion protein is expressed at least or about 125 copies on a surface of the replication competent virus. In some embodiments, the fusion protein is expressed at least or about 150 copies on a surface of the replication competent virus. In some embodiments, the fusion protein is expressed at least or about 175 copies on a surface of the replication competent virus. In some embodiments, the fusion protein is expressed at least or about 200 copies on a surface of the replication competent virus. In some embodiments, the fusion protein is expressed at least or about 225 copies on a surface of the replication competent virus. In some embodiments, the fusion protein is expressed at least or about 250 copies on a surface of the replication competent virus. In some embodiments, the fusion protein is expressed at least or about 275 copies on a surface of the replication competent virus. In some embodiments, the fusion protein is expressed at least or about 300 copies on a surface of the replication competent virus.

Multivalent particles as described herein, in some embodiments, comprise a second fusion protein, wherein the second fusion protein is expressed at multiple copies on a surface of the multivalent particle. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the multivalent particle. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the multivalent particle. In some embodiments, the second fusion protein is expressed at least or about 10 copies on a surface of the multivalent particle. In some embodiments, the second fusion protein is expressed at least or about 25 copies on a surface of the multivalent particle. In some embodiments, the second fusion protein is expressed at least or about 50 copies on a surface of the multivalent particle. In some embodiments, the second fusion protein is expressed at least or about 75 copies on a surface of the multivalent particle. In some embodiments, the second fusion protein is expressed at least or about 100 copies on a surface of the multivalent particle. In some embodiments, the second fusion protein is expressed at least or about 125 copies on a surface of the multivalent particle. In some embodiments, the second fusion protein is expressed at least or about 150 copies on a surface of the multivalent particle. In some embodiments, the second fusion protein is expressed at least or about 175 copies on a surface of the multivalent particle. In some embodiments, the second fusion protein is expressed at least or about 200 copies on a surface of the multivalent particle. In some embodiments, the second fusion protein is expressed at least or about 225 copies on a surface of the multivalent particle. In some embodiments, the second fusion protein is expressed at least or about 250 copies on a surface of the multivalent particle. In some embodiments, the second fusion protein is expressed at least or about 275 copies on a surface of the multivalent particle. In some embodiments, the second fusion protein is expressed at least or about 300 copies on a surface of the multivalent particle.

The viral-like particle as described herein, in some embodiments, comprise a second fusion protein, wherein the second fusion protein is expressed at multiple copies on a surface of the viral-like particle. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the viral-like particle. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the viral-like particle. In some embodiments, the second fusion protein is expressed at least or about 10 copies on a surface of the viral-like particle. In some embodiments, the second fusion protein is expressed at least or about 25 copies on a surface of the viral-like particle. In some embodiments, the second fusion protein is expressed at least or about 50 copies on a surface of the viral-like particle. In some embodiments, the second fusion protein is expressed at least or about 75 copies on a surface of the viral-like particle. In some embodiments, the second fusion protein is expressed at least or about 100 copies on a surface of the viral-like particle. In some embodiments, the second fusion protein is expressed at least or about 125 copies on a surface of the viral-like particle. In some embodiments, the second fusion protein is expressed at least or about 150 copies on a surface of the viral-like particle. In some embodiments, the second fusion protein is expressed at least or about 175 copies on a surface of the viral-like particle. In some embodiments, the second fusion protein is expressed at least or about 200 copies on a surface of the viral-like particle. In some embodiments, the second fusion protein is expressed at least or about 225 copies on a surface of the viral-like particle. In some embodiments, the second fusion protein is expressed at least or about 250 copies on a surface of the viral-like particle. In some embodiments, the second fusion protein is expressed at least or about 275 copies on a surface of the viral-like particle. In some embodiments, the second fusion protein is expressed at least or about 300 copies on a surface of the viral-like particle.

The extracellular vesicle, as described herein, in some embodiments, comprise a second fusion protein, wherein the second fusion protein is expressed at multiple copies on a surface of the extracellular vesicle. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the extracellular vesicle. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the extracellular vesicle. In some embodiments, the second fusion protein is expressed at least or about 10 copies on a surface of the extracellular vesicle. In some embodiments, the second fusion protein is expressed at least or about 25 copies on a surface of the extracellular vesicle. In some embodiments, the second fusion protein is expressed at least or about 50 copies on a surface of the extracellular vesicle. In some embodiments, the second fusion protein is expressed at least or about 75 copies on a surface of the extracellular vesicle. In some embodiments, the second fusion protein is expressed at least or about 100 copies on a surface of the extracellular vesicle. In some embodiments, the second fusion protein is expressed at least or about 125 copies on a surface of the extracellular vesicle. In some embodiments, the second fusion protein is expressed at least or about 150 copies on a surface of the extracellular vesicle. In some embodiments, the second fusion protein is expressed at least or about 175 copies on a surface of the extracellular vesicle. In some embodiments, the second fusion protein is expressed at least or about 200 copies on a surface of the extracellular vesicle. In some embodiments, the second fusion protein is expressed at least or about 225 copies on a surface of the extracellular vesicle. In some embodiments, the second fusion protein is expressed at least or about 250 copies on a surface of the extracellular vesicle. In some embodiments, the second fusion protein is expressed at least or about 275 copies on a surface of the extracellular vesicle. In some embodiments, the second fusion protein is expressed at least or about 300 copies on a surface of the extracellular vesicle.

The exosome, as described herein, in some embodiments, comprise a second fusion protein, wherein the second fusion protein is expressed at multiple copies on a surface of the exosome. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the exosome. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the exosome. In some embodiments, the second fusion protein is expressed at least or about 10 copies on a surface of the exosome. In some embodiments, the second fusion protein is expressed at least or about 25 copies on a surface of the exosome. In some embodiments, the second fusion protein is expressed at least or about 50 copies on a surface of the exosome. In some embodiments, the second fusion protein is expressed at least or about 75 copies on a surface of the exosome. In some embodiments, the second fusion protein is expressed at least or about 100 copies on a surface of the exosome. In some embodiments, the second fusion protein is expressed at least or about 125 copies on a surface of the exosome. In some embodiments, the second fusion protein is expressed at least or about 150 copies on a surface of the exosome. In some embodiments, the second fusion protein is expressed at least or about 175 copies on a surface of the exosome. In some embodiments, the second fusion protein is expressed at least or about 200 copies on a surface of the exosome. In some embodiments, the second fusion protein is expressed at least or about 225 copies on a surface of the exosome. In some embodiments, the second fusion protein is expressed at least or about 250 copies on a surface of the exosome. In some embodiments, the second fusion protein is expressed at least or about 275 copies on a surface of the exosome. In some embodiments, the second fusion protein is expressed at least or about 300 copies on a surface of the exosome.

The ectosome, as described herein, in some embodiments, comprise a second fusion protein, wherein the second fusion protein is expressed at multiple copies on a surface of the ectosome. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the ectosome. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the ectosome. In some embodiments, the second fusion protein is expressed at least or about 10 copies on a surface of the ectosome. In some embodiments, the second fusion protein is expressed at least or about 25 copies on a surface of the ectosome. In some embodiments, the second fusion protein is expressed at least or about 50 copies on a surface of the ectosome. In some embodiments, the second fusion protein is expressed at least or about 75 copies on a surface of the ectosome. In some embodiments, the second fusion protein is expressed at least or about 100 copies on a surface of the ectosome. In some embodiments, the second fusion protein is expressed at least or about 125 copies on a surface of the ectosome. In some embodiments, the second fusion protein is expressed at least or about 150 copies on a surface of the ectosome. In some embodiments, the second fusion protein is expressed at least or about 175 copies on a surface of the ectosome. In some embodiments, the second fusion protein is expressed at least or about 200 copies on a surface of the ectosome. In some embodiments, the second fusion protein is expressed at least or about 225 copies on a surface of the ectosome. In some embodiments, the second fusion protein is expressed at least or about 250 copies on a surface of the ectosome. In some embodiments, the second fusion protein is expressed at least or about 275 copies on a surface of the ectosome. In some embodiments, the second fusion protein is expressed at least or about 300 copies on a surface of the ectosome.

The replication competent virus, as described herein, in some embodiments, comprise a second fusion protein, wherein the second fusion protein is expressed at multiple copies on a surface of the replication competent virus. In some embodiments, the second fusion protein is expressed at least or about 5, 10, 15, 20, 25, 30, 35, 40, 45, 50, 75, 100, 125, 150, 175, 200, 225, 250, 275, 300, 325, 350, 375, 400, or more than 400 copies on a surface of the replication competent virus. In some embodiments, the second fusion protein is expressed at least or about 5 to about 400, about 20 to about 400, about 10 to about 300, about 20 to about 300, about 20 to about 200, about 50 to about 150, about 20 to about 100, or about 50 to about 100 copies on a surface of the replication competent virus. In some embodiments, the second fusion protein is expressed at least or about 10 copies on a surface of the replication competent virus. In some embodiments, the second fusion protein is expressed at least or about 25 copies on a surface of the replication competent virus. In some embodiments, the second fusion protein is expressed at least or about 50 copies on a surface of the replication competent virus. In some embodiments, the second fusion protein is expressed at least or about 75 copies on a surface of the replication competent virus. In some embodiments, the second fusion protein is expressed at least or about 100 copies on a surface of the replication competent virus. In some embodiments, the second fusion protein is expressed at least or about 125 copies on a surface of the replication competent virus. In some embodiments, the second fusion protein is expressed at least or about 150 copies on a surface of the replication competent virus. In some embodiments, the second fusion protein is expressed at least or about 175 copies on a surface of the replication competent virus. In some embodiments, the second fusion protein is expressed at least or about 200 copies on a surface of the replication competent virus. In some embodiments, the second fusion protein is expressed at least or about 225 copies on a surface of the replication competent virus. In some embodiments, the second fusion protein is expressed at least or about 250 copies on a surface of the replication competent virus. In some embodiments, the second fusion protein is expressed at least or about 275 copies on a surface of the replication competent virus. In some embodiments, the second fusion protein is expressed at least or about 300 copies on a surface of the replication competent virus.

Described herein, in some embodiments, are multivalent particles comprising improved binding properties. In some embodiments, the multivalent particle comprises a binding affinity (e.g., $K_D$) to the viral protein of less than 100 pM, less than 200 pM, less than 300 pM, less than 400 pM, less than 500 pM, less than 600 pM, less than 700 pM, less than 800 pM, or less than 900 pM In some embodiments, the multivalent particle comprises a $K_D$ of less than 1 nM, less than 1.2 nM, less than 2 nM, less than 5 nM, or less than 10 nM. In some instances, the multivalent particle comprises a $K_D$ of less than 1 nM. In some instances, the multivalent particle comprises a $K_D$ of less than 1.2 nM. In some instances, the multivalent particle comprises a $K_D$ of less than 2 nM. In some instances, the multivalent particle comprises a $K_D$ of less than 5 nM. In some instances, the multivalent particle comprises a $K_D$ of less than 10 nM.

In some embodiments, the multivalent particle comprises an IC50 of less than 20 picomolar (pM) in a neutralization assay. In some embodiments, the multivalent particle comprises an IC50 of less than 15 picomolar (pM) in a neutralization assay. In some embodiments, the multivalent particle comprises an IC50 of less than 10 picomolar (pM) in a neutralization assay. In some embodiments, the multivalent particle comprises an IC50 of less than 5 picomolar (pM) in a neutralization assay. In some embodiments, the multivalent particle comprises an IC50 of less than 2.5 picomolar (pM) in a neutralization assay. In some embodiments, the multivalent particle comprises an IC50 of less than 1 picomolar (pM) in a neutralization assay. In some embodiments, the multivalent particle comprises an IC50 of less than 0.5 picomolar (pM) in a neutralization assay.

Mammalian Polypeptides

Described herein, in some embodiments, are multivalent particles comprising a fusion protein that comprises a mammalian polypeptide that binds to a viral protein and a transmembrane polypeptide, wherein the mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the mammalian polypeptide comprises an extracellular domain of the receptor. In some embodiments, the mammalian polypeptide is a Type I receptor. In some embodiments, the mammalian polypeptide is a Type II receptor. In some embodiments, the mammalian polypeptide is a multi-span transmembrane protein. In some embodiments, the mammalian polypeptide is a de novo designed viral-binding protein. In some embodiments, the de novo designed viral-binding protein comprises using phage display or yeast display. In some embodiments, the mammalian polypeptide comprises a ligand or a secreted protein.

In some embodiments, the mammalian polypeptide comprises ACE2, TRMPSS2, DPP4, CD4, CCR5, CXCR4, CD209, or CLEC4M. In some embodiments, the mammalian polypeptide comprises ACE2. In some embodiments, the mammalian polypeptide comprises DPP4.

In some embodiments, the mammalian polypeptide comprises an amino acid sequence of at least 75% sequence identity to an amino acid sequence according to SEQ ID NO: 1. In some embodiments, the mammalian polypeptide comprises an amino acid sequence of at least 80% sequence identity to an amino acid sequence according to SEQ ID NO: 1. In some embodiments, the mammalian polypeptide comprises an amino acid sequence of at least 85% sequence identity to an amino acid sequence according to SEQ ID NO: 1. In some embodiments, the mammalian polypeptide comprises an amino acid sequence of at least 90% sequence identity to an amino acid sequence according to SEQ ID NO: 1. In some embodiments, the mammalian polypeptide comprises an amino acid sequence of at least 95% sequence identity to an amino acid sequence according to SEQ ID NO: 1. In some embodiments, the mammalian polypeptide comprises an amino acid sequence of at least 98% sequence identity to an amino acid sequence according to SEQ ID NO: 1. In some embodiments, the mammalian polypeptide comprises an amino acid sequence of at least 99% sequence identity to an amino acid sequence according to SEQ ID NO: 1.

In some embodiments, the mammalian polypeptide comprises an amino acid sequence of at least 75% sequence homology to an amino acid sequence according to SEQ ID NO: 1. In some embodiments, the mammalian polypeptide comprises an amino acid sequence of at least 80% sequence homology to an amino acid sequence according to SEQ ID NO: 1. In some embodiments, the mammalian polypeptide comprises an amino acid sequence of at least 85% sequence homology to an amino acid sequence according to SEQ ID NO: 1. In some embodiments, the mammalian polypeptide comprises an amino acid sequence of at least 90% sequence homology to an amino acid sequence according to SEQ ID NO: 1. In some embodiments, the mammalian polypeptide comprises an amino acid sequence of at least 95% sequence homology to an amino acid sequence according to SEQ ID NO: 1. In some embodiments, the mammalian polypeptide comprises an amino acid sequence of at least 98% sequence homology to an amino acid sequence according to SEQ ID NO: 1. In some embodiments, the mammalian polypeptide comprises an amino acid sequence of at least 99% sequence homology to an amino acid sequence according to SEQ ID NO: 1.

In some instances, the mammalian polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 consecutive amino acids of SEQ ID NO: 1.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, the mammalian polypeptide comprises an amino acid sequence of at least 75% sequence identity to an amino acid sequence according to SEQ ID NO: 2. In some embodiments, the mammalian polypeptide comprises an amino acid sequence of at least 80% sequence identity to an amino acid sequence according to SEQ ID NO: 2. In some embodiments, the mammalian polypeptide comprises an amino acid sequence of at least 85% sequence identity to an amino acid sequence according to SEQ ID NO: 2. In some embodiments, the mammalian polypeptide comprises an amino acid sequence of at least 90% sequence identity to an amino acid sequence according to SEQ ID NO: 2. In some embodiments, the mammalian polypeptide comprises an amino acid sequence of at least 95% sequence identity to an amino acid sequence according to SEQ ID NO: 2. In some embodiments, the mammalian polypeptide comprises an amino acid sequence of at least 98% sequence identity to an amino acid sequence according to SEQ ID NO: 2. In some embodiments, the mammalian polypeptide comprises an amino acid sequence of at least 99% sequence identity to an amino acid sequence according to SEQ ID NO: 2.

In some embodiments, the mammalian polypeptide comprises an amino acid sequence of at least 75% sequence homology to an amino acid sequence according to SEQ ID NO: 2. In some embodiments, the mammalian polypeptide comprises an amino acid sequence of at least 80% sequence homology to an amino acid sequence according to SEQ ID NO: 2. In some embodiments, the mammalian polypeptide comprises an amino acid sequence of at least 85% sequence homology to an amino acid sequence according to SEQ ID NO: 2. In some embodiments, the mammalian polypeptide comprises an amino acid sequence of at least 90% sequence homology to an amino acid sequence according to SEQ ID NO: 2. In some embodiments, the mammalian polypeptide comprises an amino acid sequence of at least 95% sequence homology to an amino acid sequence according to SEQ ID NO: 2. In some embodiments, the mammalian polypeptide comprises an amino acid sequence of at least 98% sequence homology to an amino acid sequence according to SEQ ID NO: 2. In some embodiments, the mammalian polypeptide comprises an amino acid sequence of at least 99% sequence homology to an amino acid sequence according to SEQ ID NO: 2.

In some instances, the mammalian polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 2.

Described herein, in some embodiments, are multivalent particles comprising a fusion protein that comprises a mammalian polypeptide that binds to a viral protein and a transmembrane polypeptide, wherein the multivalent particles further comprises a second fusion protein that comprises a second mammalian polypeptide that binds to the viral protein and a second transmembrane polypeptide. In some embodiments, the second mammalian polypeptide comprises a receptor that has binding specificity for the viral protein. In some embodiments, the receptor comprises a viral entry receptor or a viral attachment receptor. In some embodiments, the receptor is both a viral entry receptor and a viral attachment receptor. In some embodiments, the second mammalian polypeptide comprises an extracellular domain of the receptor. In some embodiments, the second mammalian polypeptide is a Type I receptor. In some embodiments, the second mammalian polypeptide is a Type II receptor. In some embodiments, the mammalian polypeptide is a multi-span transmembrane protein. In some embodiments, the mammalian polypeptide is a de novo designed viral-binding protein. In some embodiments, the de novo designed viral-binding protein comprises using phage display or yeast display. In some embodiments, the second mammalian polypeptide comprises a ligand or a secreted protein.

In some embodiments, the second mammalian polypeptide comprises ACE2, TRMPSS2, DPP4, CD4, CCR5, CXCR4, CD209, or CLEC4M. In some embodiments, the second mammalian polypeptide comprises ACE2. In some embodiments, the second mammalian polypeptide comprises DPP4.

In some embodiments, the second mammalian polypeptide comprises an amino acid sequence of at least 75% sequence identity to an amino acid sequence according to SEQ ID NO: 1. In some embodiments, the second mammalian polypeptide comprises an amino acid sequence of at least 80% sequence identity to an amino acid sequence according to SEQ ID NO: 1. In some embodiments, the second mammalian polypeptide comprises an amino acid sequence of at least 85% sequence identity to an amino acid sequence according to SEQ ID NO: 1. In some embodiments, the second mammalian polypeptide comprises an amino acid sequence of at least 90% sequence identity to an amino acid sequence according to SEQ ID NO: 1. In some embodiments, the second mammalian polypeptide comprises an amino acid sequence of at least 95% sequence identity to an amino acid sequence according to SEQ ID NO: 1. In some embodiments, the second mammalian polypeptide comprises an amino acid sequence of at least 98% sequence identity to an amino acid sequence according to SEQ ID NO: 1. In some embodiments, the second mammalian polypeptide comprises an amino acid sequence of at least 99% sequence identity to an amino acid sequence according to SEQ ID NO: 1.

In some embodiments, the second mammalian polypeptide comprises an amino acid sequence of at least 75% sequence homology to an amino acid sequence according to SEQ ID NO: 1. In some embodiments, the second mammalian polypeptide comprises an amino acid sequence of at least 80% sequence homology to an amino acid sequence according to SEQ ID NO: 1. In some embodiments, the second mammalian polypeptide comprises an amino acid sequence of at least 85% sequence homology to an amino acid sequence according to SEQ ID NO: 1. In some embodiments, the second mammalian polypeptide comprises an amino acid sequence of at least 90% sequence homology to an amino acid sequence according to SEQ ID NO: 1. In some embodiments, the second mammalian polypeptide comprises an amino acid sequence of at least 95% sequence homology to an amino acid sequence according to SEQ ID NO: 1. In some embodiments, the second mammalian polypeptide comprises an amino acid sequence of at least 98% sequence homology to an amino acid sequence according to SEQ ID NO: 1. In some embodiments, the second mammalian polypeptide comprises an amino acid sequence of at least 99% sequence homology to an amino acid sequence according to SEQ ID NO: 1.

In some instances, the second mammalian polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 consecutive amino acids of SEQ ID NO: 1.

In some embodiments, the second mammalian polypeptide comprises an amino acid sequence of at least 75% sequence identity to an amino acid sequence according to SEQ ID NO: 2. In some embodiments, the second mammalian polypeptide comprises an amino acid sequence of at least 80% sequence identity to an amino acid sequence according to SEQ ID NO: 2. In some embodiments, the second mammalian polypeptide comprises an amino acid sequence of at least 85% sequence identity to an amino acid sequence according to SEQ ID NO: 2. In some embodiments, the second mammalian polypeptide comprises an amino acid sequence of at least 90% sequence identity to an amino acid sequence according to SEQ ID NO: 2. In some embodiments, the second mammalian polypeptide comprises an amino acid sequence of at least 95% sequence identity to an amino acid sequence according to SEQ ID NO: 2. In some embodiments, the second mammalian polypeptide comprises an amino acid sequence of at least 98% sequence identity to an amino acid sequence according to SEQ ID NO: 2. In some embodiments, the second mammalian polypeptide comprises an amino acid sequence of at least 99% sequence identity to an amino acid sequence according to SEQ ID NO: 2.

In some embodiments, the second mammalian polypeptide comprises an amino acid sequence of at least 75% sequence homology to an amino acid sequence according to SEQ ID NO: 2. In some embodiments, the second mammalian polypeptide comprises an amino acid sequence of at least 80% sequence homology to an amino acid sequence according to SEQ ID NO: 2. In some embodiments, the second mammalian polypeptide comprises an amino acid sequence of at least 85% sequence homology to an amino acid sequence according to SEQ ID NO: 2. In some embodiments, the second mammalian polypeptide comprises an amino acid sequence of at least 90% sequence homology to an amino acid sequence according to SEQ ID NO: 2. In some embodiments, the second mammalian polypeptide comprises an amino acid sequence of at least 95% sequence homology to an amino acid sequence according to SEQ ID NO: 2. In some embodiments, the second mammalian polypeptide comprises an amino acid sequence of at least 98% sequence homology to an amino acid sequence according to SEQ ID NO: 2. In some embodiments, the second mammalian polypeptide comprises an amino acid sequence of at least 99% sequence homology to an amino acid sequence according to SEQ ID NO: 2.

In some instances, the second mammalian polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 2.

Oligomerization Domains

In some embodiments, the multivalent particle comprises an oligomerization domain. In some embodiments, the fusion protein comprises an oligomerization domain. In some embodiments, the oligomerization domain is a dimerization domain. In some embodiments, the dimerization domain comprises a leucine zipper dimerization domain. In some embodiments, the oligomerization domain is a trimerization domain. In some embodiments, the trimerization domain comprises a post-fusion oligomerization domain of viral surface protein. In some embodiments, the trimerization domain comprises a D4 post-fusion trimerization domain of VSV-G protein. In some embodiments, the trimerization domain comprises a Dengue E protein post-fusion trimerization domain. In some embodiments, the trimerization domain comprises a foldon trimerization domain. In some embodiments, the trimerization domain comprises human C-propeptide of α1(I) collagen. In some embodiments, the oligomerization domain is a tetramerization domain. In some embodiments, the tetramerization domain comprises an influenza neuraminidase stem domain.

TABLE 1

Exemplary Oligomerization Domain Sequences

| Domain | Oligomerization | Amino Acid Sequence | SEQ ID NO: |
|---|---|---|---|
| D4 Variation 1 | Trimer | IGTALQVKMPKSHKAIQADGWMCHASK WVTTCDFRWYGPKYITHSIRSFTPSVEQ CKESIEQTKQGTWLNPGFPPQSCGYATV TDAEAVIVQVTPHHVLVDEYTGEWVDS QFINGKCSNYICPTVHNSTTWHSDYKVK GLCDSNLISMDI | 5 |

TABLE 1-continued

Exemplary Oligomerization Domain Sequences

| Domain | Oligomerization | Amino Acid Sequence | SEQ ID NO: |
|---|---|---|---|
| D4 Variation 2 | Trimer | IQADGWMCHASKWVTTCDFRWYGPKY ITHSIRSFTPSVEQCKESIEQTKQGTWLNP GFPPQSCGYATVTDAEAVIVQVTPHHVL VDEYTGEWVDSQFINGKCSNYICPTVHN STTWHSDYKVKGLCDSNL | 6 |
| D4 Variation 3 | Trimer | IQADGWMCHASKWVTTCDFRWYGPKY ITHSIRSFTPSVEQCKESIEQTKQGTWLNP GFPPQSCGYATVTDAEAVIVQVTPHHVL VDEYTGEWVDSQFINGKCSNYICPTVHN STT | 7 |
| D4 Variation 4 | Trimer | IQADGWMCHASKWVTTCDFRWYGPKY ITHSIRSFTPSVEQCKESIEQTKQGTWLNP GFPPQSCGYATVTDAEAVIVQVTPHHVL VDEYTGEWVDSQFING | 8 |
| D4 Variation 5 | Trimer | IQADGWMCHASKWVTTCDFRWYGPKY ITHSIRSFTPSVEQCKESIEQTKQGTWLNP GFPPQSCGYATVTDAEAVIVQVTPHHVL | 9 |
| Foldon | Trimer | GYIPEAPRDGQAYVRKDGEWVLLSTFL | 10 |
| Leucine Zipper V1 | Dimer | RMKQLEDKVEELLSKQYHLENEVARLK KLVGER | 11 |
| Leucine Zipper V2 | Dimer | RMKQLEDKVEELLSKNYHLENEVARLK KLVGER | 12 |
| Neuraminidase Stem V1 | Tetramer | MNPNQKIITIGSICLVVGLISLILQIGNIISI WISHSIQT | 13 |
| Neuraminidase Stem V2 | Tetramer | MNPNQKIITIGSICMVTGIVSLMLQIGNMI ISIWVSHSIHTGNQHQSEPISNTNFLTEKA VASVKLAGNSSLCPIN | 14 |
| Dengue E Fusion V1 | Trimer | KLCIEAKISNTTTDSRCPTQGEATLVEEQ DTNFVCRRTFVDRGHGNGCGLFGKGSLI TCAKFKCVTKL | 15 |
| Dengue E Fusion V2 | Trimer | IELLKTEVTNPAVLRKLCIEAKISNTTTDS RCPTQGEATLVEEQDTNFVCRRTFVDRG HGNGCGLFGKGSLITCAKFKCVTKL | 16 |
| Dengue E Fusion V3 | Trimer | KLCIEAKISNTTTDSRCPTQGEATLVEEQ DTNFVCRRTFVDRGHGNGCGLFGKGSLI TCAKFKCVTKLEGKIVQYENLKYSVI | 17 |
| Dengue E Fusion V4 | Trimer | EAKISNTTTDSRCPTQGEATLVEEQDTNF VCRRTFVDRGHGNGCGLFGKGSLITCAK FK | 18 |
| human C-propeptide of α1(I) collagen | Trimer | ETGHHHHHHSADEPMDFKINTDEIMTSL KSVNGQIESLISPDGSRKNPARNCRDLKF CHPELKSGEYWVDPNQGCKLDAIKVFC NMETGETCISANPLNVPRKHWWTDSSA EKKHVWFGESMDGGFQFSYGNPELPED VLDVQLAFLRLLSSRASQQITYHCKNSIA YMDQASGNVKKALKLMGSNEGEFKAE GNSKFTYTVLEDGCTKHTGEWSKTVFE YRTRKAVRLPIVDIAPYDIGGPDQEFGV DVGPVCFL | 28 |

In some embodiments, the oligomerization domain comprises an amino acid sequence disclosed in Table 1, or an amino acid sequence that is substantially identical to an amino acid sequence in Table 1 (e.g. 80%, 85%, 90%, 95%, 96%, 97%, 98%, 99% sequence identity). In some instances, the oligomerization domain comprises an amino acid sequence comprising at least a portion having at least or about 10, 20, 30, 40, 50, 60, 70, 80, 90, 100, 110, 120, 130 consecutive amino acid sequences of any sequence according to Table 1. In some embodiments, the oligomerization domain comprises an amino acid sequence that has at least 95% sequence identity to an amino acid sequence according to any one of SEQ ID NOs: 5-18 and 28.

Transmembrane Polypeptides

Described herein, in some embodiments, are multivalent particles comprising a fusion protein that comprises a mammalian polypeptide that binds to a viral protein and a transmembrane polypeptide. In some embodiments, the transmembrane polypeptide comprises the transmembrane domain of a Vesicular Stomatitis virus glycoprotein (VSV-G). In some embodiments, the transmembrane polypeptide comprises the transmembrane domain and cytosolic domain of a Vesicular Stomatitis virus glycoprotein (VSV-G). In some embodiments, the transmembrane polypeptide comprises the transmembrane domain of a Dengue E protein. In some embodiments, the transmembrane polypeptide comprises the transmembrane domain and cytosolic domain of a Dengue E protein. In some embodiments, the transmembrane polypeptide comprises the transmembrane domain of influenza Hemagglutinin (HA). In some embodiments, the transmembrane polypeptide comprises the transmembrane domain and cytosolic domain of influenza Hemagglutinin (HA). In some embodiments, the transmembrane polypeptide comprises the transmembrane domain of HIV surface glycoprotein GP120 or GP41. In some embodiments, the transmembrane polypeptide comprises the transmembrane domain and cytosolic domain of HIV surface glycoprotein GP120 or GP41. In some embodiments, the transmembrane domain comprises the transmembrane polypeptide of measles virus surface glycoprotein hamagglutinin (H) protein. In some embodiments, the transmembrane polypeptide comprises the transmembrane domain and cytosolic domain of measles virus surface glycoprotein hamagglutinin (H) protein. In some embodiments, the transmembrane polypeptide comprises the transmembrane domain of influenza Neuraminidase (NA). In some embodiments, the transmembrane polypeptide comprises the transmembrane domain and cytosolic domain of influenza Neuraminidase (NA).

amino acid sequence in Table 2 (e.g. 80%, 85%, 90%, 95%, 96%, 97%, 98%, 99% sequence identity). In some instances, the transmembrane polypeptide comprises an amino acid sequence comprising at least a portion having at least or about 10, 20, 30, 40, 50, 60, 70, 80, 90, 100, 110, 120, 130 consecutive amino acid sequences of any sequence according to Table 2.

Described herein, in some embodiments, are multivalent particles comprising a fusion protein that comprises a mammalian polypeptide that binds to a viral protein and a transmembrane polypeptide. In some embodiments, the transmembrane polypeptide anchors the fusion protein to a lipid bilayer of the multivalent particle. In some embodiments, the transmembrane polypeptide comprises a spike glycoprotein, a mammalian membrane protein, an envelope protein, a nucleocapsid protein, or a cellular transmembrane protein. In some embodiments, the transmembrane polypeptide comprises the transmembrane domain of VSVG, spike protein S1, spike protein S2, Sindbis virus envelope (SINDBIS) protein, hemagglutinin envelope protein from measles virus, envelope glycoprotein of measles virus fusion (F) protein, RD114, BaEV, GP41, or GP120. In some embodiments, the transmembrane polypeptide comprises VSVG transmembrane region. In some embodiments, the VSVG transmembrane region comprises full length VSVG transmembrane region or a truncated VSVG transmembrane region. In some embodiments, the transmembrane polypeptide comprises a VSVG transmembrane region and a VSVG cytoplasmic tail. In some embodiments, the hemagglutinin

TABLE 2

Exemplary Transmembrane Polypeptide Sequences

| Domain | Amino Acid Sequence | SEQ ID NO: |
|---|---|---|
| VSV-G Transmembrane (TM) V1 | IASFFFIIGLIIGLFLVLRVGI | 19 |
| VSV-G Transmembrane (TM) V2 | PIELVEGWFSSWKSSIASFFFIIGLIIGLFL VLRVGI | 20 |
| VSV-G Transmembrane (TM) V3 | DDESLFFGDTGLSKNPIELVEGWFSSWK SSIASFFFIIGLIIGLFLVLRVGIH | 21 |
| VSV-G Transmembrane (TM) V4 | GMLDSDLHLSSKAQVFEHPHIQDAASQL PDDESLFFGDTGLSKNPIELVEGWFSSW KSSIASFFFIIGLIIGLFLVLRVGI | 22 |
| VSV-G Cytosolic Tail (CT) | HLCIKLKHTKKRQIYTDIEMNRLGK | 23 |
| Influenza Neuraminidase TM (N1) | IITIGSVCMTIGMANLILQIGNI | 24 |
| Influenza Hemagglutinin TM (H1) | LAIYSTVASSLVLVVSLGAISFW | 25 |
| Dengue E Protein TM | AYGVLFSGVSWTMKIGIGILLTWLGLNS RSTSLSMTCIAVGMVTLYLGVMVQ | 26 |
| HIV gp TM | FIMIVGGLVGLRIVFAVLSIV | 27 |

In some embodiments, the transmembrane polypeptide comprises an amino acid sequence disclosed in Table 2, or an amino acid sequence that is substantially identical to an envelope protein from measles virus is a variant of the hemagglutinin envelope protein from measles virus. In some instances, the variant is HCΔ18.

In some embodiments, the transmembrane polypeptide comprises an amino acid sequence of at least 75% sequence identity to an amino acid sequence according to SEQ ID NO: 3. In some embodiments, the transmembrane polypeptide comprises an amino acid sequence of at least 80% sequence identity to an amino acid sequence according to SEQ ID NO: 3. In some embodiments, the transmembrane polypeptide comprises an amino acid sequence of at least 85% sequence identity to an amino acid sequence according to SEQ ID NO: 3. In some embodiments, the transmembrane polypeptide comprises an amino acid sequence of at least 90% sequence identity to an amino acid sequence according to SEQ ID NO: 3. In some embodiments, the transmembrane polypeptide comprises an amino acid sequence of at least 95% sequence identity to an amino acid sequence according to SEQ ID NO: 3. In some embodiments, the transmembrane polypeptide comprises an amino acid sequence of at least 98% sequence identity to an amino acid sequence according to SEQ ID NO: 3. In some embodiments, the transmembrane polypeptide comprises an amino acid sequence of at least 99% sequence identity to an amino acid sequence according to SEQ ID NO: 3.

In some embodiments, the transmembrane polypeptide comprises an amino acid sequence of at least 75% sequence homology to an amino acid sequence according to SEQ ID NO: 3. In some embodiments, the transmembrane polypeptide comprises an amino acid sequence of at least 80% sequence homology to an amino acid sequence according to SEQ ID NO: 3. In some embodiments, the transmembrane polypeptide comprises an amino acid sequence of at least 85% sequence homology to an amino acid sequence according to SEQ ID NO: 3. In some embodiments, the transmembrane polypeptide comprises an amino acid sequence of at least 90% sequence homology to an amino acid sequence according to SEQ ID NO: 3. In some embodiments, the transmembrane polypeptide comprises an amino acid sequence of at least 95% sequence homology to an amino acid sequence according to SEQ ID NO: 3. In some embodiments, the transmembrane polypeptide comprises an amino acid sequence of at least 98% sequence homology to an amino acid sequence according to SEQ ID NO: 3. In some embodiments, the transmembrane polypeptide comprises an amino acid sequence of at least 99% sequence homology to an amino acid sequence according to SEQ ID NO: 3.

In some instances, the transmembrane polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or more than 490 consecutive amino acids of SEQ ID NO: 3.

In some embodiments, the transmembrane polypeptide comprises an amino acid sequence of at least 75% sequence identity to an amino acid sequence according to SEQ ID NO: 4. In some embodiments, the transmembrane polypeptide comprises an amino acid sequence of at least 80% sequence identity to an amino acid sequence according to SEQ ID NO: 4. In some embodiments, the transmembrane polypeptide comprises an amino acid sequence of at least 85% sequence identity to an amino acid sequence according to SEQ ID NO: 4. In some embodiments, the transmembrane polypeptide comprises an amino acid sequence of at least 90% sequence identity to an amino acid sequence according to SEQ ID NO: 4. In some embodiments, the transmembrane polypeptide comprises an amino acid sequence of at least 95% sequence identity to an amino acid sequence according to SEQ ID NO: 4. In some embodiments, the transmembrane polypeptide comprises an amino acid sequence of at least 98% sequence identity to an amino acid sequence according to SEQ ID NO: 4. In some embodiments, the transmembrane polypeptide comprises an amino acid sequence of at least 99% sequence identity to an amino acid sequence according to SEQ ID NO: 4.

In some embodiments, the transmembrane polypeptide comprises an amino acid sequence of at least 75% sequence homology to an amino acid sequence according to SEQ ID NO: 4. In some embodiments, the transmembrane polypeptide comprises an amino acid sequence of at least 80% sequence homology to an amino acid sequence according to SEQ ID NO: 4. In some embodiments, the transmembrane polypeptide comprises an amino acid sequence of at least 85% sequence homology to an amino acid sequence according to SEQ ID NO: 4. In some embodiments, the transmembrane polypeptide comprises an amino acid sequence of at least 90% sequence homology to an amino acid sequence according to SEQ ID NO: 4. In some embodiments, the transmembrane polypeptide comprises an amino acid sequence of at least 95% sequence homology to an amino acid sequence according to SEQ ID NO: 4. In some embodiments, the transmembrane polypeptide comprises an amino acid sequence of at least 98% sequence homology to an amino acid sequence according to SEQ ID NO: 4. In some embodiments, the transmembrane polypeptide comprises an amino acid sequence of at least 99% sequence homology to an amino acid sequence according to SEQ ID NO: 4.

In some instances, the transmembrane polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 800, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, or more than 1250 consecutive amino acids of SEQ ID NO: 4.

Described herein, in some embodiments, are multivalent particles comprising a fusion protein that comprises a mammalian polypeptide that binds to a viral protein and a transmembrane polypeptide, wherein the multivalent particles further comprises a second fusion protein that comprises a second mammalian polypeptide that binds to the viral protein and a second transmembrane polypeptide. In some embodiments, the second transmembrane polypeptide comprises the transmembrane region of a spike glycoprotein, a mammalian membrane protein, an envelope protein, a nucleocapsid protein, or a cellular transmembrane protein. In some embodiments, the second transmembrane polypeptide comprises the transmembrane region of VSVG, spike protein S1, spike protein S2, Sindbis virus envelope (SINDBIS) protein, hemagglutinin envelope protein from measles virus, envelope glycoprotein of measles virus fusion (F) protein, RD114, BaEV, GP41, or GP120. In some embodiments, the second transmembrane polypeptide comprises VSVG transmembrane region. In some embodiments, the VSVG transmembrane region comprises full length VSVG transmembrane region or a truncated VSVG transmembrane region. In some embodiments, the transmembrane polypeptide comprises a VSVG transmembrane region and a VSVG cytoplasmic tail. In some embodiments, the hemagglutinin envelope protein from measles virus is a variant of the hemagglutinin envelope protein from measles virus. In some instances, the variant is HCΔ18.

In some embodiments, the second transmembrane polypeptide comprises an amino acid sequence of at least 75% sequence identity to an amino acid sequence according to SEQ ID NO: 3. In some embodiments, the second transmembrane polypeptide comprises an amino acid sequence of at least 80% sequence identity to an amino acid sequence according to SEQ ID NO: 3. In some embodiments, the second transmembrane polypeptide comprises an amino acid sequence of at least 85% sequence identity to an amino acid sequence according to SEQ ID NO: 3. In some embodiments, the second transmembrane polypeptide comprises an amino acid sequence of at least 90% sequence identity to an amino acid sequence according to SEQ ID NO: 3. In some embodiments, the second transmembrane polypeptide comprises an amino acid sequence of at least 95% sequence identity to an amino acid sequence according to SEQ ID NO: 3. In some embodiments, the second transmembrane polypeptide comprises an amino acid sequence of at least 98% sequence identity to an amino acid sequence according to SEQ ID NO: 3. In some embodiments, the second transmembrane polypeptide comprises an amino acid sequence of at least 99% sequence identity to an amino acid sequence according to SEQ ID NO: 3.

In some embodiments, the second transmembrane polypeptide comprises an amino acid sequence of at least 75% sequence homology to an amino acid sequence according to SEQ ID NO: 3. In some embodiments, the second transmembrane polypeptide comprises an amino acid sequence of at least 80% sequence homology to an amino acid sequence according to SEQ ID NO: 3. In some embodiments, the second transmembrane polypeptide comprises an amino acid sequence of at least 85% sequence homology to an amino acid sequence according to SEQ ID NO: 3. In some embodiments, the second transmembrane polypeptide comprises an amino acid sequence of at least 90% sequence homology to an amino acid sequence according to SEQ ID NO: 3. In some embodiments, the second transmembrane polypeptide comprises an amino acid sequence of at least 95% sequence homology to an amino acid sequence according to SEQ ID NO: 3. In some embodiments, the second transmembrane polypeptide comprises an amino acid sequence of at least 98% sequence homology to an amino acid sequence according to SEQ ID NO: 3. In some embodiments, the second transmembrane polypeptide comprises an amino acid sequence of at least 99% sequence homology to an amino acid sequence according to SEQ ID NO: 3.

In some instances, the second transmembrane polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or more than 490 consecutive amino acids of SEQ ID NO: 3.

In some embodiments, the second transmembrane polypeptide comprises an amino acid sequence of at least 75% sequence identity to an amino acid sequence according to SEQ ID NO: 4. In some embodiments, the second transmembrane polypeptide comprises an amino acid sequence of at least 80% sequence identity to an amino acid sequence according to SEQ ID NO: 4. In some embodiments, the second transmembrane polypeptide comprises an amino acid sequence of at least 85% sequence identity to an amino acid sequence according to SEQ ID NO: 4. In some embodiments, the second transmembrane polypeptide comprises an amino acid sequence of at least 90% sequence identity to an amino acid sequence according to SEQ ID NO: 4. In some embodiments, the second transmembrane polypeptide comprises an amino acid sequence of at least 95% sequence identity to an amino acid sequence according to SEQ ID NO: 4. In some embodiments, the second transmembrane polypeptide comprises an amino acid sequence of at least 98% sequence identity to an amino acid sequence according to SEQ ID NO: 4. In some embodiments, the second transmembrane polypeptide comprises an amino acid sequence of at least 99% sequence identity to an amino acid sequence according to SEQ ID NO: 4.

In some embodiments, the second transmembrane polypeptide comprises an amino acid sequence of at least 75% sequence homology to an amino acid sequence according to SEQ ID NO: 4. In some embodiments, the second transmembrane polypeptide comprises an amino acid sequence of at least 80% sequence homology to an amino acid sequence according to SEQ ID NO: 4. In some embodiments, the second transmembrane polypeptide comprises an amino acid sequence of at least 85% sequence homology to an amino acid sequence according to SEQ ID NO: 4. In some embodiments, the second transmembrane polypeptide comprises an amino acid sequence of at least 90% sequence homology to an amino acid sequence according to SEQ ID NO: 4. In some embodiments, the second transmembrane polypeptide comprises an amino acid sequence of at least 95% sequence homology to an amino acid sequence according to SEQ ID NO: 4. In some embodiments, the second transmembrane polypeptide comprises an amino acid sequence of at least 98% sequence homology to an amino acid sequence according to SEQ ID NO: 4. In some embodiments, the second transmembrane polypeptide comprises an amino acid sequence of at least 99% sequence homology to an amino acid sequence according to SEQ ID NO: 4.

In some instances, the second transmembrane polypeptide comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 800, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, or more than 1250 consecutive amino acids of SEQ ID NO: 4.

Mammalian Polypeptide and Transmembrane Polypeptide Combinations

Described herein, in some embodiments, are multivalent particles comprising a fusion protein that comprises a mammalian polypeptide that binds to a viral protein and a transmembrane polypeptide. In some embodiments, the mammalian polypeptide is a Type I receptor. In some embodiments, the mammalian polypeptide is a Type II receptor.

In some embodiments, the mammalian polypeptide comprises ACE2, TRMPSS2, DPP4, CD4, CCR5, CXCR4, CD209, or CLEC4M and the transmembrane polypeptide comprises the transmembrane region of VSVG, spike protein 51, spike protein S2, Sindbis virus envelope (SINDBIS) protein, hemagglutinin envelope protein from measles virus, envelope glycoprotein of measles virus fusion (F) protein, RD114, BaEV, GP41, or GP120.

In some embodiments, the mammalian polypeptide comprises ACE2 and the transmembrane polypeptide comprises VSVG transmembrane region. In some embodiments, the mammalian polypeptide comprises ACE2 and the transmembrane polypeptide comprises spike protein S1 transmembrane region. In some embodiments, the mammalian polypeptide comprises ACE2 and the transmembrane polypeptide comprises spike protein S2 transmembrane region. In some embodiments, the mammalian polypeptide comprises ACE2 and the transmembrane polypeptide comprises the transmembrane region of a surface glycoprotein of an enveloped virus. In some embodiments, the mammalian polypeptide comprises ACE2 and the transmembrane polypeptide comprises the transmembrane region of Sindbis virus envelope (SINDBIS) protein. In some embodiments, the mammalian polypeptide comprises ACE2 and the transmembrane polypeptide comprises BaEV transmembrane region. In some embodiments, the mammalian polypeptide comprises ACE2 and the transmembrane polypeptide comprises GP41 transmembrane region. In some embodiments, the mammalian polypeptide comprises ACE2 and the transmembrane polypeptide comprises GP120 transmembrane region.

In some embodiments, the mammalian polypeptide comprises CD4 and the transmembrane polypeptide comprises VSVG transmembrane region. In some embodiments, the mammalian polypeptide comprises CD4 and the transmembrane polypeptide comprises spike protein S1 transmembrane region. In some embodiments, the mammalian polypeptide comprises CD4 and the transmembrane polypeptide comprises spike protein S2 transmembrane region. In some embodiments, the mammalian polypeptide comprises CD4 and the transmembrane polypeptide comprises the transmembrane region of a surface glycoprotein of an enveloped virus. In some embodiments, the mammalian polypeptide comprises CD4 and the transmembrane polypeptide comprises Sindbis virus envelope (SINDBIS) protein transmembrane region. In some embodiments, the mammalian polypeptide comprises CD4 and the transmembrane polypeptide comprises BaEV transmembrane region. In some embodiments, the mammalian polypeptide comprises CD4 and the transmembrane polypeptide comprises GP41 transmembrane region. In some embodiments, the mammalian polypeptide comprises CD4 and the transmembrane polypeptide comprises GP120 transmembrane region.

In some embodiments, the mammalian polypeptide comprises DPP4 and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the mammalian polypeptide comprises DPP4 and the transmembrane polypeptide comprises envelope glycoprotein of measles virus fusion (F) protein.

In some embodiments, the mammalian polypeptide comprises TRMPSS2 and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the mammalian polypeptide comprises TRMPSS2 and the transmembrane polypeptide comprises envelope glycoprotein of measles virus fusion (F) protein.

In some embodiments, the mammalian polypeptide comprises CD209 and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the mammalian polypeptide comprises CD209 and the transmembrane polypeptide comprises envelope glycoprotein of measles virus fusion (F) protein.

In some embodiments, the mammalian polypeptide comprises CLEC4M and the transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the mammalian polypeptide comprises CLEC4M and the transmembrane polypeptide comprises envelope glycoprotein of measles virus fusion (F) protein.

Described herein, in some embodiments, are multivalent particles comprising a fusion protein that comprises a mammalian polypeptide that binds to a viral protein and a transmembrane polypeptide, wherein the multivalent particles further comprise a second mammalian polypeptide and second transmembrane polypeptide. In some embodiments, the second mammalian polypeptide is a Type I receptor. In some embodiments, the second mammalian polypeptide is a Type II receptor.

In some embodiments, the second mammalian polypeptide comprises ACE2, TRMPSS2, DPP4, CD4, CCR5, CXCR4, CD209, or CLEC4M and the second transmembrane polypeptide comprises the transmembrane region of VSVG, spike protein S1, spike protein S2, Sindbis virus envelope (SINDBIS) protein, hemagglutinin envelope protein from measles virus, envelope glycoprotein of measles virus fusion (F) protein, RD114, BaEV, GP41, or GP120.

In some embodiments, the second mammalian polypeptide comprises ACE2 and the second transmembrane polypeptide comprises VSVG transmembrane region. In some embodiments, the second mammalian polypeptide comprises ACE2 and the second transmembrane polypeptide comprises spike protein S1 transmembrane region. In some embodiments, the second mammalian polypeptide comprises ACE2 and the second transmembrane polypeptide comprises spike protein S2 transmembrane region. In some embodiments, the second mammalian polypeptide comprises ACE2 and the second transmembrane polypeptide comprises the transmembrane region of a surface glycoprotein of an enveloped virus. In some embodiments, the second mammalian polypeptide comprises ACE2 and the second transmembrane polypeptide comprises Sindbis virus envelope (SINDBIS) protein transmembrane region. In some embodiments, the second mammalian polypeptide comprises ACE2 and the second transmembrane polypeptide comprises BaEV transmembrane region. In some embodiments, the second mammalian polypeptide comprises ACE2 and the second transmembrane polypeptide comprises GP41 transmembrane region. In some embodiments, the second mammalian polypeptide comprises ACE2 and the second transmembrane polypeptide comprises GP120 transmembrane region.

In some embodiments, the second mammalian polypeptide comprises CD4 and the second transmembrane polypeptide comprises VSVG transmembrane region. In some embodiments, the second mammalian polypeptide comprises CD4 and the second transmembrane polypeptide comprises spike protein S1 transmembrane region. In some embodiments, the second mammalian polypeptide comprises CD4 and the second transmembrane polypeptide comprises spike protein S2 transmembrane region. In some embodiments, the second mammalian polypeptide comprises CD4 and the second transmembrane polypeptide comprises the transmembrane region of a surface glycoprotein of an enveloped virus. In some embodiments, the second mammalian polypeptide comprises CD4 and the second transmembrane polypeptide comprises Sindbis virus envelope (SINDBIS) protein transmembrane region. In some embodiments, the second mammalian polypeptide comprises CD4 and the second transmembrane polypeptide comprises BaEV transmembrane region. In some embodiments, the second mammalian polypeptide comprises CD4 and the second transmembrane polypeptide comprises GP41 transmembrane region. In some embodiments, the second mammalian polypeptide comprises CD4 and the second transmembrane polypeptide comprises GP120 transmembrane region.

In some embodiments, the second mammalian polypeptide comprises DPP4 and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the second mammalian polypeptide comprises DPP4 and the second transmembrane polypeptide comprises envelope glycoprotein of measles virus fusion (F) protein.

In some embodiments, the second mammalian polypeptide comprises TRMPSS2 and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the second mammalian polypeptide comprises TRMPSS2 and the second transmembrane polypeptide comprises envelope glycoprotein of measles virus fusion (F) protein.

In some embodiments, the second mammalian polypeptide comprises CD209 and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the second mammalian polypeptide comprises CD209 and the second transmembrane polypeptide comprises envelope glycoprotein of measles virus fusion (F) protein.

In some embodiments, the second mammalian polypeptide comprises CLEC4M and the second transmembrane polypeptide comprises hemagglutinin envelope protein from measles virus. In some embodiments, the hemagglutinin envelope protein from measles virus is a variant of the hemagglutinin envelope protein from measles virus. In some embodiments, the variant is HCΔ18. In some embodiments, the second mammalian polypeptide comprises CLEC4M and the second transmembrane polypeptide comprises envelope glycoprotein of measles virus fusion (F) protein.

In some embodiments, the mammalian polypeptide comprises ACE2, the transmembrane polypeptide comprises VSVG transmembrane region, spike protein S2 transmembrane region, or a surface glycoprotein of an enveloped virus, the second mammalian polypeptide comprises a heparan sulfate proteoglycan, and the second transmembrane polypeptide comprises VSVG transmembrane region, spike protein S2 transmembrane region, or a surface glycoprotein of an enveloped virus. In some embodiments, the mammalian polypeptide comprises CD4 and the second mammalian peptide comprises, CCR5, CXCR4, or both.

Described herein, in some embodiments, are multivalent particles comprising a fusion protein that comprises a mammalian polypeptide that binds to a viral protein and a transmembrane polypeptide, wherein the multivalent particles further comprise, wherein the multivalent particles further comprise an oligomerization domain.

In some embodiments, the oligomerization domain is a dimerization domain. In some embodiments, the dimerization domain comprises a leucine zipper dimerization domain. In some embodiments, the oligomerization domain is a trimerization domain. In some embodiments, the trimerization domain comprises a post-fusion oligomerization domain of viral surface protein. In some embodiments, the trimerization domain comprises a D4 post-fusion trimerization domain of VSV-G protein. In some embodiments, the trimerization domain comprises a Dengue E protein post-fusion trimerization domain. In some embodiments, the trimerization domain comprises a foldon trimerization domain. In some embodiments, the trimerization domain comprises human C-propeptide of α1(I) collagen. In some embodiments, the oligomerization domain is a tetramerization domain. In some embodiments, the tetramerization domain comprises an influenza neuraminidase stem domain.

In some embodiments, when the fusion protein is expressed on the surface of the multivalent particle, the oligomerization domain is outside of the multivalent particle. In some embodiments, when the fusion protein is expressed on the surface of the multivalent particle, the oligomerization domain is outside of the multivalent particle and adjacent to a signal peptide. In some embodiments, when the fusion protein is expressed on the surface of the multivalent particle, the oligomerization domain is outside of the multivalent particle and adjacent to the transmembrane domain. In some embodiments, when the fusion protein is expressed on the surface of the multivalent particle, the oligomerization domain is inside of the multivalent particle. In some embodiments, when the fusion protein is expressed on the surface of the multivalent particle, the oligomerization domain is inside of the multivalent particle and adjacent to the transmembrane polypeptide.

In some embodiments, the fusion protein comprises a signal peptide.

In some embodiments, domains of the fusion protein are arranged from the N-terminus to the C-terminus in the following orders: (a) signal peptide, mammalian polypeptide, oligomerization domain, transmembrane polypeptide, and cytosolic domain; (b) signal peptide, mammalian polypeptide, transmembrane polypeptide, oligomerization domain, and cytosolic domain; or (c) signal peptide, oligomerization domain, mammalian polypeptide, transmembrane polypeptide, and cytosolic domain. In some embodiments, domains of the fusion protein are arranged from the N-terminus to the C-terminus in the following order: signal peptide, mammalian polypeptide, oligomerization domain, transmembrane polypeptide, and cytosolic domain. In some embodiments, domains of the fusion protein are arranged from the N-terminus to the C-terminus in the following order: signal peptide, mammalian polypeptide, transmembrane polypeptide, oligomerization domain, and cytosolic domain. In some embodiments, domains of the fusion protein are arranged from the N-terminus to the C-terminus in the following order: signal peptide, oligomerization domain, mammalian polypeptide, transmembrane polypeptide, and cytosolic domain.

Disclosed herein are fusion proteins comprising a transmembrane polypeptide, a cytosolic domain, a mammalian polypeptide, and an oligomerization domain wherein when the fusion protein is expressed on the surface of a multivalent particle, the fusion protein is displayed in an oligomeric format.

TABLE 3

Exemplary Fusion Protein Sequences

| Fusion Protein | Amino Acid Sequence | SEQ ID NO: |
| --- | --- | --- |
| ACE2 fused with VSVG transmembrane domain (VGTM) | MSSSSWLLLSLVAVTAAQSTIEEQAKTFLDKFNHEAED LFYQSSLASWNYNTNITEENVQNIVINNAGDKWSAFLK EQSTLAQMYPLQEIQNLTVKLQLQALQQNGSSVLSED KSKRLNTILNTMSTIYSTGKVCNPDNPQECLLLEPGLNE IMANSLDYNERLWAWESWRSEVGKQLRPLYEEYVVL KNEMARANHYEDYGDYWRGDYEVNGVDGYDYSRGQ LIEDVEHTFEEIKPLYEHLHAYVRAKLMNAYPSYISPIG CL TABLE 3-continued Exemplary Fusion Protein Sequences

| Fusion Protein | Amino Acid Sequence | SEQ ID NO: |
|---|---|---|
| | ADSESGGHITHSGMVGMGVSCTVTREGGGSKGTDDAT<br>ADSRKTYTLTDYLKNTYRLKLYSLRWISDHEYLYKQE<br>NNILVFNAEYGNSSVFLENSTFDEFGHSINDYSISPDGQ<br>FILLEYNYVKQWRHSYTASYDIYDLNKRQLITEERIPNN<br>TQWVTWSPVGHKLAYVWNNDIYVKIEPNLPSYRITWT<br>GKEDIIYNGITDWVYEEEVFSAYSALWWSPNGTFLAY<br>AQFNDTEVPLIEYSFYSDESLQYPKTVRVPYPKAGAVN<br>PTVKFFVVNTDSLSSVTNATSIQITAPASMLIGDHYLCD<br>VTWATQERISLQWLRRIQNYSVMDICDYDESSGRWNC<br>LVARQHIEMSTTGWVGRFRPSEPHFTLDGNSFYKIISNE<br>EGYRHICYFQIDKKDCTFITKGTWEVIGIEALTSDYLYY<br>ISNEYKGMPGGRNLYKIQLSDYTKVTCLSCELNPERCQ<br>YYSVSFSKEAKYYQLRCSGPGLPLYTLHSSVNDKGLRV<br>LEDNSALDKMLQNVQMPSKKLDFIILNETKFWYQMILP<br>PHFDKSKKYPLLLDVYAGPCSQKADTVFRLNWATYLA<br>STENIIVASFDGRGSGYQGDKIMHAINRRLGTFEVEDQI<br>EAARQFSKMGFVDNKRIAIWGWSYGGYVTSMVLGSG<br>SGVFKCGIAVAPVSRWEYYDSVYTERYMGLPTPEDNL<br>DHYRNSTVMSRAENFKQVEYLLIHGTADDNVHFQQSA<br>QISKALVDVGVDFQAMWYTDEDHGIASSTAHQHIYTH<br>MSHFIKQCFSLPAAARGSGLNDIFEAQKIEWHE | |
| NA75-DPP4 | KGTDDATADSRKTYTLTDYLKNTYRLKLYSLRWISDH<br>EYLYKQENNILVFNAEYGNSSVFLENSTFDEFGHSIND<br>YSISPDGQFILLEYNYVKQWRHSYTASYDIYDLNKRQL<br>ITEERIPNNTQWVTWSPVGHKLAYVWNNDIYVKIEPNL<br>PSYRITWTGKEDIIYNGITDWVYEEEVFSAYSALWWSP<br>NGTFLAYAQFNDTEVPLIEYSFYSDESLQYPKTVRVPY<br>PKAGAVNPTVKFFVVNTDSLSSVTNATSIQITAPASMLI<br>GDHYLCDVTWATQERISLQWLRRIQNYSVMDICDYDE<br>SSGRWNCLVARQHIEMSTTGWVGRFRPSEPHFTLDGN<br>SFYKIISNEEGYRHICYFQIDKKDCTFITKGTWEVIGIEA<br>LTSDYLYYISNEYKGMPGGRNLYKIQLSDYTKVTCLSC<br>ELNPERCQYYSVSFSKEAKYYQLRCSGPGLPLYTLHSS<br>VNDKGLRVLEDNSALDKMLQNVQMPSKKLDFIILNET<br>KFWYQMILPPHFDKSKKYPLLLDVYAGPCSQKADTVF<br>RLNWATYLASTENIIVASFDGRGSGYQGDKIMHAINRR<br>LGTFEVEDQIEAARQFSKMGFVDNKRIAIWGWSYGGY<br>VTSMVLGSGSGVFKCGIAVAPVSRWEYYDSVYTERYM<br>GLPTPEDNLDHYRNSTVMSRAENFKQVEYLLIHGTAD<br>DNVHFQQSAQISKALVDVGVDFQAMWYTDEDHGIASS<br>TAHQHIYTHMSHFIKQCFSLP | 32 |
| H374A and<br>H378A<br>(H2A/ACE2-<br>VGTM | MSSSSWLLLSLVAVTAAQSTIEEQAKTFLDKFNHEAED<br>LFYQSSLASWNYNTNITEENVQNIVINNAGDKWSAFLK<br>EQSTLAQMYPLQEIQNLTVKLQLQALQQNGSSVLSED<br>KSKRLNTILNTMSTIYSTGKVCNPDNPQECLLLEPGLNE<br>IMANSLDYNERLWAWESWRSEVGKQLRPLYEEYVVL<br>KNEMARANHYEDYGDYWRGDYEVNGVDGYDYSRGQ<br>LIEDVEHTFEEIKPLYEHLHAYVRAKLMNAYPSYISPIG<br>CLPAHLLGDMWGRFWTNLYSLTVPFGQKPNIDVTDA<br>MVDQAWDAQRIFKEAEKFFVSVGLPNMTQGFWENSM<br>LTDPGNVQKAVCHPTAWDLGKGDFRILMCTKVTMDD<br>FLTAHAEMGAIQYDMAYAAQPFLLRNGANEGFHEAV<br>GEIMSLSAATPKHLKSIGLLSPDFQEDNETEINFLLKQA<br>LTIVGTLPFTYMLEKWRWMVFKGEIPKDQWMKKWW<br>EMKREIVGVVEPVPHDETYCDPASLFHVSNDYSFIRYY<br>TRTLYQFQFQEALCQAAKHEGPLHKCDISNSTEAGQKL<br>FNMLRLGKSEPWTLALENVVGAKNMNVRPLLNYFEPL<br>FTWLKDQNKNSFVGWSTDWSPYADQSIKVRISLKSAL<br>GDKAYEWNDNEMYLFRSSVAYAMRQYFLKVKNQMIL<br>FGEEDVRVANLKPRISENPFVTAPKNVSDIIPRTEVEKAI<br>RMSRSRINDAFRLNDNSLEFLGIQPTLGPPNQPPVSSRG<br>MLDSDLHLSSKAQVFEHPHIQDAASQLPDDESLFFGDT<br>GLSKNPIELVEGWFSSWKSSIASFFFIIGLIIGLFLVLRVG<br>IHLCIKLKHTKKRQIYTDIEMNRLGK | 33 |
| WT/ACE2-<br>D4VG | MSSSSWLLLSLVAVTAAQSTIEEQAKTFLDKFNHEAED<br>LFYQSSLASWNYNTNITEENVQNMNNAGDKWSAFLK<br>EQSTLAQMYPLQEIQNLTVKLQLQALQQNGSSVLSED<br>KSKRLNTILNTMSTIYSTGKVCNPDNPQECLLLEPGLNE<br>IMANSLDYNERLWAWESWRSEVGKQLRPLYEEYVVL<br>KNEMARANHYEDYGDYWRGDYEVNGVDGYDYSRGQ<br>LIEDVEHTFEEIKPLYEHLHAYVRAKLMNAYPSYISPIG<br>CLPAHLLGDMWGRFWTNLYSLTVPFGQKPNIDVTDA<br>MVDQAWDAQRIFKEAEKFFVSVGLPNMTQGFWENSM | 34 |

TABLE 3-continued

Exemplary Fusion Protein Sequences

| Fusion Protein | Amino Acid Sequence | SEQ ID NO: |
|---|---|---|
| | LTDPGNVQKAVCHPTAWDLGKGDFRILMCTKVTMDD<br>FLTAHHEMGHIQYDMAYAAQPFLLRNGANEGFHEAV<br>GEIMSLSAATPKHLKSIGLLSPDFQEDNETEINFLLKQA<br>LTIVGTLPFTYMLEKWRWMVFKGEIPKDQWMKKWW<br>EMKREIVGVVEPVPHDETYCDPASLFHVSNDYSFIRYY<br>TRTLYQFQFQEALCQAAKHEGPLHKCDISNSTEAGQKL<br>FNMLRLGKSEPWTLALENVVGAKNMNVRPLLNYFEPL<br>FTWLKDQNKNSFVGWSTDWSPYADQSIKVRISLKSAL<br>GDKAYEWNDNEMYLFRSSVAYAMRQYFLKVKNQMIL<br>FGEEDVRVANLKPRISENFFVTAPKNVSDIIPRTEVEKAI<br>RMSRSRINDAFRLNDNSLEFLGIQPTLGPPNQPPVSSRIQ<br>ADGWMCHASKWVTTCDFRWYGPKYITHSIRSFTPSVE<br>QCKESIEQTKQGTWLNPGFPPQSCGYATVTDAEAVIVQ<br>VTPHHVLVDEYTGEWVDSQFINGKCSNYICPTVHNSTT<br>WHSDYKVKGLCDSNLGMLDSDLHLSSKAQVFEHPHIQ<br>DAASQLPDDESLFFGDTGLSKNPIELVEGWFSSWKSSIA<br>SEFFIIGLIIGLELVLRVGIHLCIKLKHTKKRQIYTDIEMN<br>RLGK | |
| H2A/ACE2-<br>D4VG | MSSSSWLLLSLVAVTAAQSTIEEQAKTFLDKENHEAED<br>LFYQSSLASWNYNTNITEENVQNMNNAGDKWSAFLK<br>EQSTLAQMYPLQEIQNLTVKLQLQALQQNGSSVLSED<br>KSKRLNTILNTMSTIYSTGKVCNPDNPQECLLLEPGLNE<br>IMANSLDYNERLWAWESWRSEVGKQLRPLYEEYVVL<br>KNEMARANHYEDYGDYWRGDYEVNGVDGYDYSRGQ<br>LIEDVEHTFEEIKPLYEHLHAYVRAKLMNAYPSYISPIG<br>CLPAHLLGDMWGRFWTNLYSLTVPFGQKPNIDVTDA<br>MVDQAWDAQRIFKEAEKFFVSVGLPNMTQGFWENSM<br>LTDPGNVQKAVCHPTAWDLGKGDFRILMCTKVTMDD<br>FLTAHAEMGAIQYDMAYAAQPFLLRNGANEGFHEAV<br>GEIMSLSAATPKHLKSIGLLSPDFQEDNETEINFLLKQA<br>LTIVGTLPFTYMLEKWRWMVFKGEIPKDQWMKKWW<br>EMKREIVGVVEPVPHDETYCDPASLFHVSNDYSFIRYY<br>TRTLYQFQFQEALCQAAKHEGPLHKCDISNSTEAGQKL<br>FNMLRLGKSEPWTLALENVVGAKNMNVRPLLNYFEPL<br>FTWLKDQNKNSFVGWSTDWSPYADQSIKVRISLKSAL<br>GDKAYEWNDNEMYLFRSSVAYAMRQYFLKVKNQMIL<br>FGEEDVRVANLKPRISENFFVTAPKNVSDIIPRTEVEKAI<br>RMSRSRINDAFRLNDNSLEFLGIQPTLGPPNQPPVSSRIQ<br>ADGWMCHASKWVTTCDFRWYGPKYITHSIRSFTPSVE<br>QCKESIEQTKQGTWLNPGFPPQSCGYATVTDAEAVIVQ<br>VTPHHVLVDEYTGEWVDSQFINGKCSNYICPTVHNSTT<br>WHSDYKVKGLCDSNLGMLDSDLHLSSKAQVFEHPHIQ<br>DAASQLPDDESLFFGDTGLSKNPIELVEGWFSSWKSSIA<br>SFFFIIGLIIGLELVLRVGIHLCIKLKHTKKRQIYTDIEMN<br>RLGK | 35 |

In some embodiments, the fusion protein or second fusion protein comprises an amino acid sequence of at least 75% sequence identity to an amino acid sequence according to SEQ ID NO: 29. In some embodiments, the fusion protein or second fusion protein comprises an amino acid sequence of at least 80% sequence identity to an amino acid sequence according to SEQ ID NO: 29. In some embodiments, the fusion protein or second fusion protein comprises an amino acid sequence of at least 85% sequence identity to an amino acid sequence according to SEQ ID NO: 29. In some embodiments, the fusion protein or second fusion protein comprises an amino acid sequence of at least 90% sequence identity to an amino acid sequence according to SEQ ID NO: 29. In some embodiments, the fusion protein or second fusion protein comprises an amino acid sequence of at least 95% sequence identity to an amino acid sequence according to SEQ ID NO: 29. In some embodiments, the fusion protein or second fusion protein comprises an amino acid sequence of at least 98% sequence identity to an amino acid sequence according to SEQ ID NO: 29. In some embodiments, the fusion protein or second fusion protein comprises an amino acid sequence of at least 99% sequence identity to an amino acid sequence according to SEQ ID NO: 29.

In some embodiments, the fusion protein or second fusion protein comprises an amino acid sequence of at least 75% sequence homology to an amino acid sequence according to SEQ ID NO: 29. In some embodiments, the fusion protein or second fusion protein comprises an amino acid sequence of at least 80% sequence homology to an amino acid sequence according to SEQ ID NO: 29. In some embodiments, the fusion protein or second fusion protein comprises an amino acid sequence of at least 85% sequence homology to an amino acid sequence according to SEQ ID NO: 29. In some embodiments, the fusion protein or second fusion protein comprises an amino acid sequence of at least 90% sequence homology to an amino acid sequence according to SEQ ID NO: 29. In some embodiments, the fusion protein or second fusion protein comprises an amino acid sequence of at least 95% sequence homology to an amino acid sequence according to SEQ ID NO: 29. In some embodiments, the fusion protein or second fusion protein comprises an amino acid sequence of at least 98% sequence homology to an amino acid sequence according to SEQ ID NO: 29. In some embodiments, the fusion protein or second fusion protein comprises an amino acid sequence of at least 99% sequence homology to an amino acid sequence according to SEQ ID NO: 29.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 29.

In some embodiments, the fusion protein or second fusion protein comprises an amino acid sequence of at least 75% sequence identity to an amino acid sequence according to SEQ ID NO: 30. In some embodiments, the fusion protein or second fusion protein comprises an amino acid sequence of at least 80% sequence identity to an amino acid sequence according to SEQ ID NO: 30. In some embodiments, the fusion protein or second fusion protein comprises an amino acid sequence of at least 85% sequence identity to an amino acid sequence according to SEQ ID NO: 30. In some embodiments, the fusion protein or second fusion protein comprises an amino acid sequence of at least 90% sequence identity to an amino acid sequence according to SEQ ID NO: 30. In some embodiments, the fusion protein or second fusion protein comprises an amino acid sequence of at least 95% sequence identity to an amino acid sequence according to SEQ ID NO: 30. In some embodiments, the fusion protein or second fusion protein comprises an amino acid sequence of at least 98% sequence identity to an amino acid sequence according to SEQ ID NO: 30. In some embodiments, the fusion protein or second fusion protein comprises an amino acid sequence of at least 99% sequence identity to an amino acid sequence according to SEQ ID NO: 30.

In some embodiments, the fusion protein or second fusion protein comprises an amino acid sequence of at least 75% sequence homology to an amino acid sequence according to SEQ ID NO: 30. In some embodiments, the fusion protein or second fusion protein comprises an amino acid sequence of at least 80% sequence homology to an amino acid sequence according to SEQ ID NO: 30. In some embodiments, the fusion protein or second fusion protein comprises an amino acid sequence of at least 85% sequence homology to an amino acid sequence according to SEQ ID NO: 30. In some embodiments, the fusion protein or second fusion protein comprises an amino acid sequence of at least 90% sequence homology to an amino acid sequence according to SEQ ID NO: 30. In some embodiments, the fusion protein or second fusion protein comprises an amino acid sequence of at least 95% sequence homology to an amino acid sequence according to SEQ ID NO: 30. In some embodiments, the fusion protein or second fusion protein comprises an amino acid sequence of at least 98% sequence homology to an amino acid sequence according to SEQ ID NO: 30. In some embodiments, the fusion protein or second fusion protein comprises an amino acid sequence of at least 99% sequence homology to an amino acid sequence according to SEQ ID NO: 30.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 30.

In some embodiments, the fusion protein or second fusion protein comprises an amino acid sequence of at least 75% sequence identity to an amino acid sequence according to SEQ ID NO: 31. In some embodiments, the fusion protein or second fusion protein comprises an amino acid sequence of at least 80% sequence identity to an amino acid sequence according to SEQ ID NO: 31. In some embodiments, the fusion protein or second fusion protein comprises an amino acid sequence of at least 85% sequence identity to an amino acid sequence according to SEQ ID NO: 31. In some embodiments, the fusion protein or second fusion protein comprises an amino acid sequence of at least 90% sequence identity to an amino acid sequence according to SEQ ID NO: 31. In some embodiments, the fusion protein or second fusion protein comprises an amino acid sequence of at least 95% sequence identity to an amino acid sequence according to SEQ ID NO: 31. In some embodiments, the fusion protein or second fusion protein comprises an amino acid sequence of at least 98% sequence identity to an amino acid sequence according to SEQ ID NO: 31. In some embodiments, the fusion protein or second fusion protein comprises an amino acid sequence of at least 99% sequence identity to an amino acid sequence according to SEQ ID NO: 31.

In some embodiments, the fusion protein or second fusion protein comprises an amino acid sequence of at least 75% sequence homology to an amino acid sequence according to SEQ ID NO: 31. In some embodiments, the fusion protein or second fusion protein comprises an amino acid sequence of at least 80% sequence homology to an amino acid sequence according to SEQ ID NO: 31. In some embodiments, the fusion protein or second fusion protein comprises an amino acid sequence of at least 85% sequence homology to an amino acid sequence according to SEQ ID NO: 31. In some embodiments, the fusion protein or second fusion protein comprises an amino acid sequence of at least 90% sequence homology to an amino acid sequence according to SEQ ID NO: 31. In some embodiments, the fusion protein or second fusion protein comprises an amino acid sequence of at least 95% sequence homology to an amino acid sequence according to SEQ ID NO: 31. In some embodiments, the fusion protein or second fusion protein comprises an amino acid sequence of at least 98% sequence homology to an amino acid sequence according to SEQ ID NO: 31. In some embodiments, the fusion protein or second fusion protein comprises an amino acid sequence of at least 99% sequence homology to an amino acid sequence according to SEQ ID NO: 31.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 31.

In some embodiments, the fusion protein or second fusion protein comprises an amino acid sequence of at least 75% sequence identity to an amino acid sequence according to SEQ ID NO: 32. In some embodiments, the fusion protein or second fusion protein comprises an amino acid sequence of at least 80% sequence identity to an amino acid sequence according to SEQ ID NO: 32. In some embodiments, the fusion protein or second fusion protein comprises an amino acid sequence of at least 85% sequence identity to an amino acid sequence according to SEQ ID NO: 32. In some embodiments, the fusion protein or second fusion protein comprises an amino acid sequence of at least 90% sequence identity to an amino acid sequence according to SEQ ID NO: 32. In some embodiments, the fusion protein or second fusion protein comprises an amino acid sequence of at least 95% sequence identity to an amino acid sequence according to SEQ ID NO: 32. In some embodiments, the fusion protein or second fusion protein comprises an amino acid sequence of at least 98% sequence identity to an amino acid sequence according to SEQ ID NO: 32. In some embodiments, the fusion protein or second fusion protein comprises an amino acid sequence of at least 99% sequence identity to an amino acid sequence according to SEQ ID NO: 32.

In some embodiments, the fusion protein or second fusion protein comprises an amino acid sequence of at least 75% sequence homology to an amino acid sequence according to SEQ ID NO: 32. In some embodiments, the fusion protein or second fusion protein comprises an amino acid sequence of at least 80% sequence homology to an amino acid sequence according to SEQ ID NO: 32. In some embodiments, the fusion protein or second fusion protein comprises an amino acid sequence of at least 85% sequence homology to an amino acid sequence according to SEQ ID NO: 32. In some embodiments, the fusion protein or second fusion protein comprises an amino acid sequence of at least 90% sequence homology to an amino acid sequence according to SEQ ID NO: 32. In some embodiments, the fusion protein or second fusion protein comprises an amino acid sequence of at least 95% sequence homology to an amino acid sequence according to SEQ ID NO: 32. In some embodiments, the fusion protein or second fusion protein comprises an amino acid sequence of at least 98% sequence homology to an amino acid sequence according to SEQ ID NO: 32. In some embodiments, the fusion protein or second fusion protein comprises an amino acid sequence of at least 99% sequence homology to an amino acid sequence according to SEQ ID NO: 32.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 32.

In some embodiments, the fusion protein or second fusion protein comprises an amino acid sequence of at least 75% sequence identity to an amino acid sequence according to SEQ ID NO: 33. In some embodiments, the fusion protein or second fusion protein comprises an amino acid sequence of at least 80% sequence identity to an amino acid sequence according to SEQ ID NO: 33. In some embodiments, the fusion protein or second fusion protein comprises an amino acid sequence of at least 85% sequence identity to an amino acid sequence according to SEQ ID NO: 33. In some embodiments, the fusion protein or second fusion protein comprises an amino acid sequence of at least 90% sequence identity to an amino acid sequence according to SEQ ID NO: 33. In some embodiments, the fusion protein or second fusion protein comprises an amino acid sequence of at least 95% sequence identity to an amino acid sequence according to SEQ ID NO: 33. In some embodiments, the fusion protein or second fusion protein comprises an amino acid sequence of at least 98% sequence identity to an amino acid sequence according to SEQ ID NO: 33. In some embodiments, the fusion protein or second fusion protein comprises an amino acid sequence of at least 99% sequence identity to an amino acid sequence according to SEQ ID NO: 33.

In some embodiments, the fusion protein or second fusion protein comprises an amino acid sequence of at least 75% sequence homology to an amino acid sequence according to SEQ ID NO: 33. In some embodiments, the fusion protein or second fusion protein comprises an amino acid sequence of at least 80% sequence homology to an amino acid sequence according to SEQ ID NO: 33. In some embodiments, the fusion protein or second fusion protein comprises an amino acid sequence of at least 85% sequence homology to an amino acid sequence according to SEQ ID NO: 33. In some embodiments, the fusion protein or second fusion protein comprises an amino acid sequence of at least 90% sequence homology to an amino acid sequence according to SEQ ID NO: 33. In some embodiments, the fusion protein or second fusion protein comprises an amino acid sequence of at least 95% sequence homology to an amino acid sequence according to SEQ ID NO: 33. In some embodiments, the fusion protein or second fusion protein comprises an amino acid sequence of at least 98% sequence homology to an amino acid sequence according to SEQ ID NO: 33. In some embodiments, the fusion protein or second fusion protein comprises an amino acid sequence of at least 99% sequence homology to an amino acid sequence according to SEQ ID NO: 33.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 33.

In some embodiments, the fusion protein or second fusion protein comprises an amino acid sequence of at least 75% sequence identity to an amino acid sequence according to SEQ ID NO: 34. In some embodiments, the fusion protein or second fusion protein comprises an amino acid sequence of at least 80% sequence identity to an amino acid sequence according to SEQ ID NO: 34. In some embodiments, the fusion protein or second fusion protein comprises an amino acid sequence of at least 85% sequence identity to an amino acid sequence according to SEQ ID NO: 34. In some embodiments, the fusion protein or second fusion protein comprises an amino acid sequence of at least 90% sequence identity to an amino acid sequence according to SEQ ID NO: 34. In some embodiments, the fusion protein or second fusion protein comprises an amino acid sequence of at least 95% sequence identity to an amino acid sequence according to SEQ ID NO: 34. In some embodiments, the fusion protein or second fusion protein comprises an amino acid sequence of at least 98% sequence identity to an amino acid sequence according to SEQ ID NO: 34. In some embodiments, the fusion protein or second fusion protein comprises an amino acid sequence of at least 99% sequence identity to an amino acid sequence according to SEQ ID NO: 34.

In some embodiments, the fusion protein or second fusion protein comprises an amino acid sequence of at least 75% sequence homology to an amino acid sequence according to SEQ ID NO: 34. In some embodiments, the fusion protein or second fusion protein comprises an amino acid sequence of at least 80% sequence homology to an amino acid sequence according to SEQ ID NO: 34. In some embodiments, the fusion protein or second fusion protein comprises an amino acid sequence of at least 85% sequence homology to an amino acid sequence according to SEQ ID NO: 34. In some embodiments, the fusion protein or second fusion protein comprises an amino acid sequence of at least 90% sequence homology to an amino acid sequence according to SEQ ID NO: 34. In some embodiments, the fusion protein or second fusion protein comprises an amino acid sequence of at least 95% sequence homology to an amino acid sequence according to SEQ ID NO: 34. In some embodiments, the fusion protein or second fusion protein comprises an amino acid sequence of at least 98% sequence homology to an amino acid sequence according to SEQ ID NO: 34. In some embodiments, the fusion protein or second fusion protein comprises an amino acid sequence of at least 99% sequence homology to an amino acid sequence according to SEQ ID NO: 34.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 34.

In some embodiments, the fusion protein or second fusion protein comprises an amino acid sequence of at least 75% sequence identity to an amino acid sequence according to SEQ ID NO: 35. In some embodiments, the fusion protein or second fusion protein comprises an amino acid sequence of at least 80% sequence identity to an amino acid sequence according to SEQ ID NO: 35. In some embodiments, the fusion protein or second fusion protein comprises an amino acid sequence of at least 85% sequence identity to an amino acid sequence according to SEQ ID NO: 35. In some embodiments, the fusion protein or second fusion protein comprises an amino acid sequence of at least 90% sequence identity to an amino acid sequence according to SEQ ID NO: 35. In some embodiments, the fusion protein or second fusion protein comprises an amino acid sequence of at least 95% sequence identity to an amino acid sequence according to SEQ ID NO: 35. In some embodiments, the fusion protein or second fusion protein comprises an amino acid sequence of at least 98% sequence identity to an amino acid sequence according to SEQ ID NO: 35. In some embodiments, the fusion protein or second fusion protein comprises an amino acid sequence of at least 99% sequence identity to an amino acid sequence according to SEQ ID NO: 35.

In some embodiments, the fusion protein or second fusion protein comprises an amino acid sequence of at least 75% sequence homology to an amino acid sequence according to SEQ ID NO: 35. In some embodiments, the fusion protein or second fusion protein comprises an amino acid sequence of at least 80% sequence homology to an amino acid sequence according to SEQ ID NO: 35. In some embodiments, the fusion protein or second fusion protein comprises an amino acid sequence of at least 85% sequence homology to an amino acid sequence according to SEQ ID NO: 35. In some embodiments, the fusion protein or second fusion protein comprises an amino acid sequence of at least 90% sequence homology to an amino acid sequence according to SEQ ID NO: 35. In some embodiments, the fusion protein or second fusion protein comprises an amino acid sequence of at least 95% sequence homology to an amino acid sequence according to SEQ ID NO: 35. In some embodiments, the fusion protein or second fusion protein comprises an amino acid sequence of at least 98% sequence homology to an amino acid sequence according to SEQ ID NO: 35. In some embodiments, the fusion protein or second fusion protein comprises an amino acid sequence of at least 99% sequence homology to an amino acid sequence according to SEQ ID NO: 35.

In some instances, the fusion protein or second fusion protein comprises an amino acid sequence comprising at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, or more than 720 consecutive amino acids of SEQ ID NO: 35.

Compositions for Generation of Multivalent Particles

Described herein, in some embodiments, are compositions comprising a multivalent particle comprising a fusion protein that comprises a mammalian polypeptide that binds to a viral protein and a transmembrane polypeptide. In some embodiments, the compositions comprise a first nucleic acid sequence encoding the multivalent particle described herein.

Compositions for generating multivalent particles, in some embodiments, further comprise a second nucleic acid sequence that encodes one or more packaging viral proteins. In some embodiments, the one or more packaging viral proteins is a lentiviral protein, a retroviral protein, an adenoviral protein, or combinations thereof. In some embodiments, the one or more packaging viral proteins comprises gag, pol, pre, tat, rev, or combinations thereof.

Compositions for generating multivalent particles, in some embodiments, further comprise a second nucleic acid sequence that encodes an expression construct for specifically targeting the mammalian polypeptide to the surface of an extracellular vesicle. In some embodiments, the second nucleic acid sequence encodes an expression construct for specifically targeting the mammalian polypeptide to the surface of an exosome. In some embodiments, the second nucleic acid sequence encodes an expression construct for specifically targeting the mammalian polypeptide to the surface of an ectosome.

Compositions for generating multivalent particles, in some embodiments, further comprise a third nucleic acid sequence that encodes a replication incompetent viral genome, a reporter, a therapeutic molecule, or combinations thereof. In some embodiments, compositions can further comprise a third nucleic acid sequence that encodes a replication competent viral genome, a reporter, a therapeutic molecule, or combinations thereof. In some embodiments, the viral genome is derived from vesicular stomatitis virus, measles virus, Hepatitis virus, influenza virus, or combinations thereof.

In some embodiments, the reporter protein is a fluorescent protein or an enzyme. Exemplary reporter genes include, but are not limited to, acetohydroxyacid synthase (AHAS), alkaline phosphatase (AP), beta galactosidase (LacZ), beta glucuronidase (GUS), chloramphenicol acetyltransferase (CAT), green fluorescent protein (GFP), red fluorescent protein (RFP), yellow fluorescent protein (YFP), cyan fluorescent protein (CFP), cerulean fluorescent protein, citrine fluorescent protein, orange fluorescent protein, cherry fluorescent protein, turquoise fluorescent protein, blue fluorescent protein, horseradish peroxidase (HRP), luciferase (Luc), nopaline synthase (NOS), octopine synthase (OCS), luciferase, and derivatives thereof. Methods to determine modulation of a reporter gene are well known in the art, and include, but are not limited to, fluorometric methods (e.g. fluorescence spectroscopy, Fluorescence Activated Cell Sorting (FACS), fluorescence microscopy), and antibiotic resistance determination. In some embodiments, the reporter is a fluorescent protein. In some embodiments, the fluorescent protein is green fluorescent protein. In some embodiments, the reporter protein emits green fluorescence, yellow fluorescence, or red fluorescence. In some embodiments, the reporter is an enzyme. In some embodiments, the enzyme is β-galactosidase, alkaline phosphatase, β-lactamase, or luciferase.

In some embodiments, the therapeutic molecule is an immune modulating protein, a cellular signal modulating molecule, a proliferation modulating molecule, a cell death modulating molecule, or combinations thereof. In some embodiments, the therapeutic molecule is an immune checkpoint molecule. Exemplary immune checkpoint molecules include, but are not limited to, CTLA4, PD1, OX40, and CD28. In some embodiments, the therapeutic molecule is an inflammatory cytokine. In some embodiments, the inflammatory cytokine comprises IL-1, IL-12, or IL-18. In some embodiments, the therapeutic molecule is a proliferation cytokine. In some embodiments, the proliferation cytokine comprises IL-4, IL-7, or IL-15. In some embodiments, the cell death molecule comprises Fas or a death receptor.

Compositions for generating multivalent particles, in some embodiments, further comprise a fourth nucleic acid sequence encoding a second fusion protein that comprises a second mammalian polypeptide and a second transmembrane polypeptide that binds to the viral protein as described herein.

In some embodiments, the first nucleic acid sequence, the second nucleic acid sequence, and the third nucleic acid sequence are within a same vector. In some embodiments, the first nucleic acid sequence, the second nucleic acid sequence, and the third nucleic acid sequence are within different vectors. In some embodiments, the first nucleic acid sequence, the second nucleic acid sequence, the third nucleic acid sequence, and the fourth nucleic acid sequence are within a same vector. In some embodiments, the first nucleic acid sequence, the second nucleic acid sequence, third nucleic acid sequence, and the fourth nucleic acid sequence are within different vectors.

Various vectors, in some embodiments, are used herein. In some embodiments, the vector is a eukaryotic or prokaryotic vector. In some embodiments, the vector is a viral vector. In some embodiments, the vector is a lentivirus vector, an adenovirus vector, or an adeno-associated virus vector. Exemplary vectors include, without limitation, mammalian expression vectors: pSF-CMV-NEO-NH2-PPT-3XFLAG, pSF-CMV-NEO-COOH-3XFLAG, pSF-CMV-PURO-NH2-GST-TEV, pSF-OXB20-COOH-TEV-FLAG(R)-6His, pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV-PUBO-NH2-CMYC; bacterial expression vectors: pSF-OXB20-BetaGal, pSF-OXB20-Fluc, pSF-OXB20, and pSF-Tac; plant expression vectors: pRI 101-AN DNA and pCambia2301; and yeast expression vectors: pTYB21 and pKLAC2, and insect vectors: pAc5.1/V5-His A and pDEST8.

Compositions and Pharmaceutical Compositions

Described herein, in some embodiments, are compositions comprising a multivalent particle comprising a fusion protein that comprises a mammalian polypeptide that binds to a viral protein and a transmembrane polypeptide. Described herein, in some embodiments, are pharmaceutical compositions comprising a multivalent particle comprising a fusion protein that comprises a mammalian polypeptide that binds to a viral protein and a transmembrane polypeptide.

For administration to a subject, the multivalent particles as disclosed herein, may be provided in a pharmaceutical composition together with one or more pharmaceutically acceptable carriers or excipients. In some embodiments, the multivalent particles as disclosed herein, may be provided in a composition together with one or more carriers or excipients. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, intravenous, or inhalation) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Methods of Use

Multivalent particles described herein, in some embodiments, are used to treat a viral infection. In some instances, the viral infection is caused by SARS-CoV-1. In some instances, the viral infection is caused by SARS-CoV-2. In some instances, the viral infection is caused by MERS-CoV. In some instances, the viral infection is caused by respiratory syncytial virus. In some instances, the viral infection is caused by HIV.

In some instances, the subject is a mammal. In some instances, the subject is a mouse, rabbit, dog, pig, cattle, or human. Subjects treated by methods described herein may be infants, adults, or children. Pharmaceutical compositions or compositions comprising multivalent particles as described herein may be administered intravenously, subcutaneously, or inhalation. In some embodiments, the multivalent particle is administered intravenously. In some embodiments, the multivalent particle is administered through inhalation. In some embodiments, the multivalent particle is administered by an intraperitoneal injection. In some embodiments, the multivalent particle is administered by a subcutaneous injection.

Described herein, in some embodiments, are methods of treating an infection in a subject in need thereof comprising administering to the subject a multivalent particle described herein. In some embodiments, the infection comprises infection by SARS-CoV-1, SARS-CoV-2, MERS-CoV, Respiratory syncytial virus, HIV, or combinations thereof. In some embodiments, the infection comprises infection by SARS-CoV-1. In some embodiments, the infection comprises infection by SARS-CoV-2. In some embodiments, the infection comprises infection by MERS-CoV.

In some embodiments, the multivalent particle is administered to the subject through inhalation. In some embodiments, the multivalent particle is administered to the subject through intranasal delivery. In some embodiments, the multivalent particle is administered to the subject through intratracheal delivery. In some embodiments, the multivalent particle is administered to the subject by an intraperitoneal injection. In some embodiments, the multivalent particle is administered to the subject by a subcutaneous injection. In some embodiments, the administering to the subject of the multivalent particle is sufficient to reduce or eliminate the infection as compared to a baseline measurement of the infection taken from the subject prior to the administering of the multivalent particle. In some embodiments, the reduction is at least about 1-fold, 5-fold, 10-fold, 20-fold, 40-fold, 60-fold, 80-fold, or up to about 100-fold.

Described herein, in some embodiments, are methods of treating an infection in a subject in need thereof comprising administering to the subject a composition, wherein the composition comprises a nucleic acid sequence that encodes a first fusion protein disclosed herein. Described herein, in some embodiments, are methods of treating an infection in a subject in need thereof comprising administering to the subject a composition, wherein the composition comprises a nucleic acid sequence that encodes a first fusion protein disclosed herein and a second fusion protein disclosed herein. In some embodiments, the infection comprises infection by SARS-CoV-1, SARS-CoV-2, MERS-CoV, Respiratory syncytial virus, HIV, or combinations thereof. In some embodiments, the nucleic acid sequence comprises mRNA. In some embodiments, the nucleic acid sequence comprises DNA.

In some embodiments, the composition is administered to the subject through inhalation. In some embodiments, the composition is administered to the subject through intranasal delivery. In some embodiments, the composition is administered to the subject through intratracheal delivery. In some embodiments, the composition is administered to the subject by an intraperitoneal injection. In some embodiments, the composition is administered to the subject by a subcutaneous injection. In some embodiments, the administering to the subject of the composition is sufficient to reduce or eliminate the infection as compared to a baseline measurement of the infection taken from the subject prior to the administering of the composition. In some embodiments, the reduction is at least about 1-fold, 5-fold, 10-fold, 20-fold, 40-fold, 60-fold, 80-fold, or up to about 100-fold.

In some embodiments, the mRNAs that encode the first fusion protein and the second fusion protein and the second nucleic acid sequence and the third nucleic acid sequence are administered inhalation. In some embodiments, the mRNAs that encode the first fusion protein and the second fusion protein and the second nucleic acid sequence and the third nucleic acid sequence are administered through intranasal delivery. In some embodiments, the mRNAs that encode the first fusion protein and the second fusion protein and the second nucleic acid sequence and the third nucleic acid sequence are administered intratracheal delivery. In some embodiments, the mRNAs that encode the first fusion protein and the second fusion protein and the second nucleic acid sequence and the third nucleic acid sequence are administered by an intraperitoneal injection. In some embodiments, the mRNAs that encode the first fusion protein and the second fusion protein and the second nucleic acid sequence and the third nucleic acid sequence are administered by a subcutaneous injection. In some embodiments, the administering to the subject of the composition is sufficient to reduce or eliminate the infection as compared to a baseline measurement of the infection taken from the subject prior to the administering of the composition. In some embodiments, the reduction is at least about 1-fold, 5-fold, 10-fold, 20-fold, 40-fold, 60-fold, 80-fold, or up to about 100-fold.

In some embodiments, the DNAs that encode the first fusion protein and the second fusion protein and the second nucleic acid sequence and the third nucleic acid sequence are administered inhalation. In some embodiments, the DNAs that encode the first fusion protein and the second fusion protein and the second nucleic acid sequence and the third nucleic acid sequence are administered through intranasal delivery. In some embodiments, the DNAs that encode the first fusion protein and the second fusion protein and the second nucleic acid sequence and the third nucleic acid sequence are administered intratracheal delivery. In some embodiments, the DNAs that encode the first fusion protein and the second fusion protein and the second nucleic acid sequence and the third nucleic acid sequence are administered by an intraperitoneal injection. In some embodiments, the DNAs that encode the first fusion protein and the second fusion protein and the second nucleic acid sequence and the third nucleic acid sequence are administered by a subcutaneous injection. In some embodiments, the administering to the subject of the composition is sufficient to reduce or eliminate the infection as compared to a baseline measurement of the infection taken from the subject prior to the administering of the composition. In some embodiments, the reduction is at least about 1-fold, 5-fold, 10-fold, 20-fold, 40-fold, 60-fold, 80-fold, or up to about 100-fold.

In some embodiments, the composition comprises a liposome. In some embodiments, the liposome comprises a protamine liposome. In some embodiments, the liposome comprises a cationic polymer liposome. In some embodiments, the composition comprises a lipid nanoparticle. In some embodiments, the composition comprises a cationic lipid nanoparticle. In some embodiments, the composition comprises a cationic lipid, cholesterol nanoparticle. In some embodiments, the composition comprises a cationic lipid, cholesterol, PEG nanoparticle. In some embodiments, the composition comprises with a dendrimer nanoparticle.

In some embodiments, the composition comprises an adeno-associated virus (AAV). In some embodiments, the composition comprises a polymer. In some embodiments, the composition comprises protamine. In some embodiments, the composition comprises polysaccharide particle. In some embodiments, the composition comprises a cationic polymer. In some embodiments, the composition comprises a cationic nano-emulsion. In some embodiments, the composition comprises a transfection reagent. In some embodiments, the composition comprises a dendritic cell.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Design and Production of Decoy Multivalent Particles Displaying ACE2 Receptors (ACE2-MVPs)

ACE2-MVPs were generated by pseudotyping lentiviral particles with a fusion protein consisting of the ACE2 extracellular domain and the membrane anchoring segment of a viral envelop protein (FIG. 1A). Briefly, ACE2-MVPs were generated by co-transfecting the ACE2 fusion construct with a lentiviral packaging construct expressing essential packaging components, such as Gag-Pol and Rev proteins, and a viral genome transfer vector encoding a GFP/luciferase reporter (Example 20). ACE2-MVPs without viral genomes were also packaged with no transfer vector. Several viral envelope proteins were tested for anchoring ACE2 protein to the membrane of the pseudo-lentiviral particles, including VSV-G (glycoprotein of Vesicular Stomatitis virus), HCΔ18 (a mutant version of the hemagglutinin envelope protein from measles virus), and S2 (the fusion domain of the SARS CoV-2 spike protein). Also tested were the fusion of ACE2 to full-length VSVG or truncated VSV-G with only a transmembrane region and cytosolic tail.

Figure 1B:
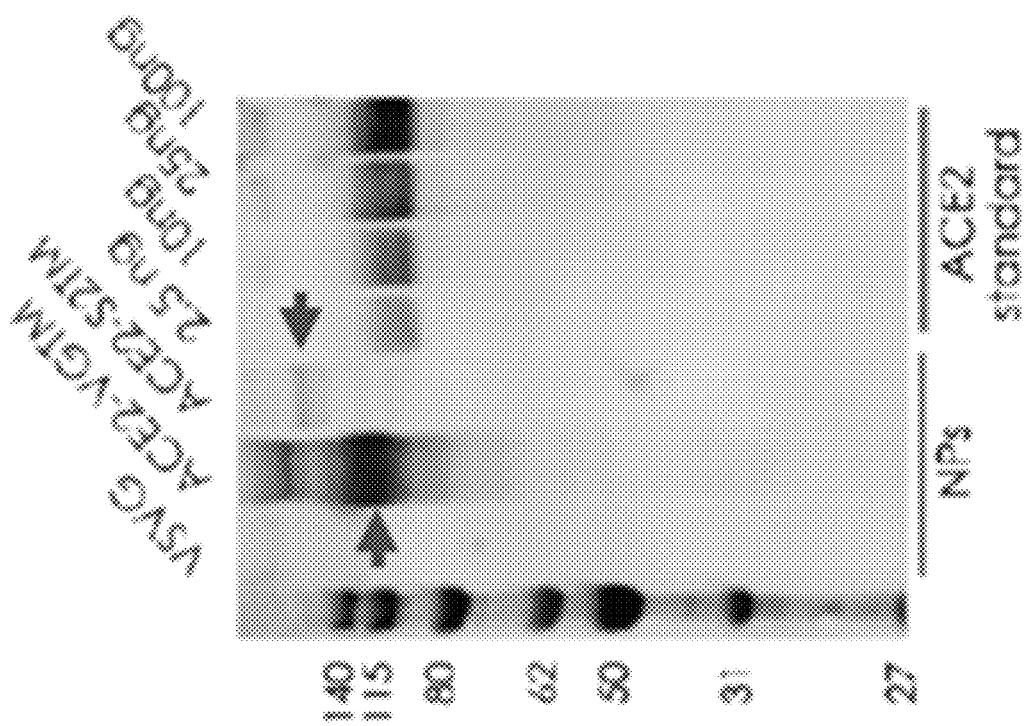
FIG. 1B depicts quantitative Western blot analysis of ACE2 valency of different multivalent particles.
Figures 1C, 1D:
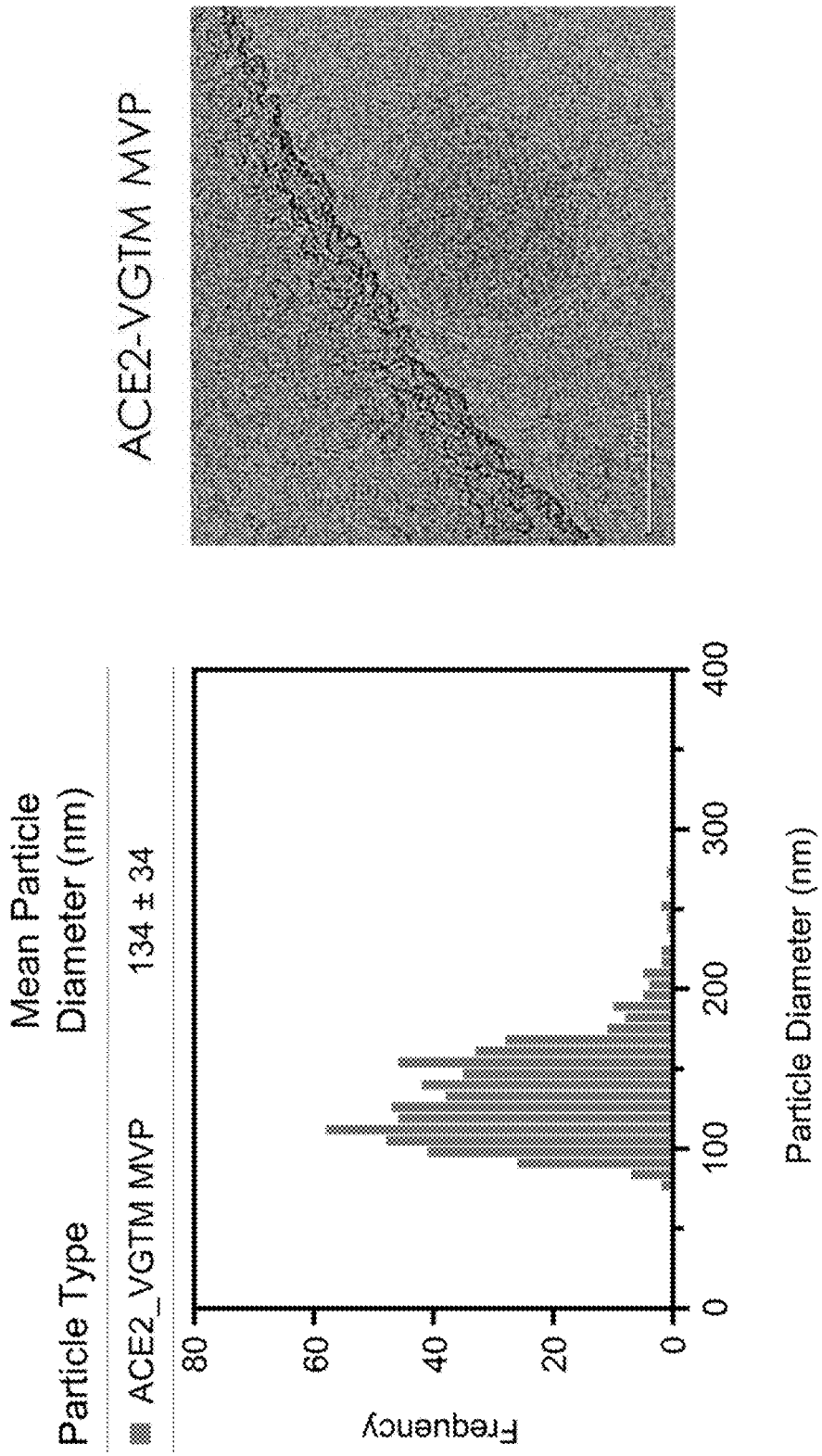
FIG. 1C shows the particle size distribution of ACE2-VGTM MVPs as determined by Tunable Resistive Pulse Sensing Analysis using a qNano instrument.
FIG. 1D shows representative Electron Microscopy images of ACE2-VGTM MVPs at nominal magnification of 150,000×.

Among the variations of ACE2 fusion proteins, ACE2 fused with VSVG transmembrane domain (VGTM), and S2 transmembrane domain (S2TM) produced ACE2-MVPs with high copies of the ACE2 fusion protein on the viral-like particle surface as determined by quantitative Western blot analyses (FIG. 1B). These pseudotyped MVPs displayed about eight copies of ACE2-S2TM or 236 copies of ACE2-VGTM on the particles, respectively, providing a basis to test the effects of valency on the neutralizing function of ACE2-MVPs. The average particle diameter of ACE2-VGTM MVPs was 134±34 nm, as determined by tunable resistive pulse sensing analyses (TRPS) using qNano (FIG. 1C). The morphology of ACE2-VGTM MVPs were characterized by cryoEM analyses at nominal magnification of 150,000× (FIG. 1D).

Example 2: Efficient Inhibition of SARS CoV-2 Virus Infection by ACE2-MVPs

Figure 2A:
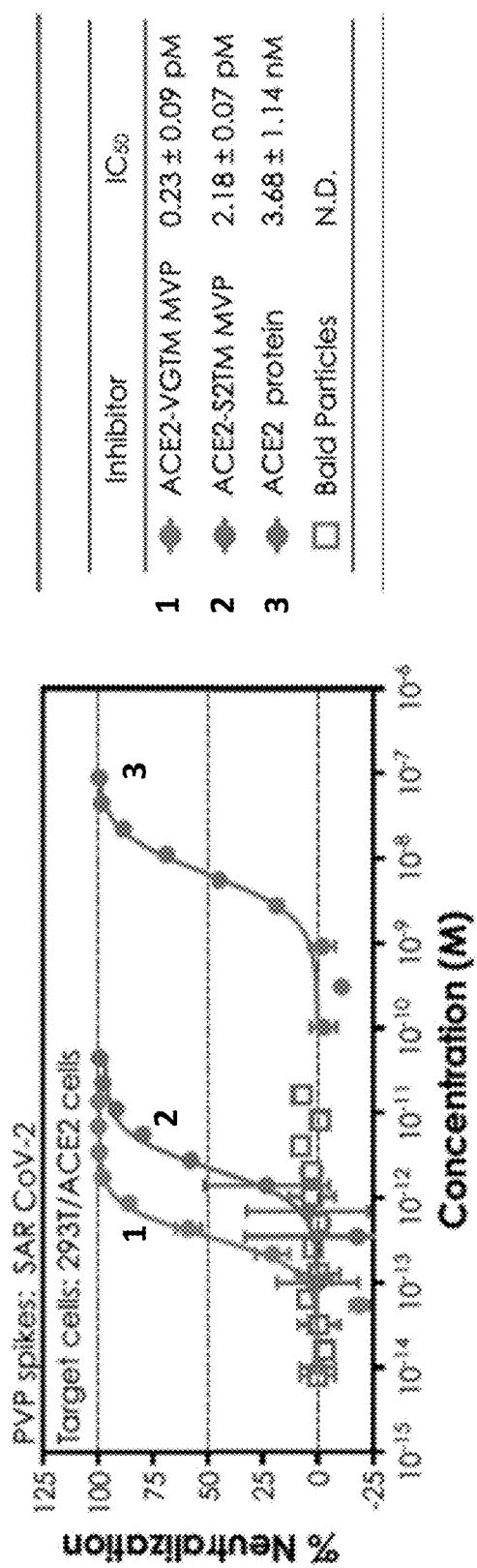
FIG. 2A depicts results of a microneutralization assay using 293T/ACE2 cells as target cells.
Figure 2C:
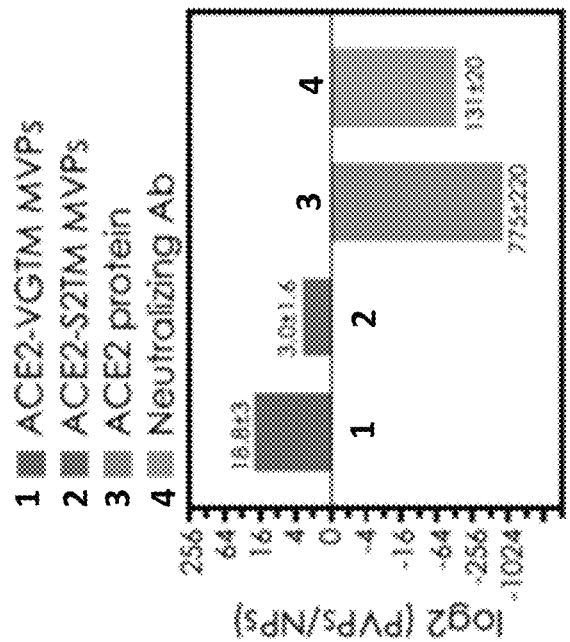
FIG. 2C depicts stoichiometric ratios between the neutralizing decoy ACE2-MVPs and the pseudovirus particles as determined by P24 ELISA assays.
Figure 2B:
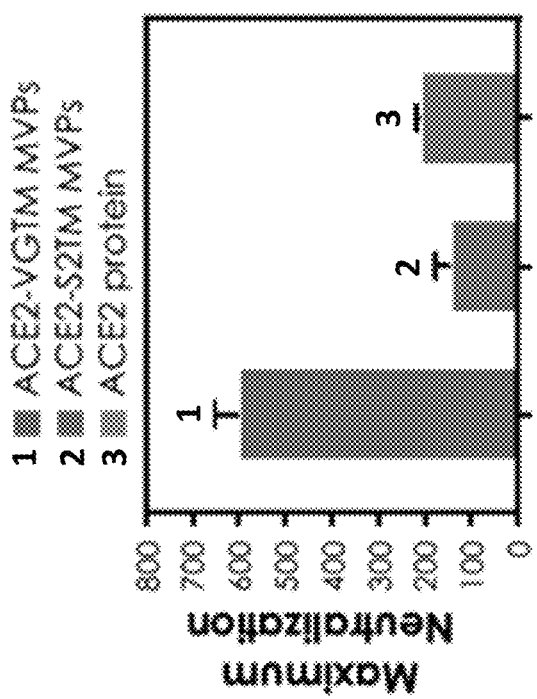
FIG. 2B depicts the maximum inhibition of pseudovirus infection by different multivalent particles.

The neutralizing activity of ACE2-MVPs were determined in a microneutralization assay against lentiviruses pseudotyped with SARS CoV-2 spike protein (CoV-2 PVP) using 293T/ACE2 cells as target cells (Example 20). Recombinant ACE2 had an $IC_{50}$ of 3.68±1.14 nM in the pseudovirus neutralization assay, as shown in FIG. 2A. In contrast, the decoy-MVPs displaying ACE2-VGTM or ACE2-S2TM had $IC_{50}$ values of 0.23±0.09 pM or 2.18±0.07 pM, respectively, which were at least 1000-fold or 10,000-fold more potent than the monovalent ACE2 recombinant protein (FIG. 2A). The results demonstrated that the neutralizing function of the ACE2 decoy receptor were drastically enhanced by increasing valencies. Notably, the ACE2-VGTM MVPs displaying ~236 copies of ACE2 were about 10-fold more potent than the ACE2-S2TM MVPs displaying ~8 copies of ACE2. Furthermore, the maximum inhibition of pseudovirus infection was about 600-fold by the ACE2-VGTM MVPs, and about ~100 to 200-fold by the ACE2-S2TM MVPs and the ACE2 recombinant proteins (FIG. 2B). Finally, since both ACE2 MVPs and CoV-2 PVPs were pseudotyped lentiviral particles, the stoichiometric ratios between the neutralizing MVPs and the pseudovirus particles were determined by P24 ELISA assays. As shown in FIG. 2C, one particle of ACE2-VGTM MVP or ACE2-S2TM MVP neutralized about 18 or 3 the pseudovirus particles, respectively. About 131 copies of recombinant ACE2 proteins were required to neutralize one pseudovirus particle. Notably, the ACE2-VGTM MVPs were nearly 100-fold more potent than two of the antibodies used in the Regeneron antibody cocktails for clinical studies (FIG. 2D).

FIG. 2A-2D show that higher ACE2 valency on the ACE2-MVPs correlated with enhanced neutralization activity. FIG. 2A-2C show the neutralizing activities of various anti-CoV-2 compounds, including ACE2 recombinant protein, and MVPs displaying ACE2-VGTM or ACE2-S2TM were determined in a SARS CoV-2 pseudovirus infection assay using 293T/ACE2 cells as target cells. FIG. 2A shows $IC_{50}$ values of ACE2-VGTM MVP; ACE2-S2TM MVP; ACE2 protein; and bald particles. FIG. 2B shows maximum neutralization and total fold repression of ACE2-VGTM MVP; ACE2-S2TM MVP; and ACE2 protein. FIG. 2C shows the molecular ratio of viral particle to antiviral compounds of ACE2-VGTM MVP; ACE2-S2TM MVP; and ACE2 protein. FIG. 2D shows the neutralizing activities of the decoy-MVPs displaying ACE2-VGTM and clinical stage neutralizing antibodies, which were determined using a SARS CoV-2 pseudovirus infection assay with 293T/ACE2 cells as target cells.

Figure 3A:
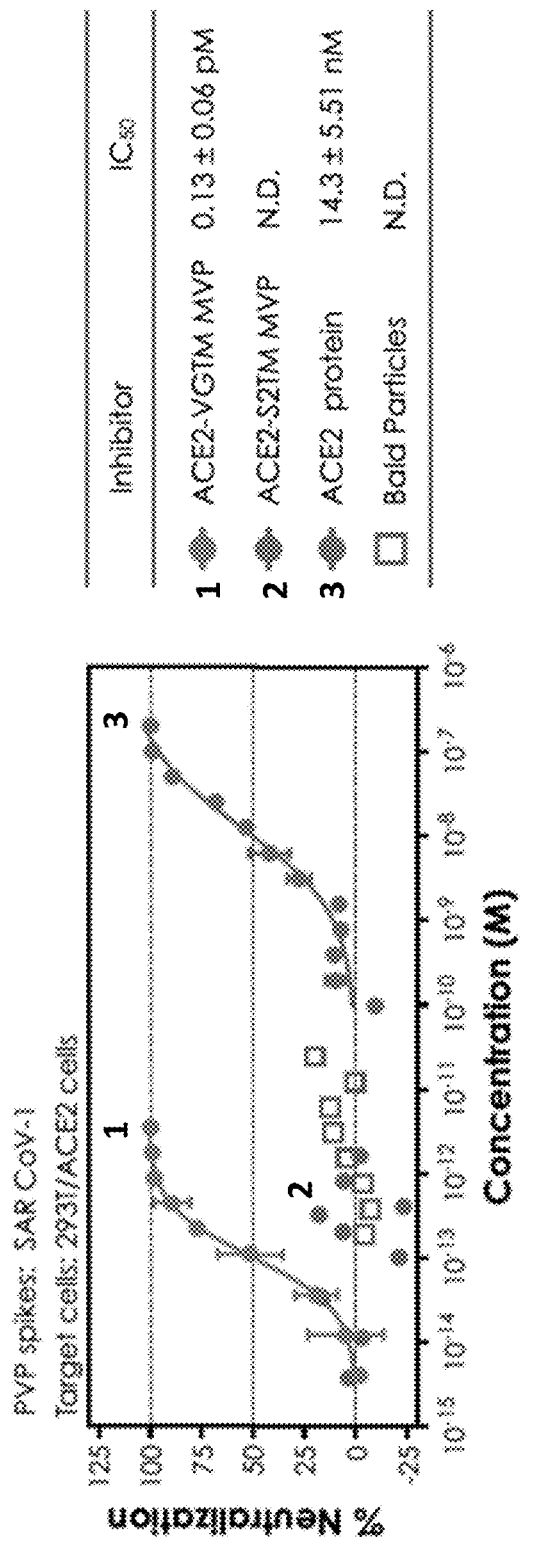
FIG. 3A depicts neutralization of lentiviruses pseudotyped with SARS CoV-1 spike (CoV-1 PVPs).
Figure 3B:
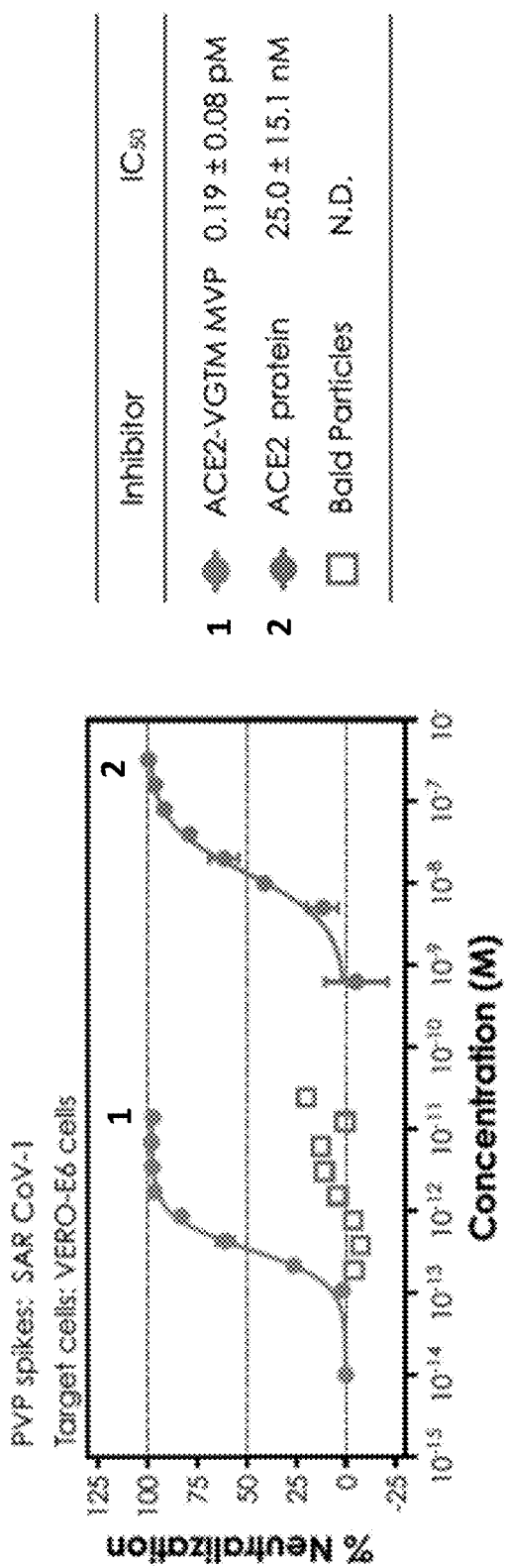
FIG. 3B depicts neutralizing activities of ACE2-MVPs in a CoV-1 PVP neutralization using VERO-E6 cells as target cells.

Example 3: ACE2-MVPs are Broadly Neutralizing Against ACE2-Targeting Coronaviruses ACE2 is used as an entry receptor by SARS CoV-1 and evolving SARS CoV-2, and thus the ACE2-VGTM MVPs may have broad neutralizing activity against these viruses. The neutralizing activities of ACE2-MVPs were tested against lentiviruses pseudotyped with SARS CoV-1 spike (CoV-1 PVPs) in a microneutralization assay using 293T/ACE2 cells as target cells. Recombinant ACE2 had an $IC_{50}$ of 14.3±5.51 nM (FIG. 3A) in a pseudovirus neutralization assay, about 4-5 folds less potent than its activity against CoV-2 PVPs (FIG. 2A), In contrast, the ACE2-VGTM MVP had an $IC_{50}$ of 0.13±0.06 pM, which was comparable to its neutralizing activity against CoV-2 PVPs (FIG. 2A). These results demonstrated that the ACE2-VGTM MVP was a highly potent neutralizing compound against both CoV-1 and CoV-2 viruses, whereas ACE2 recombinant protein showed much less potent neutralizing compound against CoV-1. Furthermore, the ACE2-S2TM MVP, which had ~8 copies of ACE2 per particle, had no detectable neutralizing activity when comparable concentrations to the ACE2-VGTM MVP was used in the neutralization assay (FIG. 3A). The neutralizing activities of ACE-MVPs were also tested in a CoV-1 PVP neutralization using VERO-E6 cells as target cells and observed similar $IC_{50}$ values for the ACE2 recombinant protein and the ACE2-VGTM MVPs (FIG. 3B). In summary, the high-valent ACE2-VGTM MVPs were equally potent in neutralizing both CoV-1 and CoV-2 pseudoviruses, and moreover, higher ACE2 valency on the MVPs appears to overcome the lower affinity between the spike and entry receptor.

SARS CoV-2 is also rapidly mutating, and some of the mutations are more transmissible and more pathogenic. Interestingly, the ACE2-S2TM MVP had an $IC_{50}$ of 41.8±16 fM in neutralizing D614G spike pseudotyped viruses (D614G-PVP) in a microneutralization assay using 293T/ACE2 cells as target cells, which was at least 3-5 folds more potent against CoV-1 PVP and CoV-2 PVP (FIG. 3C), The ACE2-S2TM MVP had comparable neutralizing activities against CoV-1, CoV-2, and D614G-PVPs in a microneutralization assay using H1573/ACE2 cells as target cells (FIG. 3D). Finally, the ACE2-VGTM MVP was equally potent against CoV-2 variants with N439K, N501Y, E484K, and E484Q+L452R mutations (FIG. 3E). These results support that high-valency ACE2-VGTM MVPs are equally potent in neutralizing both SARS CoV-1, SARS CoV-2, and a variety of CoV-2 variant pseudoviruses, and moreover, that higher ACE2 valency on MVPs is critical to overcoming lower binding affinities between viral spike and host cell entry receptor, demonstrating that ACE2-MVPs are potent neutralizing compounds against all emerging coronaviruses utilizing ACE2 as an entry receptor.

Figure 3C:
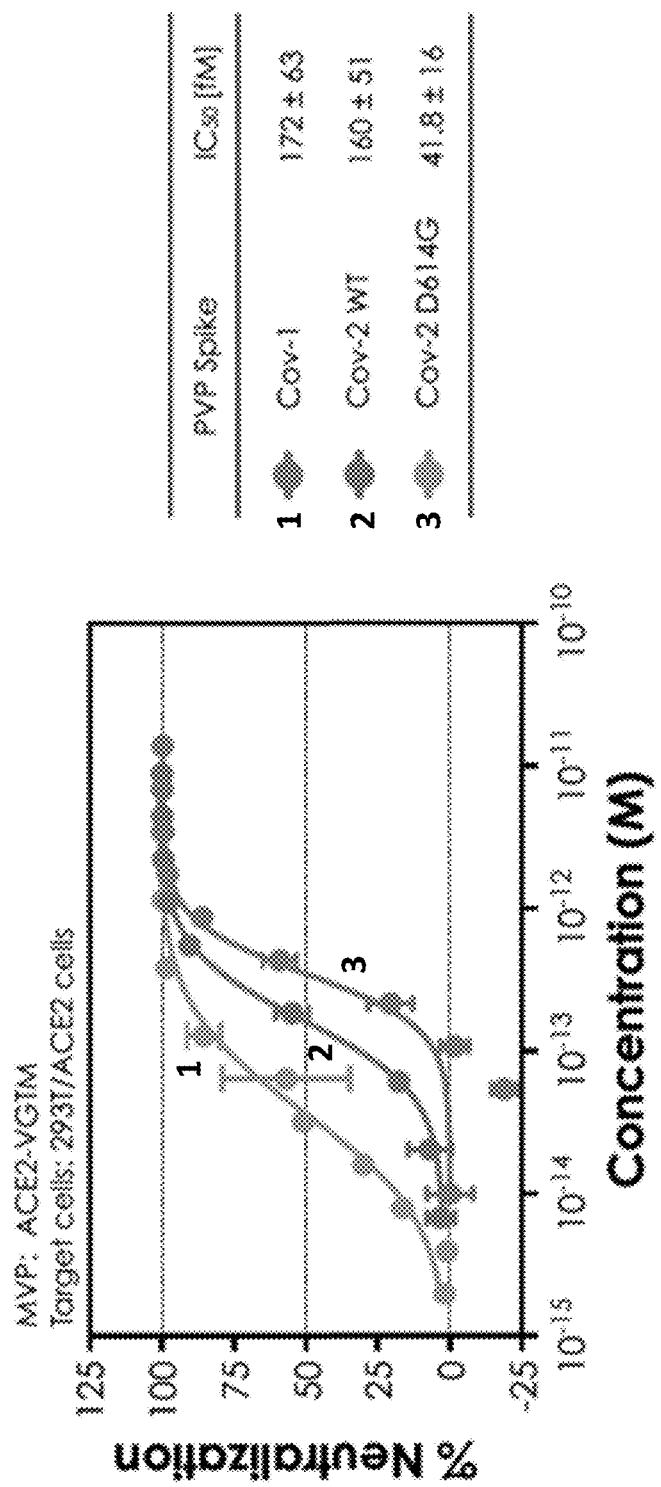
FIG. 3C depicts results of a microneutralization assay against Cov-1, Cov-2 WT and Cov-2 D614G pseudotyped viruses using 293T/ACE2 cells as target cells.
Figure 3D:
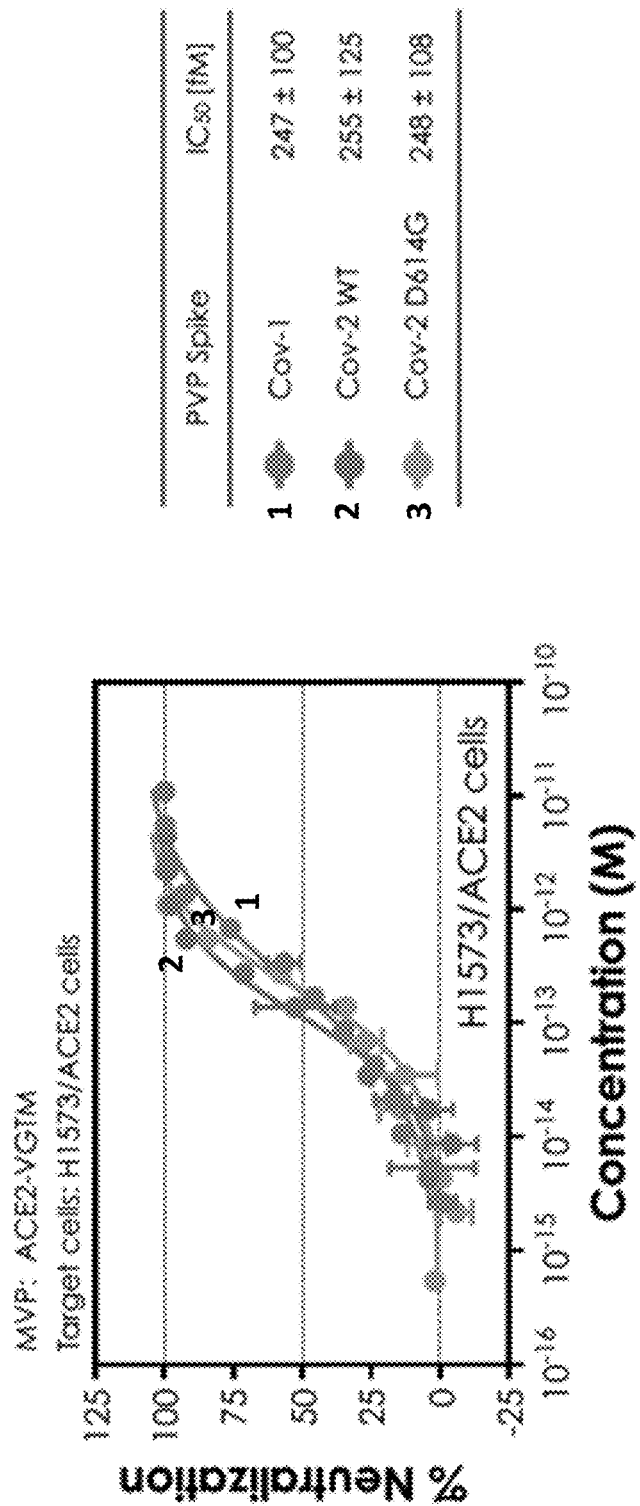
FIG. 3D depicts results of a microneutralization assay against Cov-1, Cov-2 WT and Cov-2 D614G pseudotyped viruses using H1573/ACE2 cells as target cells.

FIG. 3A-3E show the efficient neutralization of SARS-CoV-1 viruses by the ACE2-MVPs, and that neutralization depends on the copies of ACE2 molecules displayed on the particle surfaces. FIG. 3A shows the neutralization activities of the decoy-MVPs displaying ACE2-VGTM or ACE2-S2TM in a SARS CoV-1 pseudovirus infection assay using 293T/ACE2 cells. FIG. 3B shows the neutralization activities of the ACE2-MVPs displaying ACE2-VGTM or ACE2-S2TM in a SARS CoV-1 pseudovirus infection assay using VERO-E6 cells. FIG. 3C shows the neutralization activities of ACE2-VGTM MVPs against CoV-1, CoV-2, and D614G CoV-2 in pseudovirus infection assay using 293T/ACE2 cells. FIG. 3D shows the neutralization activities of ACE2-VGTM MVPs against CoV-1, CoV-2, and D614G CoV-2 in pseudovirus infection assay using H1573/ACE2 cells. FIG. 3E shows a comparison of the neutralizing activities of the ACE2-VGTM MVPs against a variety of SARS CoV-2 variants in pseudovirus infection assay using 293T/ACE2 cells as target cells.

Example 4: Efficient Inhibition of MERS Coronavirus Infection by DPP4-MVPs

Figure 4A:
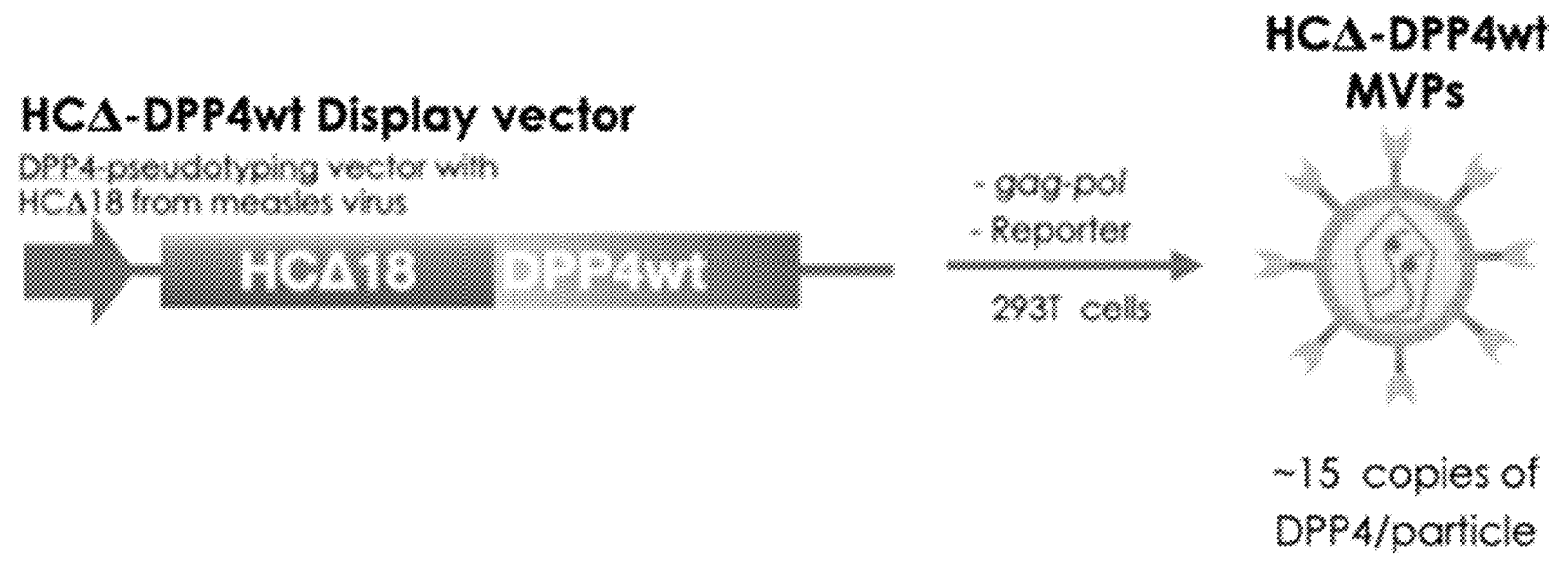
Figure 4B:
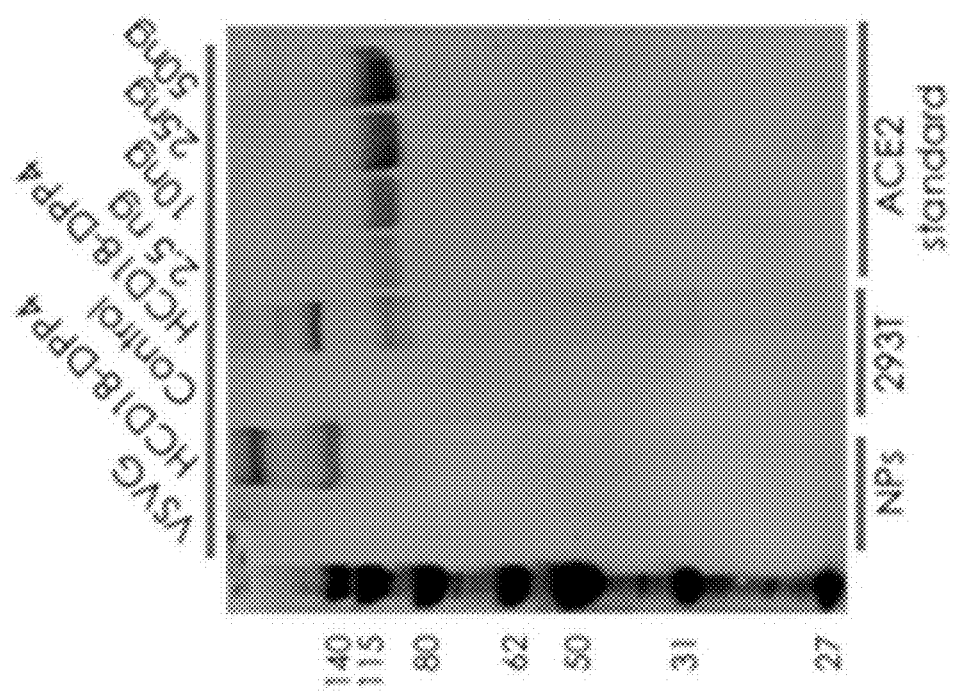
FIG. 4B depicts quantitative Western blot analysis of HCΔ-DPP4 valency of different multivalent particles.

The MERS coronavirus utilizes DPP4 as an entry receptor. To test whether a similar decoy-MVP strategy may be used to neutralize MERS viruses, DPP4-MVPs were generated by pseudotyping lentiviral particles with a fusion protein consisting of the membrane anchoring segment of a mutant version of hemagglutinin envelope protein from measles virus (HCΔ18) and the DPP4 extracellular domain (FIG. 4A). Both the measles envelope protein and DPP4 are type II transmembrane proteins. In the HCΔ-DPP4 pseudotyping construct, the N-terminus and transmembrane region of HCΔ18 were retained and the C-terminal region (extramembrane) was replaced with the corresponding region of the DPP4. DPP4-MVPs were generated by co-transfecting 293T cells with the HCΔ-DPP4 pseudotyping construct and a lentiviral packaging construct expressing essential lentiviral packaging components, such as Gag-Pol and Rev proteins, and a lentiviral genome transfer vector encoding a GFP/luciferase reporter. As determined by quantitative Western blot analyses (FIG. 4B), DPP4-MVPs displayed about 15 copies of HCΔ-DPP4 on the particles.

The neutralizing activities of DDP4-MVPs were tested against lentiviruses pseudotyped with MERS spike (MERS-PVPs) in a microneutralization assay using H1650 cells as target cells. The DPP4-MVP had an IC50 of 2.96±1.33 pM in the pseudovirus neutralization assay, whereas recombinant DPP4 had an IC50 of more than 48 nM (FIG. 4C). These results demonstrate that highly potent neutralizing MVPs against MERS coronaviruses can be generated by displaying multiple copies of a low-affinity type II entry receptor. Furthermore, the $IC_{50}$ of DPP4-MVPs in neutralizing live MERS coronavirus infection in a microneutralization assay will be assessed.

Finally, to further optimize the display of type II viral entry receptors, the display of DPP4 on lentiviral VLPs was tested by fusing the neuraminidase N-terminus and transmembrane regions with the DPP4 extracellular domain (FIG. 4D) to generate NA75-DPP4 MVPs accordingly. The NA75-DPP4 MVP had an $IC_{50}$ of 0.87 pM in pseudovirus neutralization assays (FIG. 4E). The results demonstrated that highly potent neutralizing decoy-MVPs could be generated against MERS coronaviruses by displaying multiple copies of a low-affinity type II entry receptor.

Figures 4D, 4E:
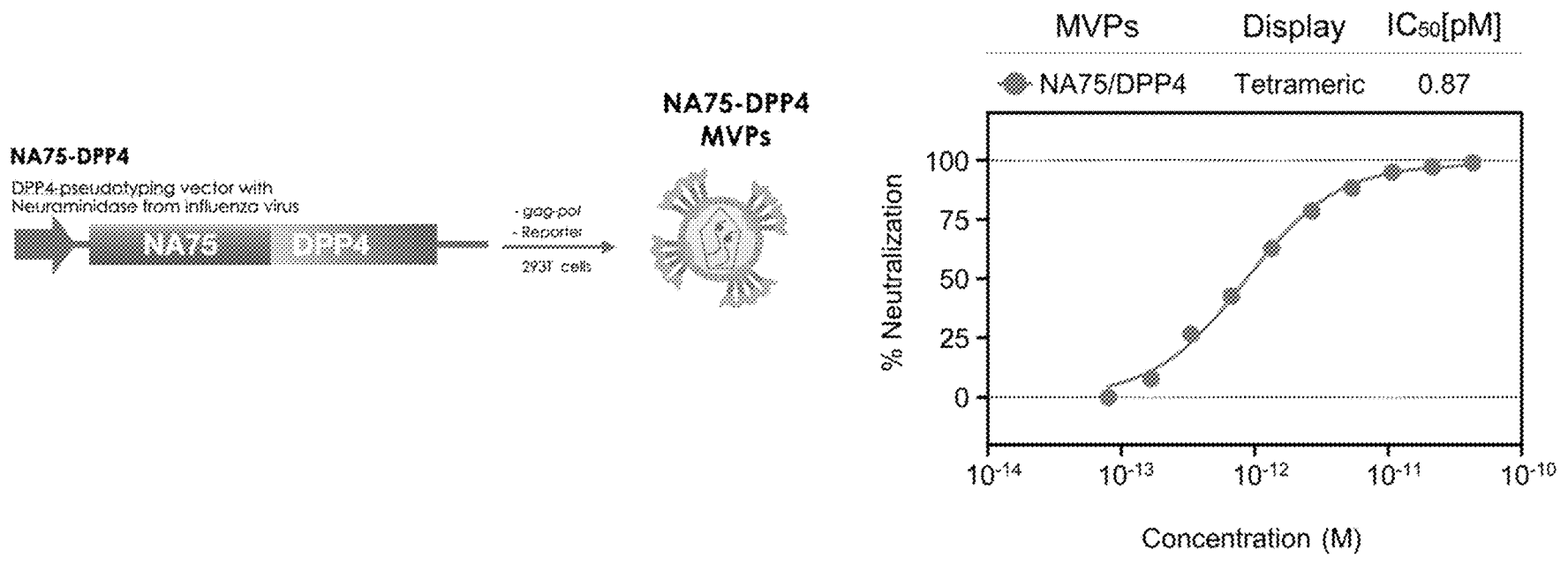

FIG. 4A-4E show the design and activity of DPP4-MVPs displaying multiple copies of decoy DPP4 receptors. FIG. 4A shows the design and production of HCΔ-DPP4-MVPs. The schematic illustrates the DPP4-displaying constructs with DPP4 extracellular domain fused to the HCΔ18 transmembrane domain from measles virus. HCΔ-DPP4 MVPs were generated by co-transfecting DPP4-displaying constructs with a lentiviral packaging construct and lentiviral reporter construct. FIG. 4B shows quantitative Western-blot analysis used to determine the copy number of DPP4 molecules on the HCΔ-DPP4 MVPs. FIG. 4C shows the neutralizing activities of various anti-MERS compounds, including DPP4 recombinant protein, and HCΔ-DPP4 MVPs were determined in a MERS pseudovirus infection assay using H1650 cells as target cells. FIG. 4D shows the design and production of NA75-DPP4 MVPs. The schematic illustrates the DPP4-displaying constructs with DPP4 extracellular domain fused to the neuraminidase transmembrane domain from influenza virus. NA75-DPP4 MVPs were generated by co-transfecting NA75-DPP4-displaying constructs with a lentiviral packaging construct and lentiviral reporter construct. FIG. 4E shows the neutralizing activities of NA75-DPP4 MVPs determined in a MERS pseudovirus infection assay using H1650 cells as target cells.

Example 5: The Reduced Neutralizing Potency of Decoy-MVPs Displaying Enzymatically Inactive ACE2

ACE2 is a critical regulator of human angiotensin systems. It lowers blood pressure by catalyzing the hydrolysis of angiotensin II, a vasoconstrictor, into angiotensin (1-7), a vasodilator. Human recombinant ACE2 has been tested in 89 healthy volunteers in a Phase I study and in patients with acute respiratory distress syndrome (ARDS) in a phase II study. Although a safety window can be established, the acute effects of active ACE2 on angiotensin (1-7) production and blood pressure present safety concerns for using ACE2 protein as a SARS CoV-2 neutralizing therapeutics. Moreover, mutations that disrupt the ACE2 catalytic function, such as H374A and H378A, also significantly reduce ACE2 binding to CoV-2 spike protein, thus potentially compromising the neutralization potential ACE2 neutralizing decoys against SARS CoV-2. To this end, decoy-MVPs displaying monomeric H2A/ACE2-VGTM was demonstrated to have an $IC_{50}$ of 377±79.4 fM, whereas decoy-MVPs displaying monomeric WT/ACE2-VGTM has an $IC_{50}$ of 211±93.7 fM, in a pseudovirus neutralization assay (FIG. 5). This result confirmed that the inactivating mutations do have some detrimental effects on the neutralizing function of ACE2-MVPs.

FIG. 5 shows that multivalent particles displaying enzymatic-inactive H2A-ACE2, designated as H2A/ACE2 MVPs, have a reduced neutralizing activity against CoV-2 pseudovirus. The neutralizing activities of the H2A/ACE2 MVPs and wild-type ACE2-MVPs were determined in a SARS CoV-2 pseudovirus infection assay using 293T/ACE2 cells as target cells.

Example 6: Decoy-MVPs with Oligomerized ACE2 Display have Enhanced Neutralizing Potency Notably, the ACE2-VGTM construct (FIG. 1A) could be used to display multiple copies of monomeric ACE2 molecules on the surface of MVPs based on Western-blot analyses. Although ACE2 MVP with monomeric ACE-VGTM was highly efficacious in neutralizing CoV-1 and CoV-2, the monomeric ACE2 display pattern did not match the trimeric display pattern of the spike protein. The effect of increasing the neutralizing potency of ACE2-MVPs was examined by generating MVPs displaying multivalent ACE2 with trimeric patterns matching to the spike proteins. Such design could further enhance the local avidity and multivalent interaction between spike trimers on the virus and ACE2 trimers on the decoy-MVP. With enhanced local avidity and binding, the detrimental effects of H2A mutations on the neutralizing function of ACE2 decoy-MVPs could be overcome.

Figures 6A, 6B, 6C:
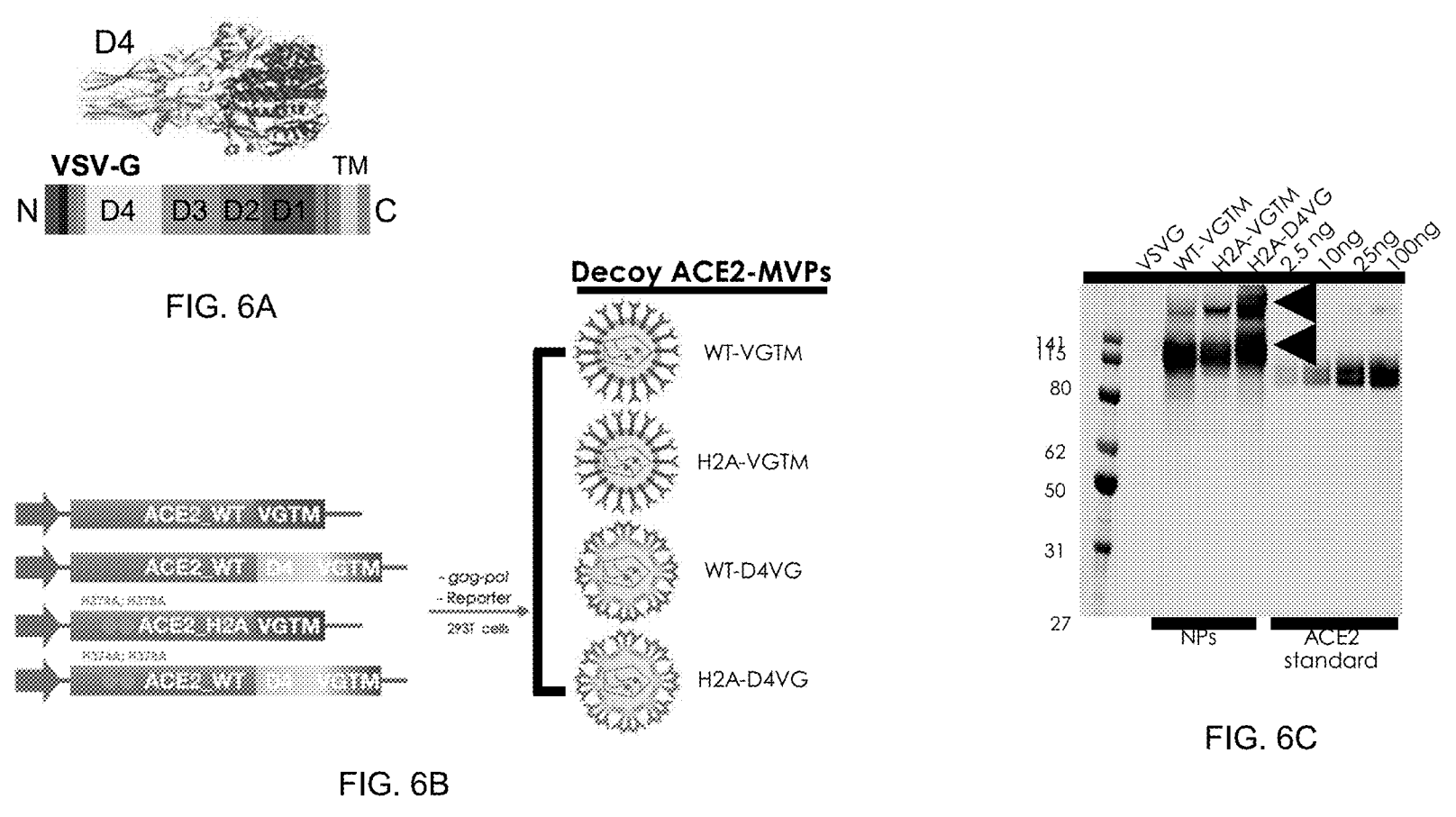
Figures 6D, 6E:
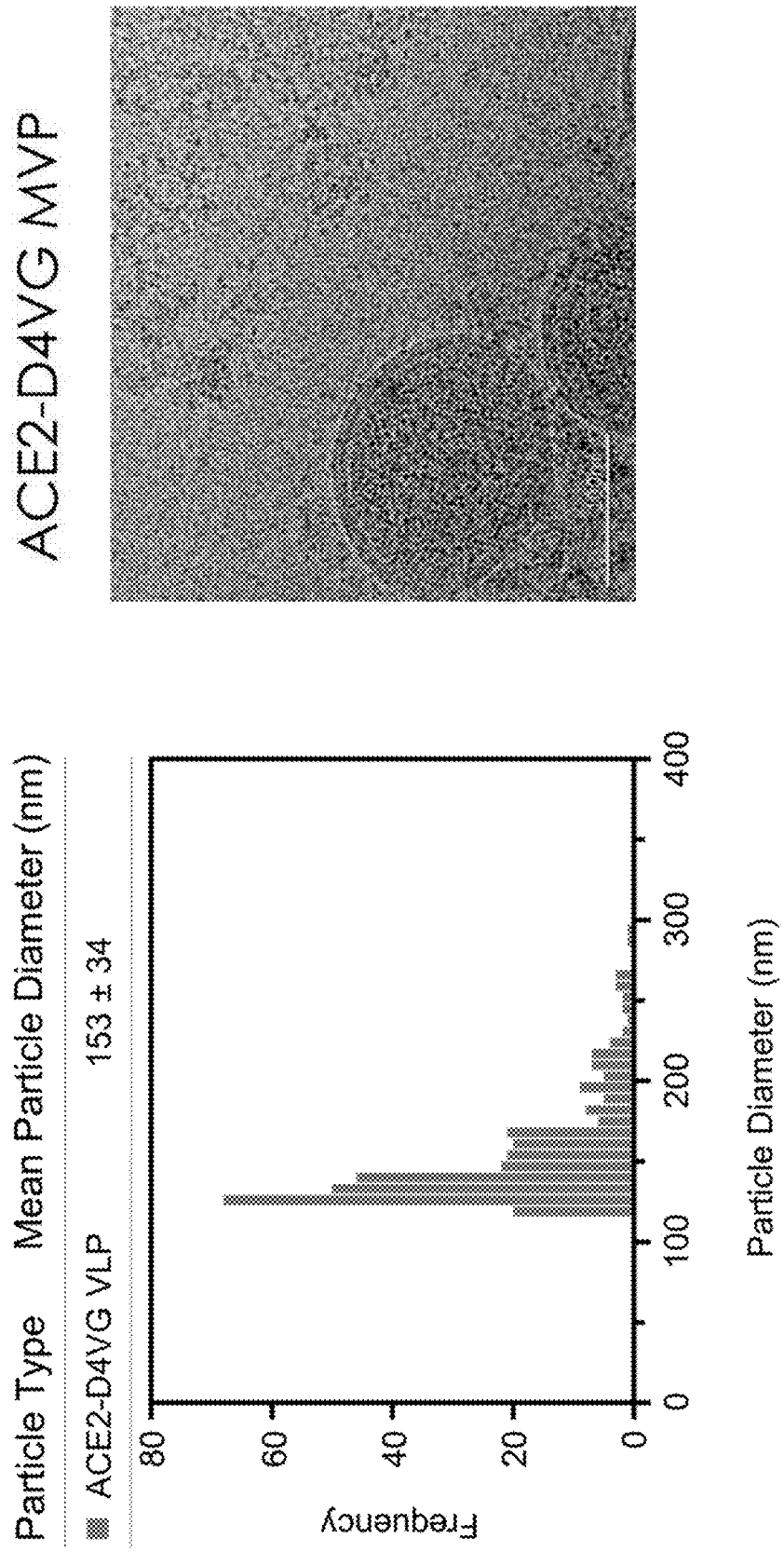

A D4 post-fusion trimerization domain from VSV-G protein (FIG. 6A) was used. A trimeric ACE2 display construct, designated as ACE2-D4VG, was designed to produce a fusion protein with the extracellular domain of ACE2, D4 trimerization domain, and VSVG transmembrane and cytosolic domain (FIG. 6B). Trimeric display constructs were generated that express with wild-type and enzymatically inactive ACE2 fusion proteins, designated as WT/ACE2-D4VG and H2A/ACE2-D4VG, respectively (FIG. 6B). Decoy-MVPs were produced by pseudotyping lentiviral viral-like particles (VLPs) with WT/ACE2-D4VG or H2A/ACE2-D4VG constructs via co-transfection of 293T cells with a ACE2-display construct, lentiviral packaging constructs encoding structural components, and a lentiviral genome transfer vector encoding a GFP reporter (FIG. 6B). ACE2-MVPs were purified, and their concentrations were determined by p24 ELISA analysis. Copy numbers and oligomeric configurations of ACE2 fusion proteins on MVPs were determined via quantitative Western blot and PAGE analysis (FIG. 6C). Trimeric ACE2-display constructs were found to be highly effective in displaying both wild-type ACE2 and H2A/ACE2. Notably, the ACE2-VGTM display constructs pseudotyped VLPs with primarily monomeric ACE2 fusion proteins, whereas ACE2-D4VG display constructs pseudotyped VLPs with high levels of oligomerized ACE2 (FIG. 6C). The average particle diameter of ACE2-D4VG MVPs was 153±34 nm as determined by tunable resistive pulse sensing analyses (TRPS) using qNano (FIG. 6D). The morphology of ACE2-D4VG MVPs were characterized by cryoEM analyses at nominal magnification of 150,000× (FIG. 6E).

FIG. 6A-6E shows the design, generation, and activity of oligomerized display of wild-type and enzymatically inactive ACE2 on multivalent particles. FIG. 6A shows the structure of post-fusion VSV-G with D4 domain as the trimerization domain. FIG. 6B shows a schematic illustrating the oligomerized ACE2-displaying constructs with ACE2 extracellular domain fused to the VSVG transmembrane domain (ACE2-VGTM) for monomeric display or fused to the D4 post-fusion trimerization domain and VSVG transmembrane domain (ACE2-D4VG) for trimeric display. Multivalent particles display constructs with wild-type ACE2 (WT-ACE2) and enzymatic-inactive ACE2 (H2A/ACE2) were generated by co-transfecting corresponding ACE2-displaying constructs with a lentiviral packaging construct and lentiviral reporter construct. FIG. 6C shows the copy number of ACE2 molecules on the ACE2-MVPs, which were determined by quantitative Western-blot analyses. FIG. 6D shows representative TRPS analysis of ACE2-D4VG MVPs. FIG. 6E shows a representative Electron Microscopy image of H2A/ACE2-D4VG MVPs at nominal magnification of 150,000×.

Figure 7A:
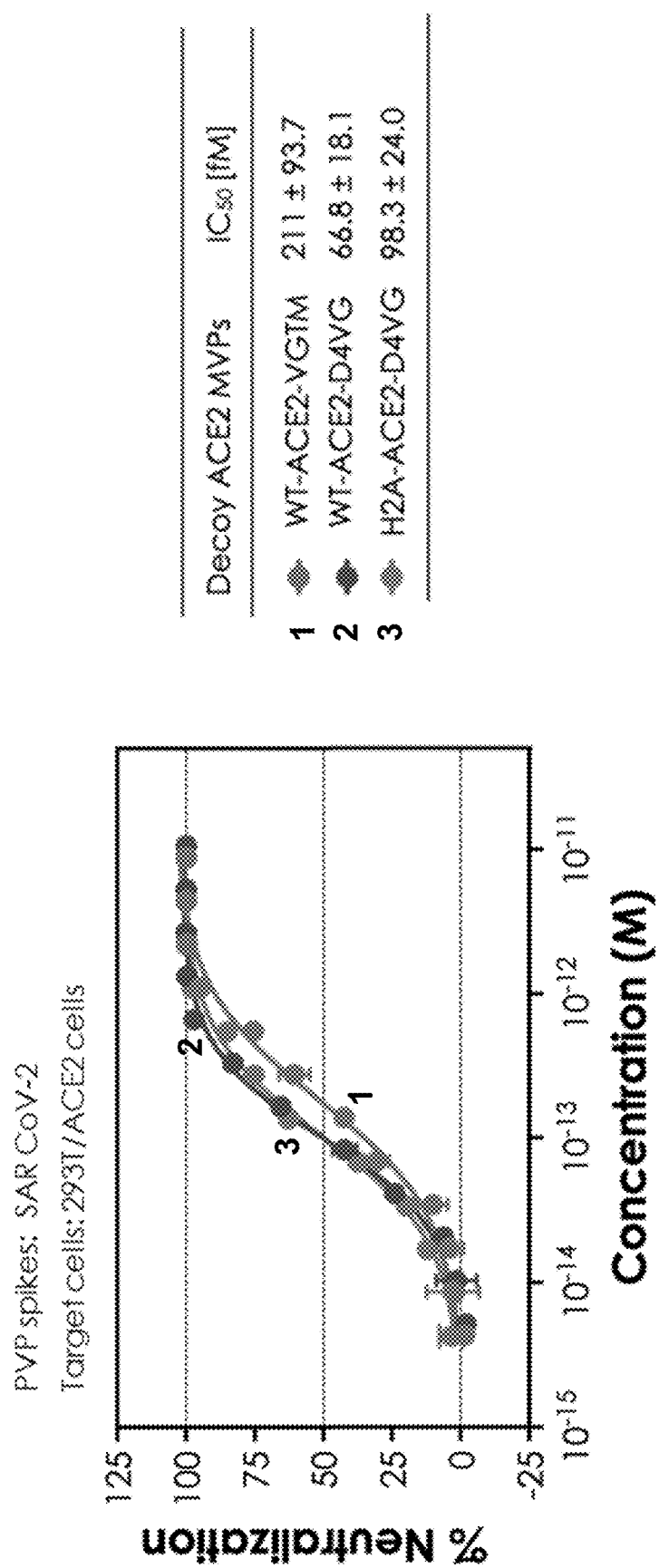

Example 7: Decoy-MVP Displaying Trimeric H2A/ACE2 is the Most Potent Inhibitors of SARS CoV-2 Viruses in Pseudovirus Neutralization Assays The neutralizing activity of both trimeric and monomeric ACE2-MVPs pseudotyped with wild-type and mutant H2A/ACE2 against SARS CoV-2 or CoV-1 in a pseudovirus neutralization assay was demonstrated, using 293T/ACE2 or VERO-E6 cells as target cells (FIG. 7A, B). Decoy-MVPs displaying trimeric WT/ACE2 and H2A/ACE were found to be both highly potent inhibitors, neutralizing CoV-2 pseudovirus at $IC_{50}$s of 66.8±18.1 fM and 98.3±24.0 fM, respectively. In contrast, decoy-MVPs pseudotyped with monomeric WT/ACE2 neutralize CoV-2 pseudovirus with $IC_{50}$s of 211±93.7 fM, an over 3-fold decrease in potency in comparison to their corresponding trimeric ACE2-MVPs (FIG. 5, FIG. 7A). MVPs displaying trimeric WT/ACE2 and H2A/ACE were shown to be both highly potent inhibitors, neutralizing CoV-1 pseudovirus at $IC_{50}$s of 204±73.7 fM and 428±87.6 fM, respectively. In contrast, MVPs pseudotyped with monomeric WT/ACE2 and H2A/ACE neutralize CoV-1 pseudovirus with $IC_{50}$s of 440±139 fM or 890±237 fM, an over 2-fold decrease in potency in comparison to their corresponding trimeric ACE2-MVPs (FIG. 5, FIG. 7B). These results demonstrated that MVPs with trimeric ACE2 display could further increase the neutralizing potency of WT and H2A mutant ACE2-MVPs against both CoV-2 and CoV-1 pseudoviruses.

Figure 7C:
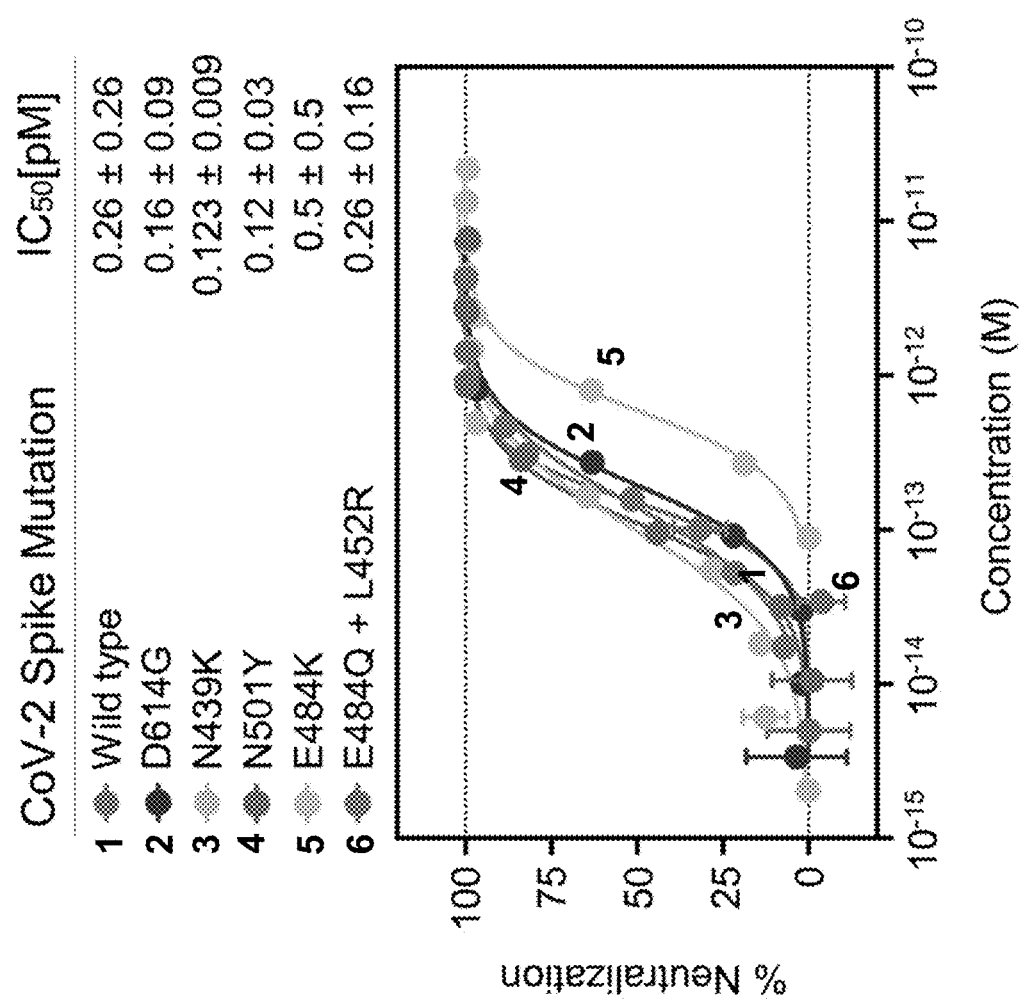

FIG. 7A-7C show the neutralizing activity of enzymatically inactive ACE2 through oligomerized display H2A/ACE2 on MVPs. FIG. 7A shows the neutralizing activities of ACE2-MVPs displaying wild-type ACE2 or enzymatically inactive H2A/ACE2-MVPs in monomeric or trimeric form, which were determined in a SARS CoV-2 pseudovirus infection assay using 293T/ACE2 cells as target cells. FIG. 7B shows the neutralizing activities of ACE2-MVPs displaying wild-type ACE2 or enzymatically inactive H2A/ACE2-MVPs in the monomeric or trimeric forms, which were determined in a SARS CoV-1 pseudovirus infection assay using VERO-E6 cells as target cells. FIG. 7C compares the neutralizing activities of the H2A/ACE2-D4VG MVPs against a variety of SARS CoV-2 variants in pseudovirus infection assay using 293T/ACE2 cells as target cells.

Figure 8B:
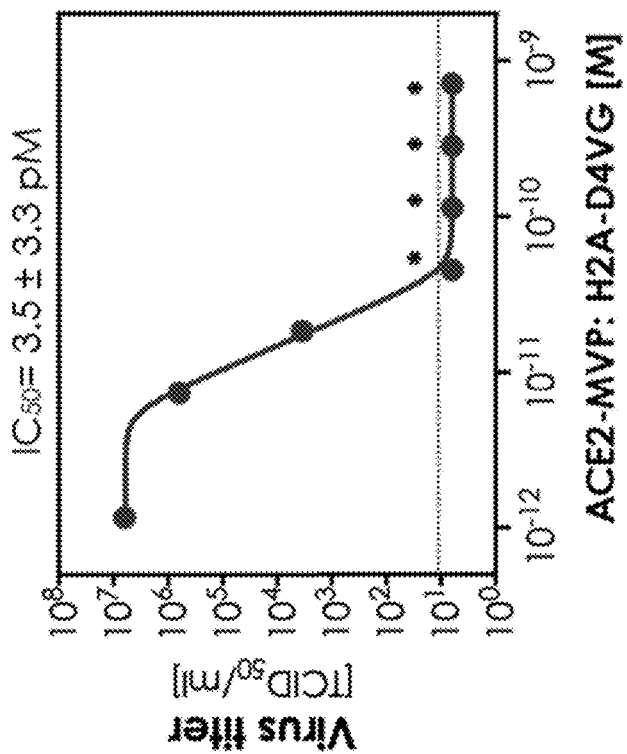
FIG. 8A-8B depict the antiviral activity of ACE2-MVPs in a premixed live SARS CoV-2 virus neutralization assay. The neutralizing activities of monomeric wild-type ACE2-MVP: WT-VGTM (FIG. 8A) and the trimeric enzymatically-inactive H2A/ACE2-MVP: H2A-D4VG were determined in a SARS CoV-2 live virus neutralization assay (FIG. 8B).
Figure 8A:
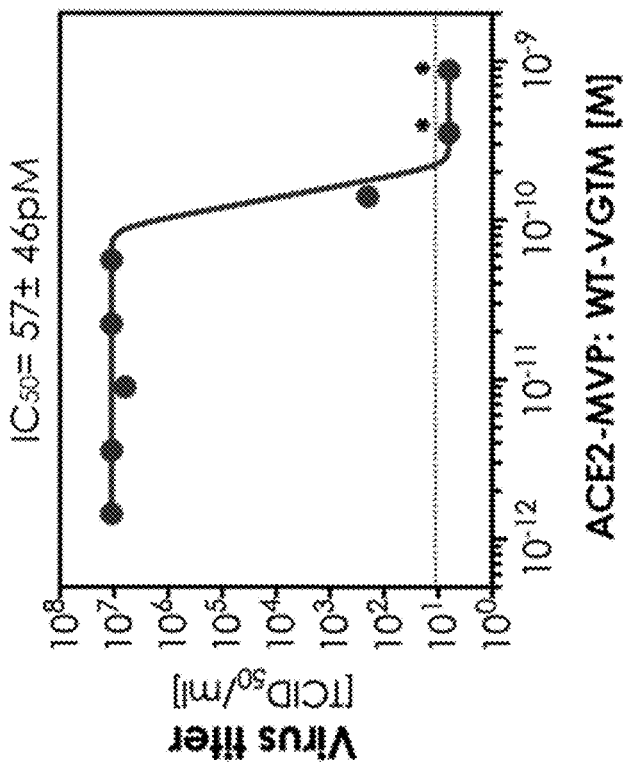

Example 8: Decoy-MVPs Displaying H2A/ACE2 are Potent Inhibitors Against Live SARS CoV-2 Viruses The neutralizing function of monomeric and trimeric ACE2-MVPs against live CoV-2 viruses was further characterized. Both monomeric and trimeric ACE2-MVPs were shown to reduce viral titer over six logs to an undetectable level in this microneutralization assay (FIG. 8A-8B). Notably, monomeric WT/ACE2-MVPs neutralize live CoV-2 virus at an $IC_{50}$ of 57±46 pM (FIG. 8A), whereas trimeric HA/ACE2-MVPs neutralize live CoV-2 virus at an $IC_{50}$ of 3.5±3.3 pM (FIG. 8B). These results demonstrated that oligomerized H2A/ACE2-MVPs were significantly more potent against live CoV-2 virus infection. Nevertheless, monomeric ACE2-MVPs were still highly potent inhibitors.

FIG. 8A-8B show the antiviral activity of ACE2-MVPs in a premixed live CoV-2 virus neutralization assay. FIG. 8A the neutralizing activities of monomeric wild-type ACE2-MVP (ACE2WT-VGTM MVP) determined using a SARS CoV-2 live virus neutralization assay. FIG. 8B shows the neutralizing activities of trimeric, enzymatically inactive H2A/ACE2-MVPs (H2A/ACE2-D4VG MVPs) determined using a SARS CoV-2 live virus neutralization assay.

Figures 9A, 9B:
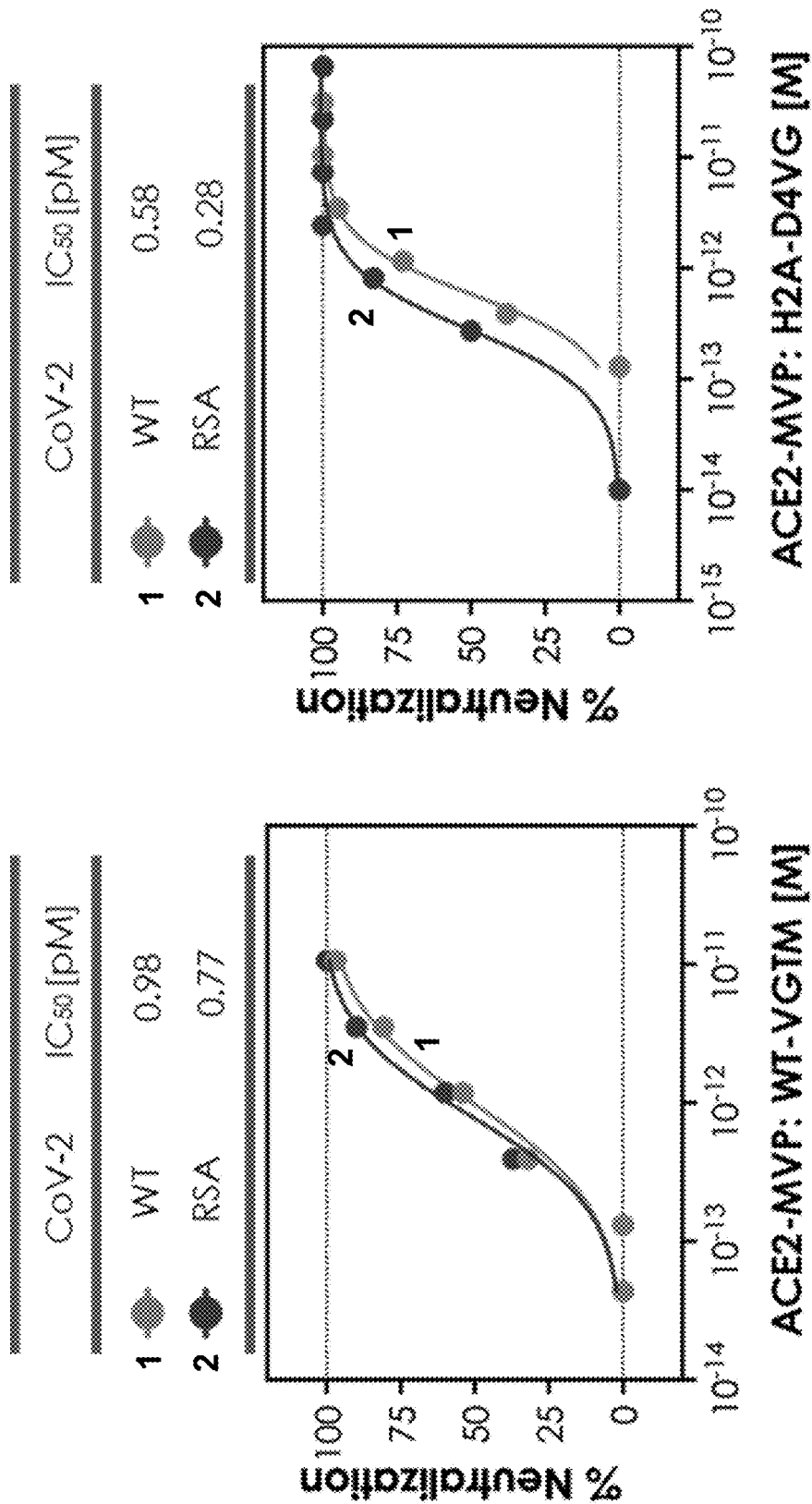
FIG. 9A-9B depict the neutralizing activity of trimeric H2A/ACE2-MVPs against live wild-type SARS CoV-2 (FIG. 9A) or South Africa variant SARS CoV-2 were determined via PRNT assay (FIG. 9B).

H2A/ACE2 Decoy-MVPs effectively neutralize B.1.351 South Africa variant in PRNT: Whether monomeric WT/ACE2-MVPs and trimeric H2A/ACE2-MVPs could effectively neutralize the B.1.351 South Africa strain of live CoV-2 containing E484K and N501Y mutations in a PRNT assay was further examined (FIG. 9A-9B). Monomeric WT/ACE2-MVPs neutralized both the original USA-WA1/2020 strain and South Africa B.1.351 strain at $IC_{50}$s of 0.98 pM and 0.77 pM, respectively (FIG. 9A). In comparison, trimeric H2A/ACE2-MVPs neutralized both the original USA-WA1/2020 strain and South Africa B.1.351 stain at 0.58 pM and 0.28 pM, respectively (FIG. 9B). Notably, both monomeric WT/ACE2-MVPs and trimeric H2A/ACE2-MVPs were comparable or have slightly higher potency against the South Africa B.1.351 strain in the PRNT assay. Moreover, trimeric H2A/ACE2-MVPs consistently outperform monomeric WT/ACE2-MVPs in the live virus neutralization assay. Clearly, both monomeric ACE2-MVPs and trimeric H2A/ACE2-MVPs were highly potent inhibitors against the original USA-WA1/2020 strain and South Africa B.1.351 strain one of the key variants of concern in the ongoing pandemic, offering another critical advantage over neutralizing antibodies.

FIG. 9A shows the neutralizing activities of ACE2-MVPs displaying monomeric wild-type ACE2 against the original Washington strain of SARS CoV-2 or the South Africa variant of SARS CoV-2 in a live virus PRNT assay. FIG. 9B shows the neutralizing activities of ACE2-MVPs displaying trimeric H2A/ACE2 against the original Washington strain of SARS CoV-2 or the South Africa variant of SARS CoV-2 in a live virus PRNT assay.

Figure 10B:
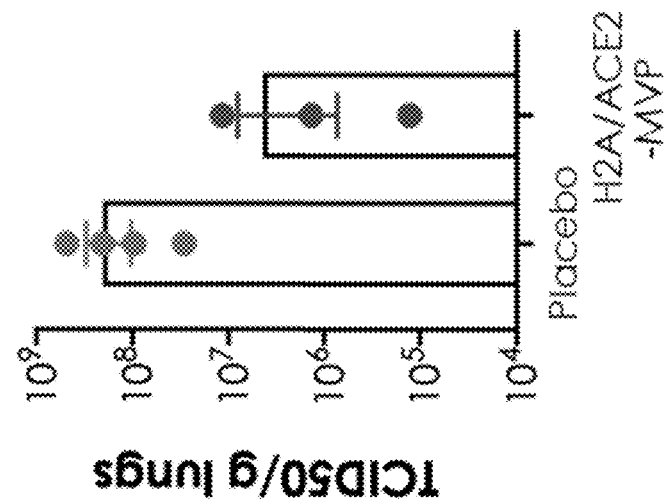
FIG. 10A-10B depict the efficacy of trimeric H2A/ACE2-MVPs in post-exposure treatment of SARS CoV-2 live virus infection in the hamsters.

Example 9: Decoy-MVPs Displaying H2A/ACE2 are Potent Inhibitors of Live SARS CoV-2 Viruses in Hamsters Golden hamsters inoculated with CoV-2 virus closely mimic more severe disease in humans. Affected hamsters develop readily observable clinical symptoms, including rapid weight loss accompanied by a very high viral load in the lungs and severe lung histology. To evaluate the ability of H2A/ACE2-MVPs to treated infected animals, hamsters were challenged with $2.3 \times 10^4$ Pfu SARS CoV-2 virus and then treated hamsters with $1 \times 10^{11}$ particles of H2A/ACE2-MVPs through IN delivery. The treatments were started at 4 hours post virus challenging and given twice/day for a total of five doses. H2A/ACE2-MVPs treatments were observed to have significantly reduced weight loss from the challenged hamsters (FIG. 10A) and furthermore reduced viral load in lungs by more than one log (FIG. 10B). In summary, the hamster study demonstrated that H2A/ACE2-MVPs have potent neutralizing and therapeutic effects against CoV-2 infection in hamsters.

Figure 10A:
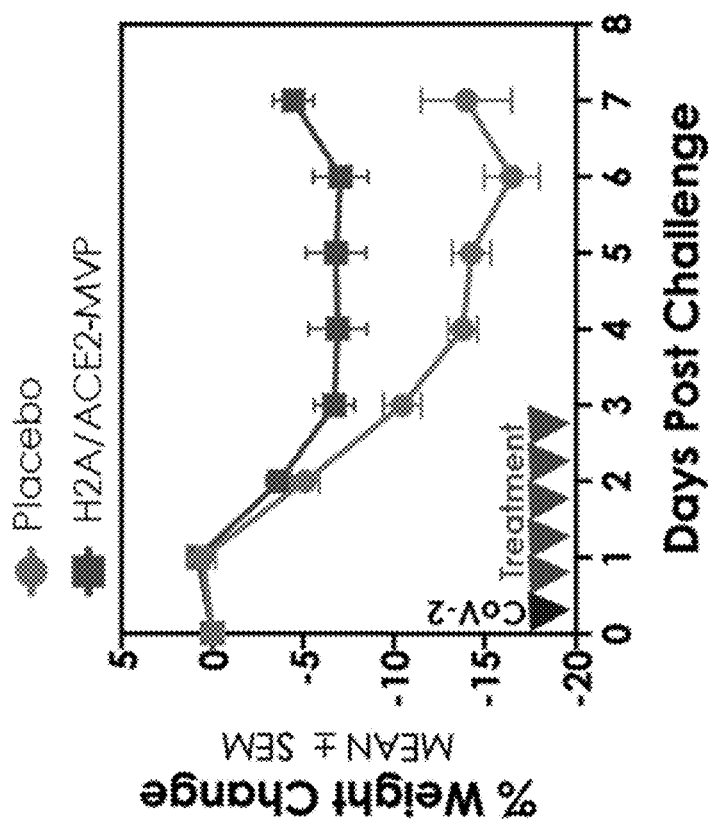

FIG. 10A shows the effect of trimeric H2A/ACE-MVPs in post-exposure treatment of SARS CoV-2 live virus infection on weight loss in hamsters. FIG. 10B shows the effect of trimeric H2A/ACE-MVPs in post-exposure treatment of SARS CoV-2 live virus infection on viral loads in lungs in hamsters.

Example 10: Treatment with ACE2-MVPs Effectively Rescue Mice from Lethal Infection by SARS CoV-2

SARS CoV-2 infection causes lethality in the K18-hACE2 transgenic mice and induces symptoms and pathology recapitulating many of the defining features of severe COVID-19 in humans. High viral titer in lungs, with spread to brain and other organs, is observed in infected mice, coinciding with massive upregulation of inflammatory cytokines and infiltration of monocytes, neutrophils and activated T cells. This model has been used to test the efficacy of vaccine and therapeutics in preventing SARS-CoV-2 induced lethal infection.

Figure 11B:
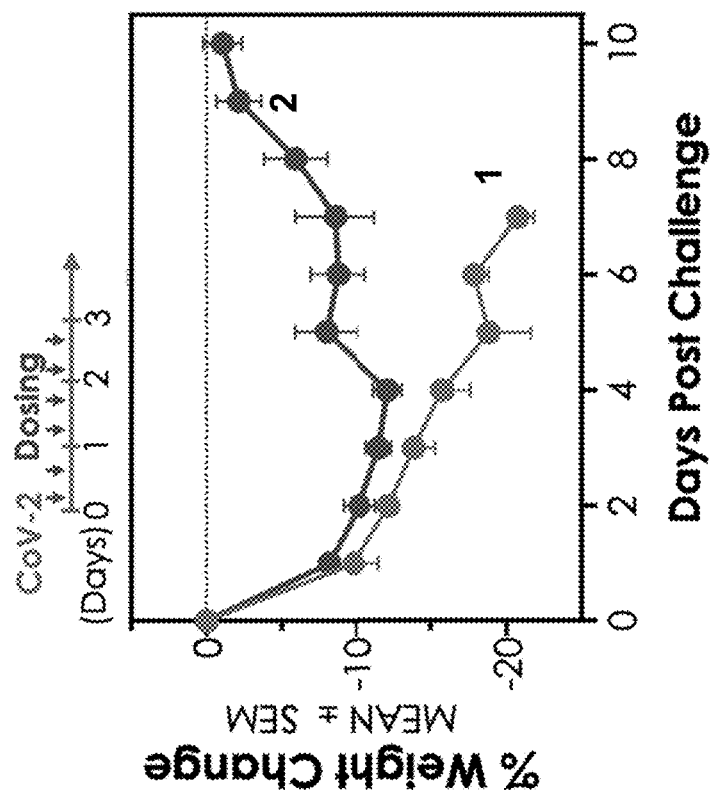
FIG. 11A-11B shows the efficacy of trimeric H2A/ACE-MVPs in post-exposure treatment of SARS CoV-2 live virus and variant infection in the hACE2 transgenic mice.

Whether IN delivery of ACE2-MVPs could protect ACE2 transgenic mice from SARS CoV-2 infection-related symptoms and lethality was investigated. K18-hACE2 mice were challenged with 2800 pfu of SARS CoV-2 (Strain USA-WA1/2020) and treated with 5 doses of H2A/ACE2-D4VG MVPs ($1 \times 10^{11}$ particles per dose) delivered IN. Dosing began 4-hours post-infection, and subsequent doses were given twice a day at day 1 and day 2 post-infection. Mice in the treatment group exhibited no respiratory symptoms and all survived the infection (FIG. 11A), whereas all mice in the placebo group succumbed to infection at approximately day 6 post-infection. Moreover, in comparison to the placebo group, mice in the treatment group experienced modest or no respiratory symptoms and only transitory weight loss (FIG. 11B). The results demonstrated that H2A/ACE2 MVPs could rescue lethal SARS CoV-2 infection and completely prevent respiratory symptoms in the K18-hACE2 transgenic mouse model, a model recapitulating severe COVID-19 in humans.

Furthermore, whether IN delivery of ACE2-MVPs protected ACE2 transgenic mice from Delta variant infection-related symptoms and lethality was also investigated. K18-hACE2 mice were challenged with 800 pfu of SARS CoV-2 (Delta variant NR55674) and treated with 5 doses of H2A/ACE2-D4VG MVPs ($1 \times 10^{11}$ particles per dose) delivered IN. Again, dosing began 4-hours post-infection, and subsequent doses were given twice a day at day 1 and day 2 post-infection. Mice in the treatment group exhibited no respiratory symptoms and all but one survived the infection (FIG. 11C), whereas all mice in the placebo group succumbed to infection at approximately day 6 post-infection. Moreover, in comparison to the placebo group, the five surviving mice in the treatment group experienced modest or no respiratory symptoms and only transitory weight loss (FIG. 11D). Thus, H2A/ACE2 MVPs rescued lethal SARS CoV-2 Delta variant infection and largely prevented respiratory symptoms in the K18-hACE2 transgenic mouse model, demonstrating that ACE2-MVPs potentially can be used as therapeutics against all SARS CoV-2 variants utilizing ACE2 as an entry receptor.

Figure 11A:
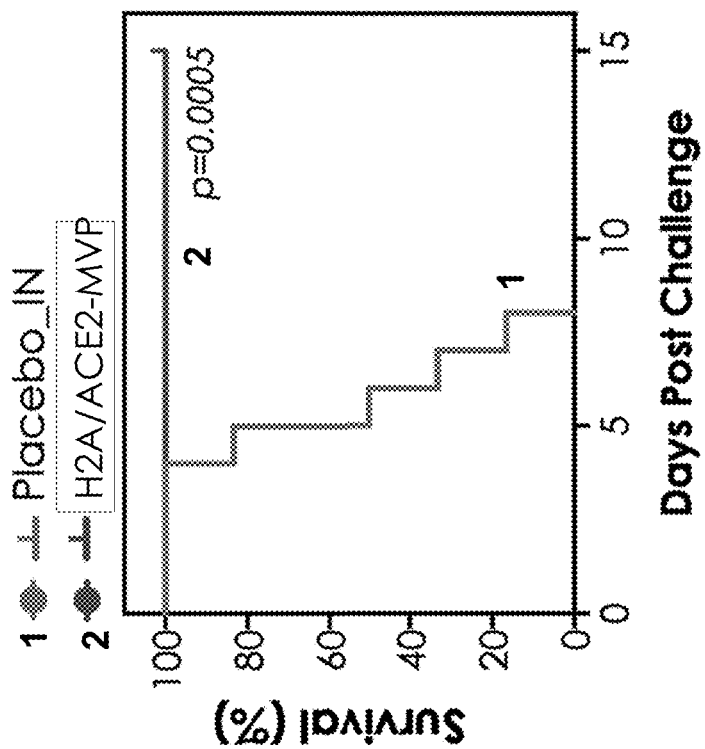
Figures 11C, 11D:
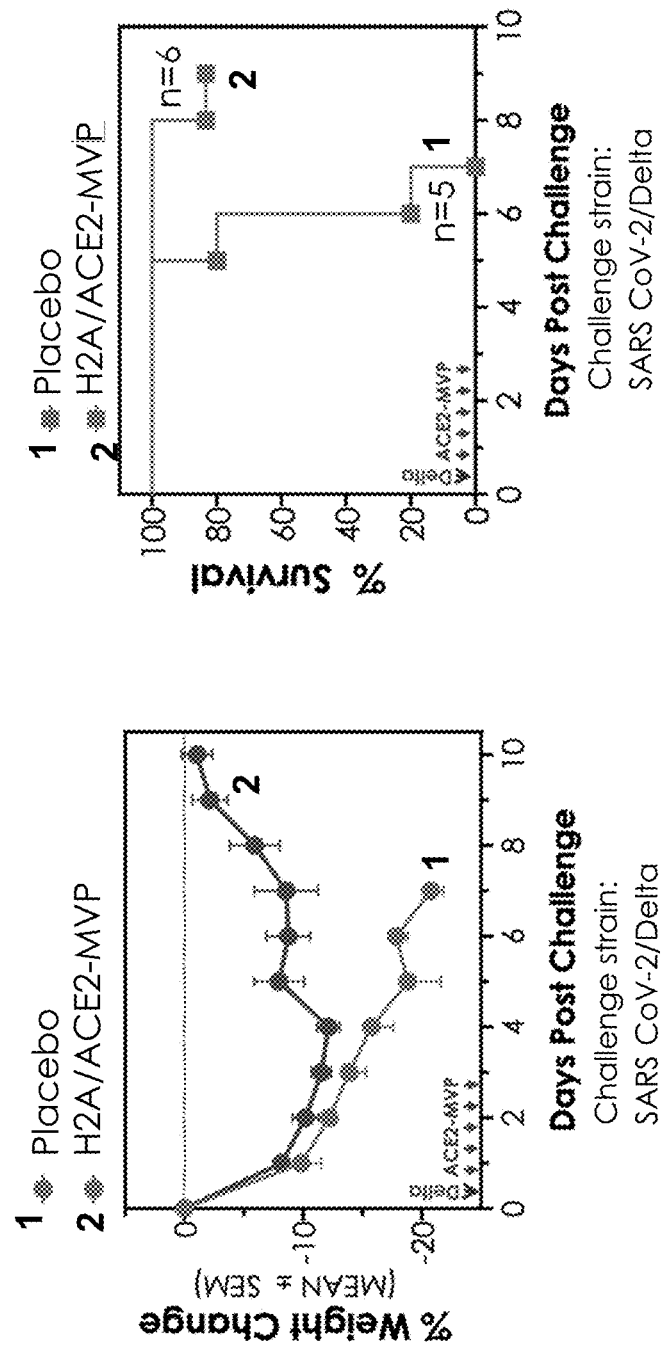
FIG. 11C depicts the effect of trimeric H2A/ACE2-MVPs treatment on survival of SARS CoV-2 Delta variant infected hACE2 transgenic mice.
FIG. 11D shows the effects of the weight loss in hACE2 transgenic mice infected with the SARS CoV-2 Delta variant.

FIG. 11A-11B show the efficacy of trimeric H2A/ACE-MVPs in post-exposure treatment of SARS CoV-2 live virus infection in the hACE2 transgenic mice. FIG. 11A shows the effect of trimeric H2A/ACE-MVPs treatment on survival in ACE2 mice challenged with the WA strain of SARS CoV-2. FIG. 11B shows the effect of trimeric H2A/ACE2 MVPs treatment on weight loss in ACE2 mice challenged with the WA strain of SARS CoV-2. FIG. 11C depicts the effect of trimeric H2A/ACE-MVPs treatment on survival of SARS CoV-2 Delta variant infected hACE2 transgenic mice. FIG. 11D shows the effects of the weight loss in hACE2 transgenic mice infected with the SARS CoV-2 Delta variant.

Example 11: ACE2-MVP Treatment of SARS CoV-2 Infection Induces Robust Immunity Against Dominant Delta Variant To examine how decoy-MVP treatment of SARS CoV-2 may affect the development of antiviral immunity post-infection, we re-challenged the hACE2 mice rescued from primary infection with various strains of SARS CoV-2 30 days after the initial infection. First, mice were challenged with the original SARS CoV-2 strain, the same virus strain using in the primary infection. No noticeable respiratory symptoms, weight loss (FIG. 12A), or death (FIG. 12B) were observed in the re-challenged survivors. Further, another group of hACE2 mice rescued from primary infection with the Delta variant of SARS CoV-2 were re-challenged at about 9000 Pfu, a viral dosage that was at least three times higher than virus dosage used in the primary infection. Again, no noticeable respiratory symptoms, weight loss (FIG. 12C), or death (FIG. 12D) were observed. Notably, ACE2-MVP treatment of SARS CoV-2 infected hACE2 mice not only rescued these mice from lethal infection and eliminated all respiratory symptoms through drastically reduction peak viral load in these mice. Nevertheless, these mice developed robust immunity against both the original SARS CoV-2 strain as well as the Delta variant. Thus, hACE2 mice surviving primary challenge as a result of ACE2-MVP treatment developed robust immunity against the original SARS CoV-2 strain as well as the Delta variant.

Figure 12B:
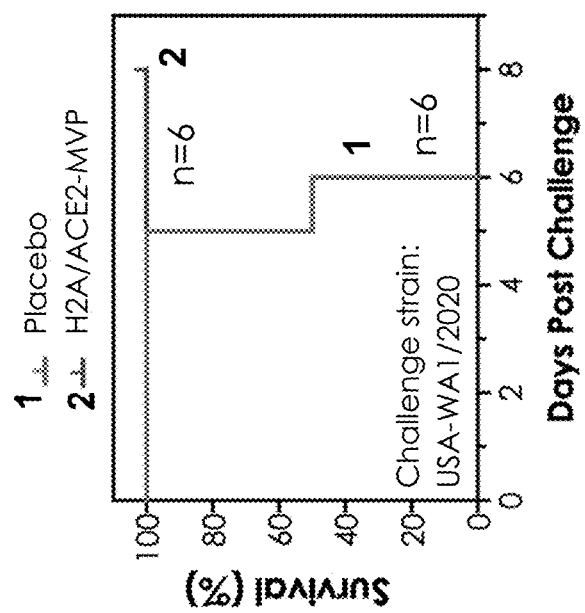
FIG. 12A-12D show that the hACE2 transgenic mice rescued from primary SARS CoV-2 infection with trimeric H2A/ACE2-MVP treatments are resistant to re-infection with either the original SARS CoV-2 strain or the Delta variant strain.
Figure 12A:
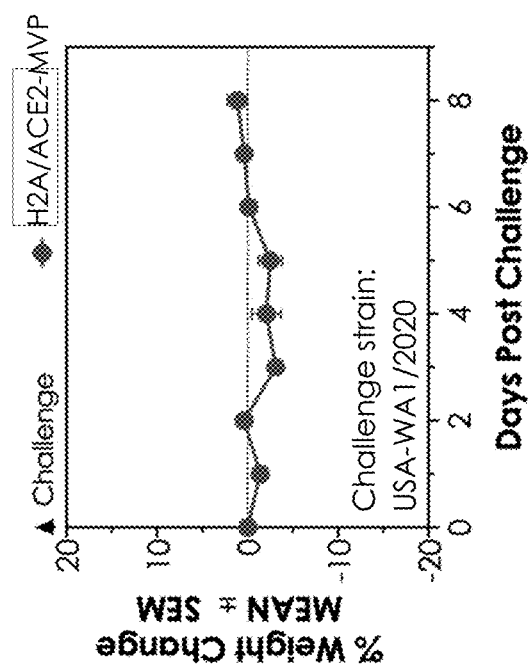
Figure 12D:
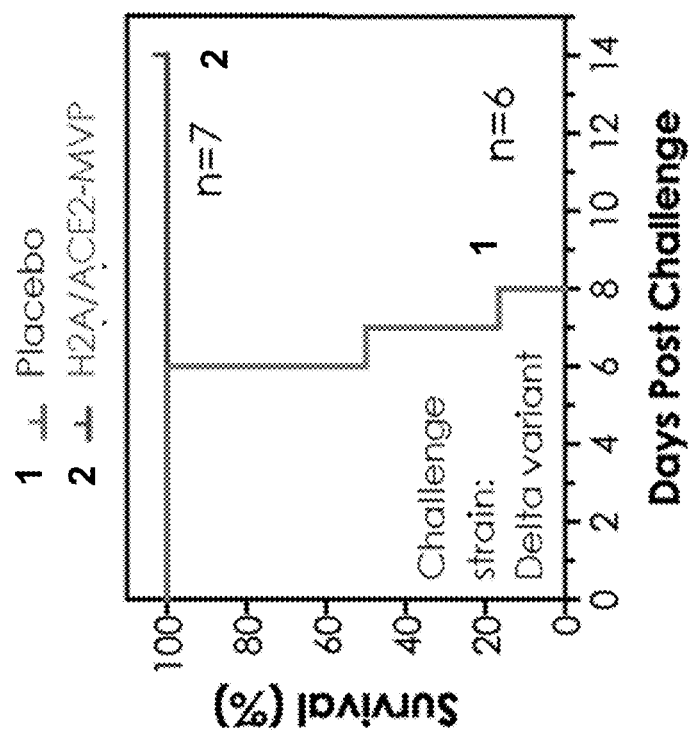
Figure 12C:
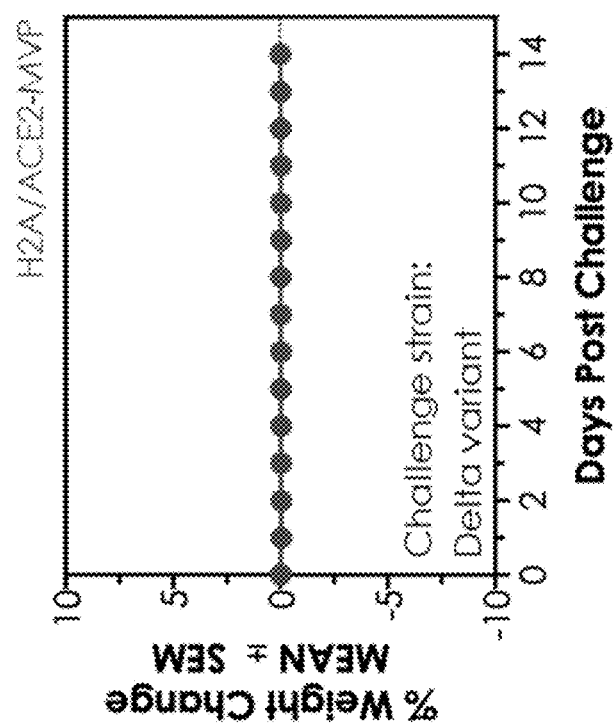

FIG. 12A-12D show that ACE2 mice rescued by the H2A/ACE2-D4VG MVP were resistant to re-challenge with the original SARS CoV-2 strain as well as the Delta variant. ACE2 mice survived from primary SARS CoV-2 challenge with trimeric H2A/ACE2 MVPs were challenged again with the original SARS CoV-2 strain as well as the Delta variant. FIG. 12A shows the effect of SARS CoV-2 re-challenge on body weight of ACE2 transgenic mice. FIG. 12B shows the effect of SARS CoV-2 re-challenge on survival of ACE2 transgenic mice. FIG. 12C shows the effect of Delta variant re-challenge on body weight of ACE2 transgenic mice. FIG. 12D shows the effect of Delta variant re-challenge on survival of ACE2 transgenic mice.

Figure 13D:
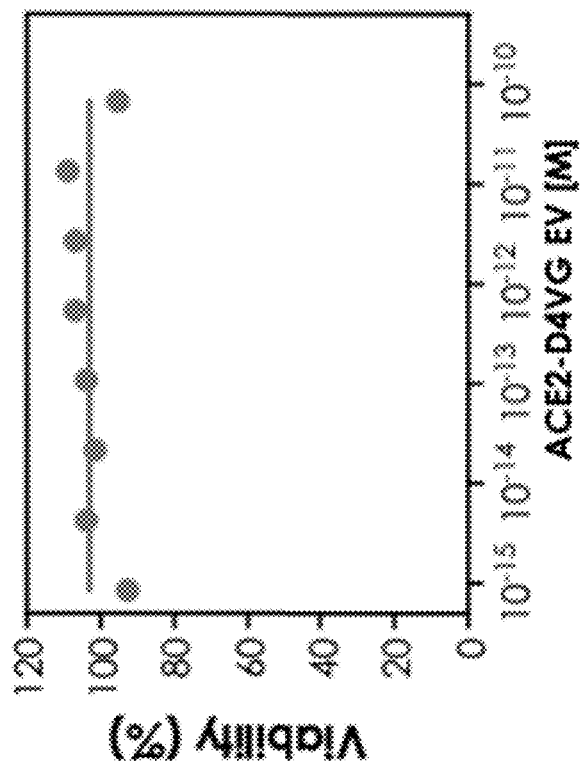

Example 12: EV-Based ACE2-MVPs are Highly Potent Inhibitors Against Live CoV-2 Viruses By transfecting 293T cells with only the trimeric decoy-receptor displaying vector (FIG. 6A) without the lentiviral packaging vector, EVs displaying multiple copies of ACE2 were generated, designated EV-based ACE2-MVPs. The mean diameter of EV-based ACE2-MVPs was 131±29 nm as determined by TRPS analysis (FIG. 13A). Moreover, EVs displaying trimeric H2A/ACE2 were highly potent inhibitors, neutralizing CoV-2 pseudovirus at $IC_{50}$s of 26±12 fM. Furthermore, trimeric EV-based ACE2-MVPs neutralized live CoV-2 virus at an $IC_{50}$ of 14 pM in post-infection live CoV-2 microneutralization assays and reduced viral titer by over five logs (FIG. 13C) without noticeable cytotoxicity (FIG. 13D). The results demonstrate that EV-based ACE2-MVPs were highly potent neutralizers of SARS CoV-2.

Figure 13C:
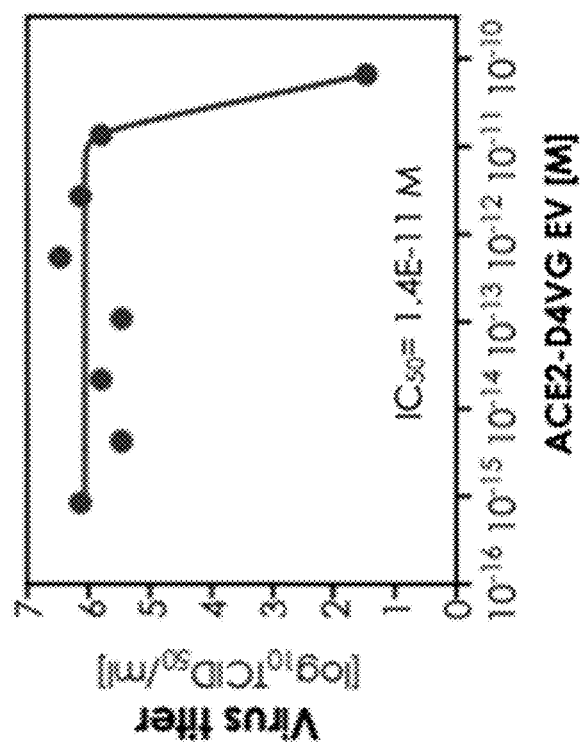

FIG. 13A-13D show particle analysis and in vitro neutralizing efficacy of EV-based ACE2-MVPs. FIG. 13A shows particle size distribution of EV-based ACE2-MVPs as determined by Tunable Resistive Pulse Sensing Analysis using a qNano instrument. FIG. 13B shows the neutralizing activity of EV-based ACE2-MVPs determined in a SARS CoV-2 pseudovirus infection assay using 293T/ACE2 cells as target cells. FIG. 13C shows the neutralizing activity of EV-based ACE2-MVPs as determined in a SARS CoV-2 live virus neutralization assay. FIG. 13D shows the cytotoxicity of EV-based ACE2-MVPs as determined in a SARS CoV-2 live virus neutralization assay.

Example 13: Design Strategy of Decoy-MVP Display Vector

The results presented above demonstrate that decoy-MVPs are a novel class of highly potent antivirals against pandemic viruses. Decoy-MVPs were designed to be the mirror image of its targeting virus and display the viral-entry receptors that match to the oligomeric multivalent spike proteins on the virus envelope. Two different types of enveloped particle display vectors were prepared for efficient protein display on VLP and extracellular vesicles (EV).

Figure 14A:
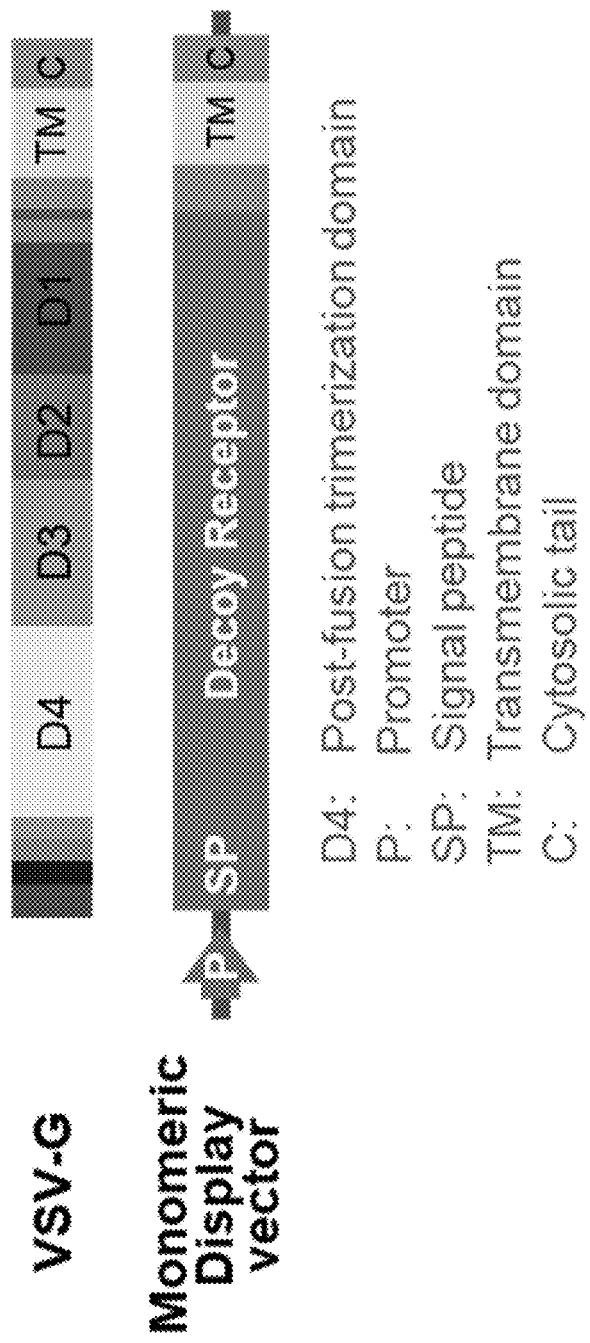
FIG. 14A illustrates vector design for a monomeric display vector expressing a fusion protein consisting of a protein linked to the VSVG transmembrane and intracellular domains.
Figure 14B:
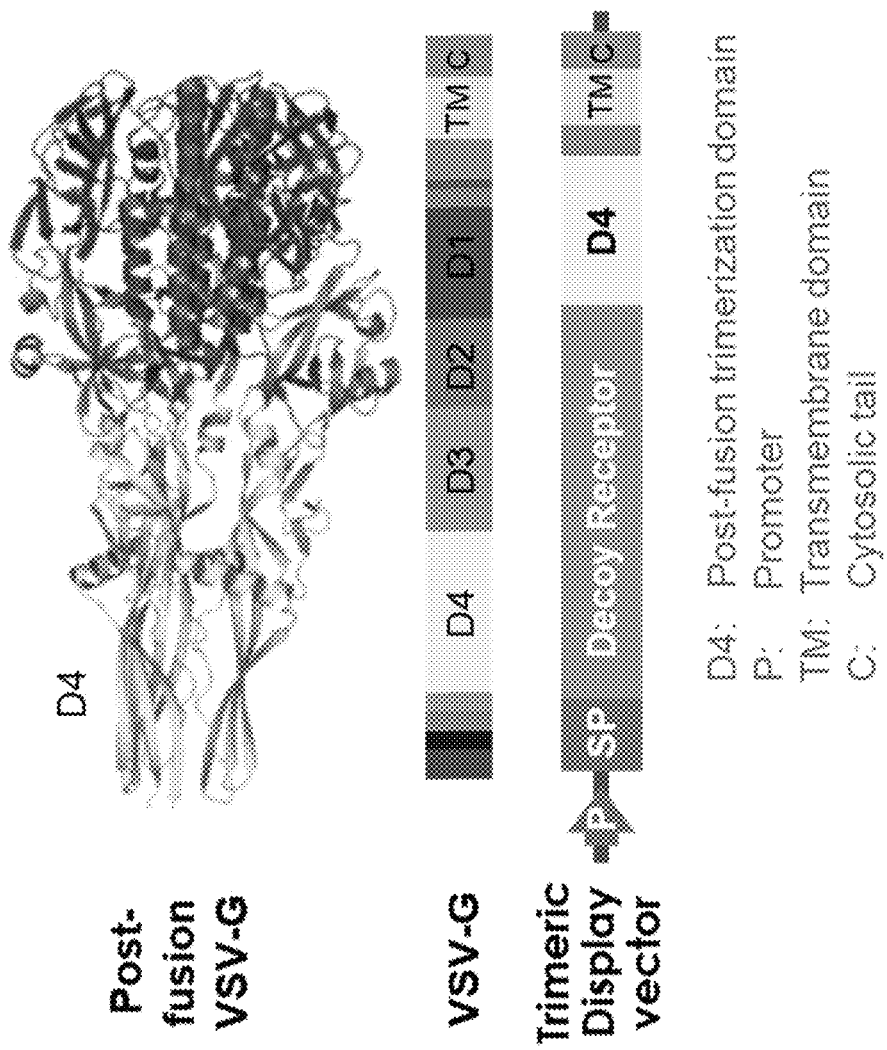
FIG. 14B illustrates vector design for a trimeric display vector expressing a fusion protein consisting of a protein linked to the D4 post-fusion trimerization domain of VSVG, followed by the transmembrane and intracellular domains of VSVG.

A monomeric display vector expressing a fusion protein consisting of the extracellular domain of a viral entry receptor decoy linked to the VSVG transmembrane and intracellular domains is designed as shown in FIG. 14A to display hundreds of copies of monomeric proteins on the surface of VLPs and EVs. Aside from the use of monomeric formats that are suited to form high avidity interactions with similarly multivalently displayed patterned viral spike proteins, enveloped particles are made to match oligomeric display formats of viral spike proteins to further enhance avidity at the level of individual oligomeric binding partners. To this end, a trimeric display vector expressing a fusion protein consisting of the extracellular domain of a viral entry receptor decoy linked to the D4 post-fusion trimerization domain of VSVG, followed by the transmembrane and intracellular domains of VSVG is designed as shown in FIG. 14B. The vector is used to display hundreds of copies of trimeric proteins on the surface of VLPs and EVs and are well suited to form high avidity interactions with similarly oligomeric proteins on the viral envelope.

FIG. 14A-14B show vectors for multivalent displaying of decoy viral entry receptors on enveloped particles in varied oligomeric format. FIG. 14A shows a monomeric display of viral entry receptors on enveloped particles by using a vector expressing a fusion protein consisting of a decoy viral entry receptor linked to the VSVG transmembrane and intracellular domains. FIG. 14B shows a trimeric or oligomeric display of viral entry receptors on enveloped particles by using a vector expressing a fusion protein consisting of a protein linked to the D4 post-fusion trimerization domain of VSVG, followed by the transmembrane and intracellular domains of VSVG.

Example 14: Generation of Monomeric Decoy-MVPs

Figure 15A:
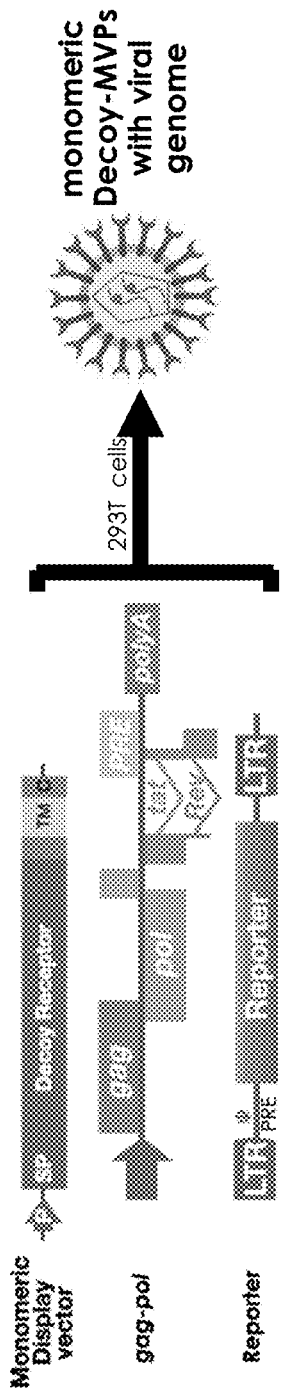
FIG. 15A-15C illustrate generation of monomeric enveloped particles.
Figure 15B:
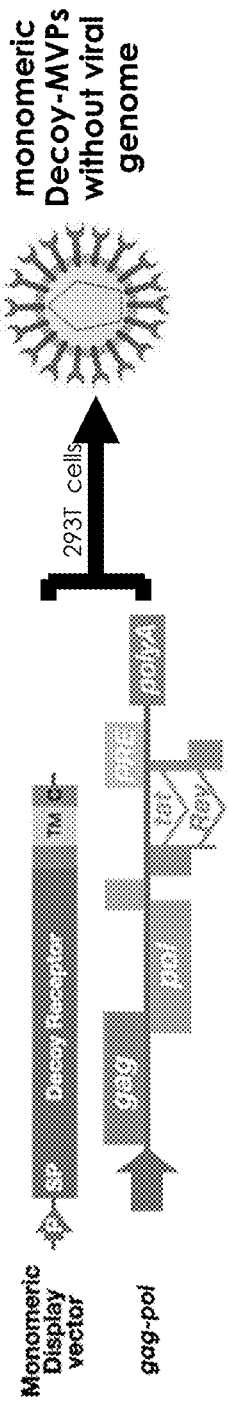
Figure 15C:
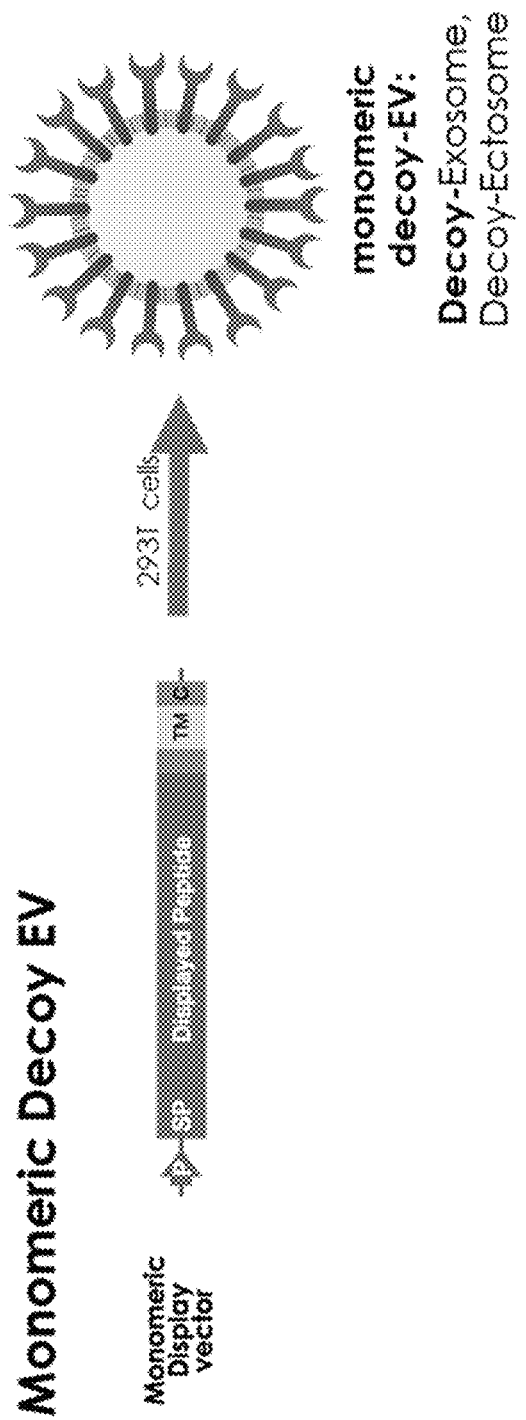
Figure 16A:
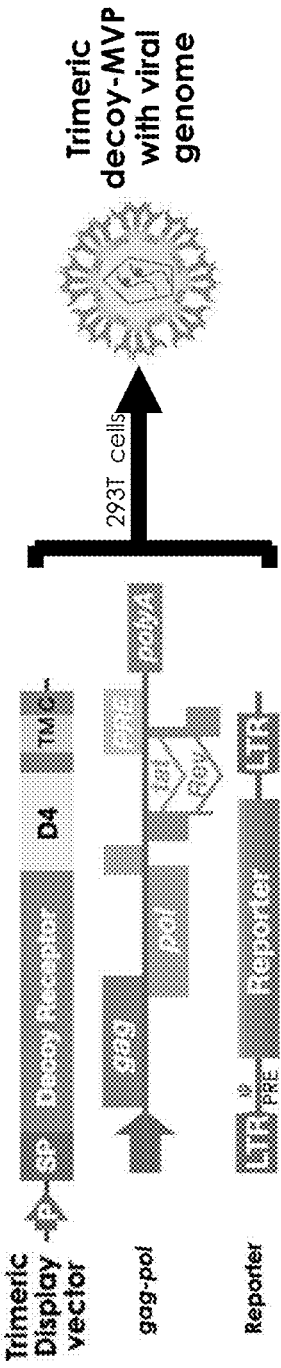
FIG. 16A-16C illustrate generation of trimeric enveloped particles.
Figure 16B:
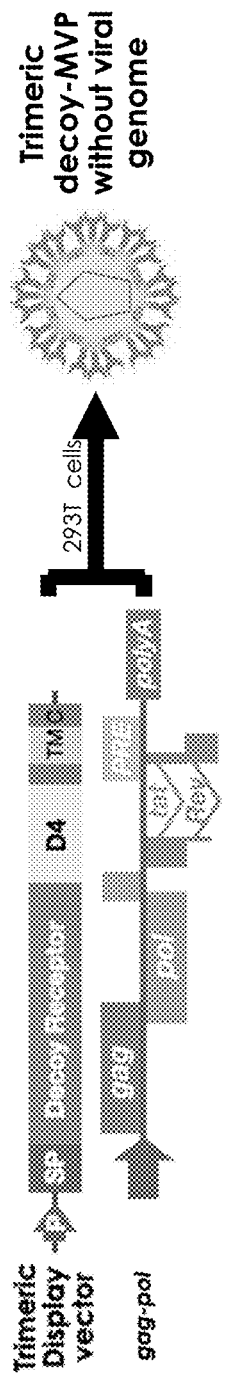
Figure 16C:
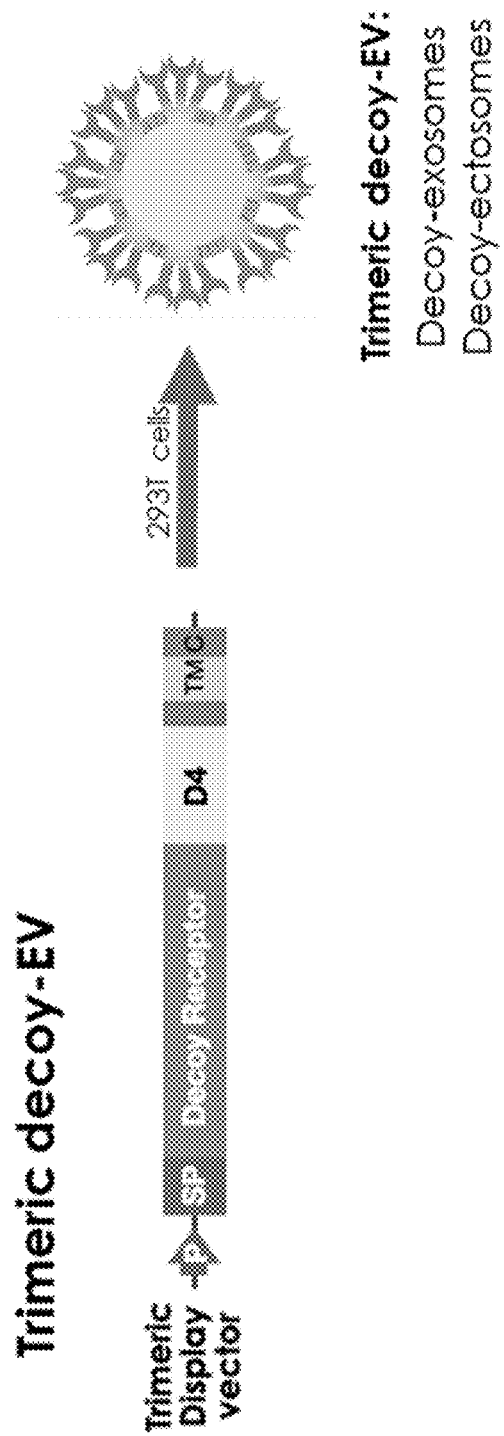
Figure 17A:
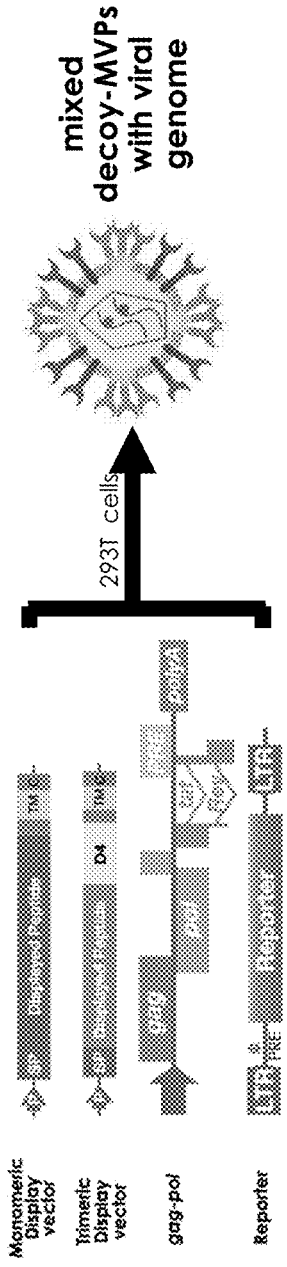
FIG. 17A-17C show in vitro production of mixed monomeric and trimeric decoy-MVPs.
Figure 17B:
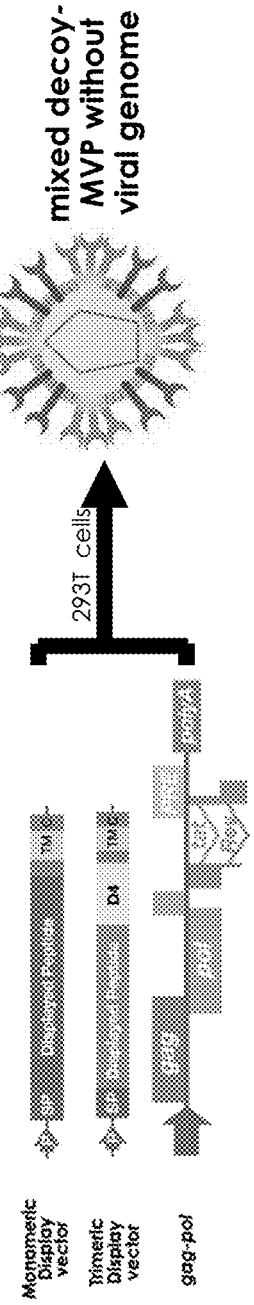
Figure 17C:
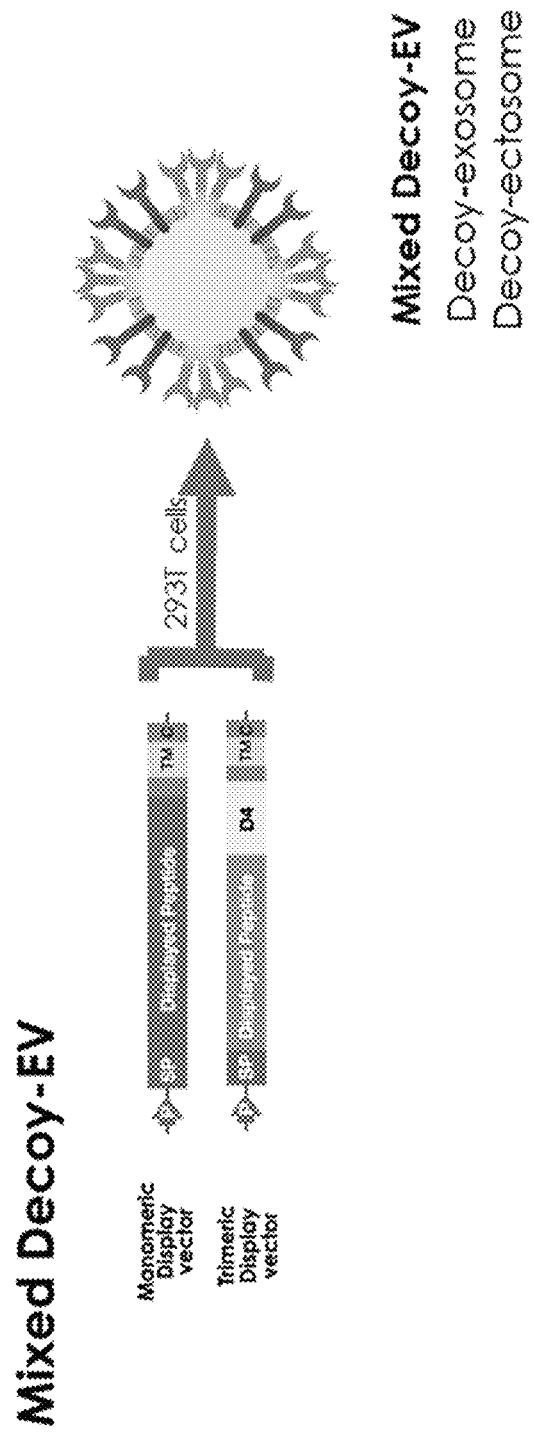
Figure 18A:
FIG. 18A-18E illustrate the effects of location and length of D4 trimerization domain on the neutralization potency of decoy-MVPs.
Figure 18B:
Figure 18C:
Figure 18D:
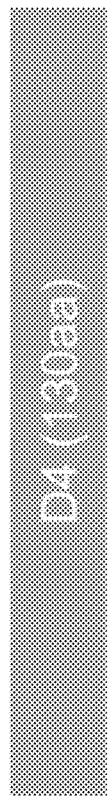
Figure 18D:
Figure 18D:
Figure 18E:
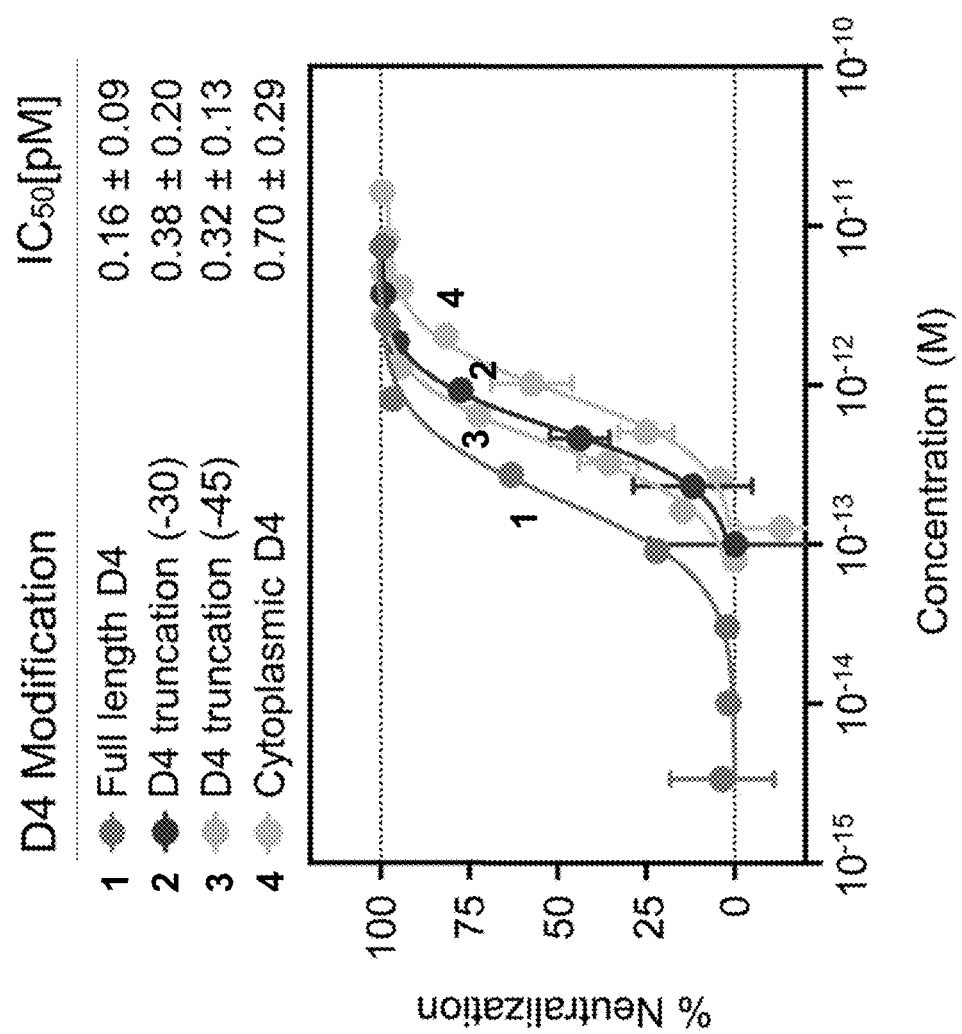
Figure 19A:
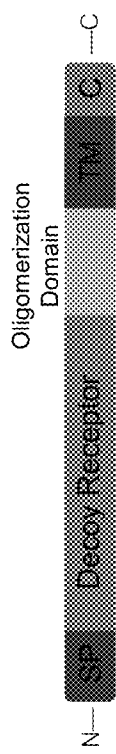
FIG. 19A-19C illustrate the design configurations for decoy receptor displaying vectors utilizing various oligomerization domains (Listed in Table 4).
Figure 19B:
Figure 19C:
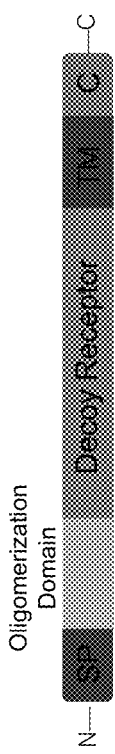

Multivalent decoy receptors are displayed as monomers on the surface of a VLP and an extracellular vesicle using a monomeric display vector. The monomeric VLP-based decoy-MVP is produced with viral RNA genomes in which the monomeric peptide display construct with a lentiviral packaging construct expresses essential packaging components including Gag-Pol and Rev proteins and a viral genome transfer encoding a GFP/luciferase reporter as shown in FIG. 15A. The monomeric VLP-based decoy-MVP without RNA genome is produced by co-transfecting displaying vector with only a lentiviral packaging construct but not the viral genome transfer vector as shown in FIG. 15B. The monomeric EV-based decoy-MVP which includes decoy-exosome and decoy-ectosome is produced by trans-fecting only monomeric peptide displaying vector in 293T cells as shown in FIG. 15C.

FIG. 15A shows monomeric decoy-MVP production by pseudo-typing ACE2 receptors on the lentiviral-based viral-like particles with viral genome. FIG. 15B shows Monomeric decoy-MVP production by pseudo-typing ACE2 receptors on the lentiviral-based viral-like particles without viral genome. FIG. 15C shows monomeric decoy-MVP production by pseudo-typing extracellular vesicles with ACE2 receptors.

Example 15: Generation of Trimeric Decoy-MVPs

Multivalent decoy receptors are displayed as trimers on the surface of a VLP and an extracellular vesicle using a trimeric display vector. The trimeric VLP-based decoy-MVP is produced with viral RNA genomes in which the trimeric peptide display construct with a lentiviral packaging construct expresses essential packaging components including Gag-Pol and Rev proteins and a viral genome transfer encoding a GFP/luciferase reported as shown in FIG. 16A. The trimeric VLP-based enveloped particle without RNA genome is produced by co-transfecting displaying vector together with only a lentiviral packaging construct but not the viral genome transfer vector as shown in FIG. 16B. The trimeric EV-based decoy-MVP which includes decoy-exosome and decoy-ectosome is produced by transfecting only the trimeric peptide displaying vector in 293T cells as shown in FIG. 16C.

FIG. 16A-16C show in vitro production of trimeric decoy-MVPs. FIG. 16A shows trimeric decoy-MVP production by pseudo-typing ACE2 receptors onto the lentiviral-based viral-like particles with viral genome. FIG. 16B shows trimeric decoy-MVP production by pseudo-typing ACE2 receptors onto the lentiviral-based viral-like particles without viral genome. FIG. 16C shows trimeric decoy-MVP production by pseudo-typing extracellular vesicles with ACE2 receptors.

Example 16: Generation of Mixed Monomeric and Trimeric Decoy-MVP

To further increase decoy display density, enveloped particles displaying mixed monomeric and trimeric decoy receptor are generated by co-transfecting monomeric and trimeric decoy display constructs. Such design is used to increase the density of the displayed peptide or to create combinatorial of distinct displayed decoys. Mixed monomeric and trimeric decoy-MVPs are built with VLPs and EVs by co-transfecting monomeric and trimeric display vectors.

To produce mixed decoy-MVPs with viral RNA genomes, the mixed monomeric and trimeric decoy receptor display constructs are co-transfected with a lentiviral packaging construct expressing essential packaging components, such as Gag-Pol and Rec proteins, and viral genome transfer vector encoding a GFP/luciferase reported as shown in FIG. 17A. The mixed decoy-MVPs without RNA genome are produced by co-transfecting the mixed monomeric and trimeric display vector together with only a lentiviral packaging construct but not the viral genome transfer vector as shown in FIG. 17B. The mixed EV-based decoy-MVPs which includes mixed decoy-exosome and decoy-ectosome is produced by transfecting the mixed monomeric and trimeric display peptide constructs into 293T cells as shown FIG. 17C.

FIG. 17A-17C show in vitro production of mixed monomeric and trimeric decoy-MVPs. FIG. 17A shows mixed monomeric and trimeric decoy-MVP production by pseudo-typing viral-entry receptors onto the lentiviral-based viral-like particles with viral genome. FIG. 17B shows mixed monomeric and trimeric decoy-MVP production by pseudo-typing viral-entry receptors onto the lentiviral-based viral-like particles without viral genome. FIG. 17C shows mixed monomeric and trimeric decoy-MVP production by pseudo-typing extracellular vesicles with viral-entry receptors.

Example 17: Oligomerization Configurations for the Decoy Proteins Displayed on Decoy-MVPs Decoy-MVPs were genetically programmed to display peptides of interest in various configurations by modifying the display vector as shown in FIGS. 18A-18C. The VSVG D4 trimerization domain were placed at various positions of the fusion peptide: (1) extracellular and juxtaposed to the transmembrane domain; (2) intracellular and juxtaposed to the transmembrane domain; (3) extracellular and after the signal peptide (FIGS. 18A-18C). Moreover, the length of D4 trimerization domain was varied from 85 to 100 to 130 amino acids (FIG. 18D). H2A/ACE2-D4VG MVPs with varied D4 location and length were shown to be highly potent inhibitors, neutralizing CoV-2 pseudovirus at $IC_{50}$s below 1 pM (FIG. 18E).

Furthermore, various oligomerization domains may be used for distinct surface display patterns that are suitable for the function of decoy receptors (FIGS. 19A-19C). In addition to the VSVG D4 trimerization domain, the Dengue E protein fusion domain or a foldon domain are used to create trimeric display patterns on the surface of VLPs and EVs. Leucine zipper domains and the influenza neuraminidase stem domain are used to create dimeric and tetrameric display patterns on the surface of VLPs and EVs, respectively. Exemplary oligomerization domains and valence are summarized in Table 4. With these display configurations, it is possible to program combinatorial decoy-MVPs with mixed monomeric, dimeric, trimeric, and tetrameric display patterns optimized to their function in target cell regulation or virus neutralization.

TABLE 4

Exemplary oligomerization domains and valence

| Oligomerization Domain | Valence |
|---|---|
| VSV-G protein D4 | Trimer |
| Dengue E protein fusion protein | Trimer |
| Foldon | Trimer |
| human C-propeptide of α1 (I) collagen | Trimer |
| Leucine Zipper | Dimer |
| Influenza Neuraminidase stem | Tetramer |

Example 18: Exemplary Sequences

TABLE 5

Sequences

| Name | SEQ ID NO | Accession Number | Amino Acid Sequence |
|---|---|---|---|
| ACE2 | 1 | NP_001358344 | MSSSSWLLLSLVAVTAAQSTIEEQAKTFLDKENHA EDLFYQSSLASWNYNTNITEENVQNMNNAGDKWS AFLKEQSTLAQMYPLQEIQNLTVKLQLQALQQNGSS VLSEDKSKRLNTILNTMSTIYSTGKVCNPDNPQECLL LEPGLNEIMANSLDYNERLWAWESWRSEVGKQLRP LYEEYVVLKNEMARANHYEDYGDYWRGDYEVNG VDGYDYSRGQLIEDVEHTFEEIKPLYEHLHAYVRAK LMNAYPSYISPIGCLPAHLLGDMWGRFWTNLYSLTV PFGQKPNIDVTDAMVDQAWDAQRIFKEAEKFFVSV GLPNMTQGFWENSMLTDPGNVQKAVCHPTAWDLG KGDFRILMCTKVTMDDFLTAHHEMGHIQYDMAYA AQPFLLRNGANEGFHEAVGEIMSLSAATPKHLKSIG LLSPDFQEDNETEINFLLKQALTIVGTLPFTYMLEKW RWMVFKGEIPKDQWMKKWWEMKREIVGVVEPVP HDETYCDPASLFHVSNDYSFIRYYTRTLYQFQFQEA LCQAAKHEGPLHKCDISNSTEAGQKLFNMLRLGKSE PWTLALENVVGAKNMNVRPLLNYFEPLFTWLKDQ NKNSFVGWSTDWSPYADQSIKVRISLKSALGDKAYE WNDNEMYLFRSSVAYAMRQYFLKVKNQMILFGEE DVRVANLKPRISENFFVTAPKNVSDIIPRTEVEKAIR MSRSRINDAFRLNDNSLEFLGIQPTLGPPNQPPVSIW LIVEGVVMGVIVVGIVILIFTGIRDRKKKNKARSGEN PYASIDISKGENNPGEQNTDDVQTSF |
| DPP4 | 2 | NP_001926 | MKTPWKVLLGLLGAAALVTIITVPVVLLNKGTDDA TADSRKTYTLTDYLKNTYRLKLYSLRWISDHEYLYK QENNILVFNAEYGNSSVFLENSTFDEFGHSINDYSISP DGQFILLEYNYVKQWRHSYTASYDIYDLNKRQLITE ERIPNNTQWVTWSPVGHKLAYVWNNDIYVKIEPNL PSYRITWTGKEDIIYNGITDWVYEEEVFSAYSALWW SPNGTFLAYAQFNDTEVPLIEYSFYSDESLQYPKTVR VPYPKAGAVNPTVKFFVVNTDSLSSVTNATSIQITAP ASMLIGDHYLCDVTWATQERISLQWLRRIQNYSVM DICDYDESSGRWNCLVARQHIEMSTTGWVGRFRPSE PHFTLDGNSFYKIISNEEGYRHICYFQIDKKDCTFITK GTWEVIGIEALTSDYLYYISNEYKGMPGGRNLYKIQ LSDYTKVTCLSCELNPERCQYYSVSFSKEAKYYQLR CSGPGLPLYTLHSSVNDKGLRVLEDNSALDKMLQN VQMPSKKLDFIILNETKFWYQMILPPHFDKSKKYPLL LDVYAGPCSQKADTVERLNWATYLASTENIIVASED GRGSGYQGDKIMHAINRRLGTFEVEDQIEAARQFSK MGFVDNKRIAIWGWSYGGYVTSMVLGSGSGVFKC GIAVAPVSRWEYYDSVYTERYMGLPTPEDNLDHYR NSTVMSRAENFKQVEYLLIHGTADDNVHFQQSAQIS KALVDVGVDFQAMWYTDEDHGIASSTAHQHIYTH MSHFIKQCFSLP |
|  | 3 | NP_955548 | KFTIVFPHNQKGNWKNVPSNYHYCPSSSDLNWHND LIGTALQVKMPKSHKAIQADGWMCHASKWVTTCD FRWYGPKYITHSIRSFTPSVEQCKESIEQTKQGTWLN PGFPPQSCGYATVTDAEAVIVQVTPHHVLVDEYTGE WVDSQFINGKCSNYICPTVHNSTTWHSDYKVKGLC DSNLISMDITFFSEDGELSSLGKEGTGFRSNYFAYET GGKACKMQYCKHWGVRLPSGVWFEMADKDLFAA ARFPECPEGSSISAPSQTSVDVSLIQDVERILDYSLCQ ETWSKIRAGLPISPVDLSYLAPKNPGTGPAFTIINGTL KYFETRYIRVDIAAPILSRMVGMISGTTTERELWDD WAPYEDVEIGPNGVLRTSSGYKFPLYMIGHGMLDS DLHLSSKAQVFEHPHIQDAASQLPDDESLFFGDTGLS KNPIELVEGWFSSWKSSIASFFFIIGLIIGLFLVLRVGI HLCIKLKHTKKRQIYTDIEMNRLGK |
|  | 4 | QJF75467 | MFVFLVLLPLVSSQCVNLTTRTQLPPAYTNSFTRGV YYPDKVFRSSVLHSTQDLFLPFFSNVTWFHAIHVSGT NGTKRFDNPVLPFNDGVYFASTEKSNIIRGWIFGTTL DSKTQSLLIVNNATNVVIKVCEFQFCNDPFLGVYYH KNNKSWMESEFRVYSSANNCTFEYVSQPFLMDLEG KQGNFKNLREFVFKNIDGYFKIYSKHTPINLVRDLPQ GFSALEPLVDLPIGINITRFQTLLALHRSYLTPGDSSS GWTAGAAAYYVGYLQPRTFLLKYNENGTITDAVDC ALDPLSETKCTLKSFTVEKGIYQTSNFRVQPTESIVRF PNITNLCPFGEVFNATRFASVYAWNRKRISNCVADY |

TABLE 5-continued

Sequences

| Name | SEQ ID NO | Accession Number | Amino Acid Sequence |
|---|---|---|---|
| | | | SVLYNSASFSTFKCYGVSPTKLNDLCFTNVYADSFVI |
| | | | RGDEVRQIAPGQTGKIADYNYKLPDDFTGCVIAWNS |
| | | | NNLDSKVGGNYNYLYRLFRKSNLKPFERDISTEIYQ |
| | | | AGSTPCNGVEGFNCYFPLQSYGFQPTNGVGYQPYR |
| | | | VVVLSFELLHAPATVCGPKKSTNLVKNKCVNFNFN |
| | | | GLTGTGVLTESNKKFLPFQQFGRDIADTTDAVRDPQ |
| | | | TLEILDITPCSFGGVSVITPGTNTSNQVAVLYQDVNC |
| | | | TEVPVAIHADQLTPTWRVYSTGSNVFQTRAGCLIGA |
| | | | EHVNNSYECDIPIGAGICASYQTQTNSPRRARSVASQ |
| | | | SIIAYTMSLGAENSVAYSNNSIAIPTNFTISVTTEILPV |
| | | | SMTKTSVDCTMYICGDSTECSNLLLQYGSFCTQLNR |
| | | | ALTGIAVEQDKNTQEVFAQVKQIYKTPPIKDFGGFN |
| | | | FSQILPDPSKPSKRSFIEDLLFNKVTLADAGFIKQYGD |
| | | | CLGDIAARDLICAQKFNGLTVLPPLLTDEMIAQYTSA |
| | | | LLAGTITSGWTFGAGAALQIPFAMQMAYRFNGIGVT |
| | | | QNVLYENQKLIANQFNSAIGKIQDSLSSTASALGKLQ |
| | | | DVVNQNAQALNTLVKQLSSNFGAISSVLNDILSRLD |
| | | | KVEAEVQIDRLITGRLQSLQTYVTQQLIRAAEIRASA |
| | | | NLAATKMSECVLGQSKRVDFCGKGYHLMSFPQSAP |
| | | | HGVVFLHVTYVPAQEKNFTTAPAICHDGKAHFPREG |
| | | | VFVSNGTHWFVTQRNFYEPQIITTDNTFVSGNCDVVI |
| | | | GIVNNTVYDPLQPELDSFKEELDKYFKNHTSPDVDL |
| | | | GDISGINASVVNIQKEIDRLNEVAKNLNESLIDLQEL |
| | | | GKYEQYIKWPWYIWLGFIAGLIAIVMVTIMLCCMTS |
| | | | CCSCLKGCCSCGSCCKFDEDDSEPVLKGVKLHYT |

Example 19: Discussion

A novel strategy to neutralize emerging coronaviruses was established using decoy-multivalent particles displaying high copy numbers of decoy viral-entry receptors. MVPs displaying ACE2 or DPP4 effectively neutralized SARS CoV-1/CoV-2, emerging CoV-2 variants and MERS coronaviruses. The decoy-MVPs were remarkably potent, often neutralizing their target viruses at sub-picomolar $IC_{50}$s and completely eliminating viral titers in live virus neutralization and antiviral assays. Furthermore, decoy-MVPs were over 10,000-fold more potent than their corresponding mono or low-valency recombinant entry receptor proteins. This enhancement correlated with the number of copies viral entry receptors displayed on the surface of these particles. With as low as ten receptor copies per MVP, the decoy-MVPs were already more potent than many clinical-stage neutralizing antibodies, and their potency were further increased by orders of magnitude by displaying more decoy receptors. The results demonstrate that the high valency of viral receptors on MVPs was the key to enabling maximum neutralizing efficacy of decoy-MVPs.

Multivalent interactions result in potent neutralization by decoy-MVPs: SARS CoV-2 virions, as well as many other enveloped and non-enveloped viruses, display hundreds of copies of large spike proteins and utilize multivalent interactions between spike and host-cell proteins for attachment and entry. The boost in functional affinity that viruses receive through multivalent interactions is exponential, and nearly all enveloped and non-enveloped viruses use this multivalent strategy for attachment and host-cell entry. This provides a tremendous advantage to viruses. Most notably, the multivalent strategy enabled viruses to turn relatively weak monovalent interactions with millimolar binding affinities into super-strong multivalent interactions with functional affinities in the nanomolar to picomolar range, in turn creating a high threshold for low or monovalent binders, such as neutralizing antibodies and recombinant protein inhibitors, to overcome.

In contrast to neutralizing antibodies, ACE2-MVPs and DPP4-MVPs were designed to function as decoy-target cells and readily formed multivalent interactions with the spike proteins of corresponding SARS Coronavirus virions. Both ACE2-MVPs and DPP4-MVPs had picomolar range IC50s and were considerably more potent than many neutralizing antibodies being tested in clinic. At over 200 copies of ACE2 molecules per particle, which was comparable to the number of Spike proteins per virion, ACE2-MVPs effectively competed with target cells for virus binding at a comparable functional affinity. Notably, ACE2-MVPs effectively blocked viral entry after viruses bound to target cells, indicating that decoy-MVPs latched onto viruses attached to cells through multivalent interaction and prevent them from fusing with target cells. Taken together, these findings illustrate that multivalent interaction underlies the potent neutralization by decoy-MVPs.

Decoy-MVPs create variant-proof multivalent traps for viruses: Viruses harness high mutation rates and multivalent binding to host cells to gain an advantage in targeted cell entry and immune evasion. Spike mutagenesis and novel glycosylation patterns can effectively disrupt the neutralizing function of antibodies and other low-valency viral-blocking agents, enabling viruses to win the cat-and-mouse game with our immune system. It is likely that mutations that are resistant to current combinations of clinically tested neutralization antibodies will emerge and render these therapies less effective. Not surprisingly, it remains a challenge to develop effective low-valency neutralizing compounds against viruses or to generate universal vaccines by using highly potent antibodies.

In contrast, a virus would not be able to escape neutralization control by a corresponding decoy-MVP without losing or significantly altering its original tropism. Mutations abolishing spike and ACE2 binding abolish virion interaction with ACE2-MVP and target cells, whereas mutations enhancing spike and ACE2 binding augment virion interaction with ACE2-MVP and target cells. The ACE2-

MVPs of the disclosure neutralized D614G CoV-2 viruses at comparable or higher efficiency than the original SARS CoV-1 and CoV-2 viruses. Thus, ACE2-MVPs, which were broadly neutralizing against all SARS coronaviruses utilizing ACE2 as a host cell receptor, created multivalent traps that were difficult for viruses to escape. In the event that SARS CoV-2 evolved to adopt a new host cell receptor or a new zoonotic coronavirus jumped to humans, decoy-MVPs could be readily developed once their host cell receptors are identified. As a proof of the adaptability of the decoy-MVP strategy, DPP4-MVPs for MERS were created, which demonstrated that these decoy-MVPs were highly potent in neutralizing MERS viruses. In addition to high potency, the decoy-MVP strategy effectively countered existing strategies of viral immune evasion, offering another critical advantage over neutralizing antibodies.

Decoy-MVPs as building blocks for modular antivirals: The demonstration of decoy-MVPs as potent antivirals illustrated a modular approach to block viruses from entering cells by building MVPs displaying universal features required for viral attachment and entry. The approach enabled the development of antivirals using a relative constant for viral pathogenesis—host cell receptors. The advantage of the approach was evident in comparison to developing neutralizing antibodies for a constantly evolving spike or surface glycoprotein. Decoy-MVPs can be built to precisely mimic target cells so that the virus cannot distinguish the two in terms of molecular identity and multivalent functional affinity.

The decoy-MVPs of the disclosure displayed a single type of viral entry receptor, such as wild-type ACE2 for SARS-CoV-1/2 and wild-type DPP4 for MERS coronavirus. Conceivably, such decoy-MVPs could be further modified to display mutated viral entry receptors with improved affinity to viral envelope proteins, reduced size for ease of production, and inactivated physiological function to avoid undesirable impacts on normal physiology. For example, ACE2 has enzymatic activities required for angiotensin processing. Thus, delivering large amounts of functional ACE2-MVPs may cause a dramatic decrease in Angiotensin II levels and increase of angiotensin (1-5/7). Therefore, enzymatically inactive ACE2 or DPP4 may be displayed on MVPs to eliminate other functions of the decoy-MVPs that are unrelated to antiviral function.

Many viruses utilize both host cell attachment receptors and entry receptors for infection. For example, while ACE2 is essential for virus infection, SARS CoV-2 entry of target cells may also be facilitated by TMPRSS2, DPP4, and sialic acid. Decoy-MVPs were generated by displaying viral decoy receptors, such as ACE2 and DPP4, on the lentiviral particles. With this design, decoy-MVPs could be modified by co-transfecting to ACE2-displaying vector together with displaying vectors for host-cell entry receptors, attachment receptors, and other molecules important for viral infection. Ratios can be tuned to maximize their neutralizing potential and accurately recapitulate a typical target cell membrane. Decoy receptors could also be displayed on other types of viruses with or without lipid envelopes or on the surface of synthetic nanoparticles. Beyond decoy-MVPs, other types of multivalent particles can be generated by displaying spike-specific antibodies or other engineered spike-binding proteins alone or together with decoy receptors for enhanced neutralization function. Finally, decoy-MVPs can be armed with additional regulatory molecules on their surfaces or inside nanoparticles to deliver additional cargo for immune modulation, targeted degradation, and vaccination.

The decoy-MVP strategy enables preemptive development of antivirals: Viral zoonoses, the transmission of viral diseases between animals to humans, has and continues to be a significant public health risk with epidemic, endemic, and pandemic potential. However, because of high mutation rates during virus replication, humans have been playing catchup to develop effective antiviral therapeutics in an effort to control outbreaks of influenza, coronaviruses, and other zoonotic viruses. Since nearly all enveloped and non-enveloped viruses use their multivalent surface envelope proteins for attachment and host-cell entry, our results suggest that decoy-MVPs can be used as modular antiviral therapeutics for all viruses that utilize host cell receptors for cell attachment and entry. The decoy-MVP strategy of the disclosure suggests a novel approach to preemptively develop modular decoy-MVPs for any human and animal virus with zoonotic potential. Instead of chasing elusive super-antibodies for rapidly evolving viruses, host cell entry receptors can be identified for pathogenic human viruses and animal viruses with zoonotic potential, and decoy-MVPs therapeutics can be pre-emptively developed. This approach will provide an important arsenal for fighting against many pathogenic human viruses, such as influenza, coronaviruses, hepatitis viruses, dengue virus, and HIV.

Example 20: Methods and Materials

Design and production of spike-pseudotyped viral-like particles: Codon-optimized synthetic DNAs encoding the SARS CoV-1, CoV-2, and MERS Coronavirus spike proteins were cloned into a mammalian expression vector placing under the control of a CMV promoter. For improved CoV-2 spike expression and pseudotyping, a construct expressing a chimeric protein containing the extracellular spike domain fused to VSV-G transmembrane and cytosolic tails was also generated. The expression of spike proteins after transfecting into 293T cells was validated by Western-blots using specific antibodies against respective spike protein and the VSV-G tag.

To produce spike-pseudotyped viral-like particles, spike expression construct, psPAX2 lentiviral packaging vector, and a lentiviral transfer vector with luciferase reporter were co-transfected into 293T cells using a polyethyenimine (PEI) transfection protocol. psPAX2 is a generation 2 lentiviral vector packaging vector expressing gag, pol, rev proteins. Briefly, eight million 293T cells were seeded onto a 10 cm plate 16-24 hour before transfection and cultured overnight. Cells should reach ~90% of confluency at the time of transfection. A transfection mix was prepared by adding 30 µg of diluted PEI solution to a DNA cocktail containing 1.25 µg of spike expression construct, 5 µg of psPAX2 lentiviral packaging vector, and 7.5 µg of lentiviral luciferase reporter vector. The transfection mix was incubated at room temperature for 15 minutes and then added to the cells. At 5-6 hours post transfection, cell culture medium was changed to virus production medium containing 0.1% sodium butyrate. Coronavirus pseudovirions were collected twice at 24- and 48-hour post medium change, concentrated by PEG precipitation, and further purified through a gel-filtration column.

Design and production of decoy-multivalent particles displaying ACE2 receptors (ACE2-MVPs): Synthetic DNAs encoding the ACE2 ectodomain were fused to various viral displaying anchor molecules and were cloned into a mammalian expression vector under the control of a CMV promoter. Viral envelope proteins were chosen as displaying anchor molecules because they are integral to viral biogenesis and are highly efficient at targeting viral membrane. ACE2 displaying constructs were generated expressing the ACE2 ectodomain fused to full-length VSV-G, or the truncated VSV-G with only transmembrane and cytosolic domains, or the truncated CoV-2 spike with S1 domain deleted. Synthetic DNAs encoding DPP4 ectodomain were fused to the HCΔ18 transmembrane domain from measles virus.

To produce decoy multivalent-particles, ACE2 or DPP4 displaying construct, psPAX2 lentiviral packaging vector, and a lentiviral transfer vector with GFP reporter were co-transfected into 293T cells using a polyethyenimine (PEI) transfection protocol. Briefly, eight million 293T cells were seeded onto a 10 cm plate 16-24 hour before transfection and cultured overnight. Cells were expected to reach ~90% of confluency by the time of transfection. A transfection mix was prepared by adding 30 ug of diluted PEI solution to a DNA cocktail containing 1.25 μg of ACE2 or DPP4 expression construct, 5 μg of psPAX2 lentiviral packaging vector, and 7.5 μg of GFP reporter vector. The transfection mix was incubated at room temperature for 15 minutes and then added to the cells. At 5-6 hours post transfection, cell culture medium was changed to virus production medium containing 0.1% sodium butyrate. ACE2-MVPs were collected twice at 24- and 48-hour post medium change, concentrated by PEG precipitation, and further purified through a gel-filtration column.

ACE2-MVPs without viral genome could also be packaged with no transfer vector without compromising ACE2-MVP yields and function. Several viral envelope proteins were tested for anchoring ACE2 protein to the membrane of the pseudo-lentiviral particles, including VSV-G (glycoprotein of Vesicular Stomatitis virus), HCΔ18 (a mutant version of hemagglutinin envelope protein from measles virus), and S2 (the fusion domain of SARS CoV-2 spike protein). Fusions of ACE2 to the full-length VSVG and truncated VSV-G with only transmembrane region and cytosolic tail were also tested.

Western blot analysis of decoy-MVPs: Expression of fusion proteins on decoy-MVPs are confirmed via western blot analysis of purified particles. Samples of purified MVPs are lysed at 4° C. for 10 minutes with cell lysis buffer (Cell Signaling) before being mixed with NuPage LDS sample buffer and boiled at 95° C. for 5 minutes. Differences in oligomerization are determined by running samples in reducing and non-reducing conditions. Under reducing conditions, 5% 2-Mercaptoethanol are added to samples to dissociate oligomerized MVP-ICs. Protein samples are then separated on NuPAGE 4-12% Bis-Tris gels and transferred onto a polyvinylidene fluoride (PVDF) membrane. PVDF membranes are blocked with TRIS-buffered saline with Tween-20 (TBST) and 5% skim milk for 1 hour, prior to overnight incubation with primary antibody diluted in 5% milk. For display fusion constructs expressing VSVG-tag, an anti-VSV-G epitope tag rabbit polyclonal antibody are used at a 1:2000 dilution. The following day, the PVDF membrane are washed 3 times with 1×TBST and stained with a goat-anti-rabbit secondary antibody (IRDye 680) at a 1:5000 dilution for 60 minutes in 5% milk. Post-secondary antibody staining, the PVDF membrane are again washed 3 times with TBST before imaging on a Licor Odyssey scanner.

Alternatively, western blot analyses are performed using an automated Simple Western size-based protein assay (Protein Simple) following the manufacturer's protocols. Unless otherwise mentioned, all reagents used here are from Protein Simple. Concentrated samples are lysed as described above, before being diluted 1:10 in 0.1× sample buffer for loading on capillaries. Displayed fusion protein expression levels are identified using the same primary rabbit polyclonal antibody at a 1:400 dilution and an HRP conjugated anti-rabbit secondary antibody (Protein Simple). Chemiluminescence signal analysis and absolute quantitation are performed using Compass software (Protein Simple).

Quantitative western blot analyses of decoy-MVPs: Quantitative western blot analyses were carried out to determine the copies of ACE2 and DPP4 on the lentiviral particles. P24 ELISA assays were used to determine the lentiviral particle concentration of the ACE2-MVPs. Samples containing decoy-MVP samples (2-3×$10^8$ particles, ~20 μg protein) were mixed with loading buffer and boiled at 100° C. for 5 minutes. The proteins and their corresponding serial-diluted recombinant protein standards were separated on 12% sodium dodecyl sulfate polyacrylamide (SDS-PAGE) and transferred onto a polyvinylidene fluoride (PVDF) membrane. The membrane was blocked with phosphate buffered saline with Tween-20 (PBST) and 5% skim milk at room temperature for 2 hours and subsequently incubated overnight at room temperature with the primary goat-anti-human ACE2 antibodies. The membrane was incubated at room temperature for one hour with the secondary antibodies (IRDye 680 anti-goat secondary) and quantified on a Licor Odyssey scanner. The copies of ACE2 or DPP4 proteins on respective decoy-MVPs were calculated by using the standard curves generated by corresponding ACE2 and -DPP4 recombinant proteins.

Viral-like particle quantification by p24 ELISA: P24 concentrations in pseudovirus samples of pseudotyped coronaviruses, influenza viruses and decoy-multivalent particles are determined using an HIV p24 SimpleStep ELISA kit. Concentrations of lentiviral pseudovirus particles are extrapolated from the assumption that each lentiviral particle contains approximately 2000 molecules of p24, or 1.25×$10^4$ pseudovirus particles per picogram of p24 protein.

Quantify decoy-MVPs by Tunable Resistive Pulse Sensing: The sizes and concentrations of VLP_based or extracellular vesicle-based decoy-MVPs are determined by tunable resistive pulse sensing (TRPS, qNano, IZON). Purified pseudovirus collections are diluted in 0.2 μm filtered PBS with 0.03% Tween-20prior to qNano analysis. Concentration and size distributions of MVP-ICs are then determined using an NP200 nanopore at a 45.5 mm stretch, and applied voltages between 0.5 and 0.7V were used to achieve a stable current of 130 nA through the nanopore. Measurements for each pseudovirus sample are taken at pressures of 3, 5 and 8 mbar, and considered valid if at least 500 events were recorded, particle rate was linear and root mean squared signal noise was maintained below 10 pA. MVPs concentrations are then determined by comparison to a standardized multi-pressure calibration using CPC200 (mode diameter: 200 nm) (IZON) carboxylated polystyrene beads diluted 1:200 in 0.2 μM filtered PBS from their original concentration of 7.3×1011 particles per/mL. Measurements are analyzed using IZON Control Suite 3.4 software to determine original sample concentrations.

Characterization of Proteins Displayed on Enveloped Particles: The concentration of VLP- or EV-based decoy-MVPs are measured by P24 ELISA or tunable resistive pulse sensing (TRPS, qNano), respectively. Then, copies of displayed peptides on enveloped particles are determined by quantitative Western-blot analyses. Finally, the oligomerization patterns of displayed peptides on the enveloped particles were discerned by non-reducing PAGE analyses. Enveloped particles are expected to display at least 10 copies of protein molecules on surface of VLPs and EVs with monomeric or trimeric configurations.

Target cells for coronavirus pseudovirus infection: A large panel of cell lines was screened to identify target cell lines that were effectively infected by spike pseudovirions. Candidate target cells were infected with saturated doses of coronavirus spike pseudovirions carrying a luciferase reporter, and luciferase activity of the infected cells was measured at 48 hours post-infection. Target cells that yielded at least 1,000-fold luciferase signals above the background infection were considered infectable. The cell lines tested included native cell lines, such as VERO, VERO E6, large panel of human lung cancer cell lines, and ACE2 overexpression cell lines. H1650 cells were effective target cells for the MERS spike pseudovirions (>10,000-fold increase in luciferase signals), 293T/ACE2 and H1573/ACE2 cells were effective target cells for the CoV-2 spike pseudovirions (10,000 to 100,000-fold increase in luciferase signals), and 293T/ACE2 and VERO E6 were effective target cells for the CoV-1 spike pseudovirions (1,000 to 10,000-fold increase in luciferase signals). $TCID_{50}$ (Fifty-percent tissue culture infective dose) were then determined for CoV-1, CoV-2, and MERS spike pseudovirions by titrating the dose-dependent infection in respective target cell lines. The $TCID_{50}$ doses were used in the pseudovirus neutralization assay to determine the inhibitory activities of decoy-MVPs.

$IC_{50}$ Pseudovirus neutralization assay: Respective target cells were seeded in 96-well, flat-bottom, clear, tissue-culture treated plates at 25,000 cells/well with 6 μg/mL polybrene in the appropriate base medium supplemented with 10% fetal bovine serum and 1% Penicillin Streptomycin. RPMI media with glucose, HEPES Buffer, L-Glutamine, sodium bicarbonate and sodium pyruvate served as base medium for H1573/ACE2 cells and H1650 cells, while 293T Growth Media was used as base medium for 293T/17 cells. Pseudovirus was then added to wells at $TCID_{50}$ concentrations, along with titrated decoy anti-Virus MVP in 9×2-fold serial dilutions, yielding a 10-point dilution curve. In delayed pseudovirus neutralization assays, pseudovirus was added to wells in $TCID_{50}$ concentrations and incubated with cells for 60 minutes prior to the addition of titrated anti-Virus MVP. Plates containing cells, pseudovirus and decoy-MVP were then centrifuged at 800×g, 25° C. for 60 minutes to maximize infection efficiency. 48 hours post-infection, cells were lysed using Firefly Luciferase Lysis Buffer and lysis was transferred to 96-well, white assay plates before luciferase activity was analyzed via GLOMAX multi-detection system. Titrated infection data was then plotted and fitted to a 4-parameter, logistic curve in order to calculate the half maximal inhibitory concentration ($IC_{50}$) of various decoy anti-Virus MVPs neutralizing their respective pseudoviruses.

Plaque reduction neutralization test with SARS CoV-2 virus: Vero E6 cells (ATCC: CRL-1586) were seeded at 175,000 cells/well using DMEM media supplemented with 10% fetal bovine serum (FBS) and Gentamicin in 24-well, tissue-culture treated plates. Cells were then incubated overnight at 37° C. in 5% $CO_2$ until reaching 80-100% confluence the next day. The following day, anti-Virus MVP samples in serum were heat inactivated at 56° C. for 30 minutes before preparing serial dilutions. All dilutions were made using DMEM supplemented with 2% FBS and Gentamicin (referred to as "diluent"). Anti-Virus MVP serial dilutions, to a total volume of 300 μL, were made using diluent, and 300 μL empty diluent served as a virus positive control. Next, 300 μL diluent containing SARS CoV-2 (30 PFU/well) was added to anti-Virus MVP serial dilutions and to the virus-only positive control, to a final volume of 600 μL. Mixtures of anti-Virus MVP and SARS CoV-2 were incubated at 37° C. in 5.0% $CO_2$ for 60 minutes, before serial dilutions and virus positive control were added to cells. Cells were incubated with mixtures for 1 hour to allow for infection, and virus titers for each serial dilution were then determined by plaque assay. Percent neutralization data was plotted and a 4-parameter logistic curve was fitted to data to determine the 50% plaque reduction neutralization titer ($PRNT_{50}$) of various anti-Virus MVPs neutralizing live SARS CoV-2 virus (GraphPad Prism 9.0.0).

In vivo live virus neutralization efficacy of ACE2-MVP in hamsters: Eight golden hamsters, male and female, 6-8 weeks old were used in each cohort. Animals were weighed prior to the start of the study. Animals were challenged with 2.3×10^4 PFU of USA-WA1/2020 through IN administration of 50 μL of viral inoculum into each nostril. At various time points after infection, hamsters are treated with decoy-MVPs through intranasal delivery. The animals were monitored twice daily for signs of COVID-19 disease (ruffled fur, hunched posture, labored breathing) during the study period. Body weights were measured once daily during the study period. Lung tissues were collected and sampled for viral load assays by PRNT. Tissues were stored at 80° C. for histology and viral load analysis by qPCR or PRNT analyses.

In vivo live virus neutralization efficacy of ACE-MVP in ACE2 mice: Six ACE2 transgenic mice, male and female, 6-8 weeks old were used in each cohort. Animals were weighed prior to the start of the study. Animals were challenged with $2.3 \times 10^4$ PFU of USA-WA1/2020 through intranasal administration of 50 μL of viral inoculum into each nostril. At various time points after infection, hamsters are treated with decoy-MVPs through intranasal delivery. The animals were monitored twice daily for signs of COVID-19 disease (ruffled fur, hunched posture, labored breathing) and survival during the study period. Body weights were measured once daily during the study period. Lung tissues were collected and sampled for viral load assays by PRNT. Tissues were stored at 80° C. for histology and viral load analysis by qPCR or PRNT analyses.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EMBODIMENTS

The following non-limiting embodiments provide illustrative examples of the invention, but do not limit the scope of the invention.

Embodiment 1. A multivalent particle comprising a fusion protein that comprises a mammalian polypeptide that binds to a viral protein and a transmembrane polypeptide wherein the fusion protein is expressed at least about 10 copies on a surface of the multivalent particle.

Embodiment 2. The multivalent particle of embodiment 1, wherein the viral protein is from SARS-CoV-1, SARS-CoV-2, MERS-CoV, Respiratory syncytial virus, HIV, or combinations thereof.

Embodiment 3. The multivalent particle of embodiment 1 or 2, wherein the mammalian polypeptide comprises a receptor that has binding specificity for the viral protein.

Embodiment 4. The multivalent particle of embodiment 3, wherein the receptor comprises a viral entry receptor or a viral attachment receptor.

Embodiment 5. The multivalent particle of embodiment 3, wherein the receptor is both a viral entry receptor and a viral attachment receptor.

Embodiment 6. The multivalent particle of embodiment 3, wherein the mammalian polypeptide comprises an extracellular domain of the receptor.

Embodiment 7. The multivalent particle of embodiment 1 or 2, wherein the mammalian polypeptide comprises a ligand or a secreted protein.

Embodiment 8. The multivalent particle of embodiment 1 or 2, wherein the mammalian polypeptide comprises ACE2, TRMPSS2, DPP4, CD4, CCR5, CXCR4, CD209, or CLEC4M.

Embodiment 9. The multivalent particle of embodiment 1 or 2, wherein the mammalian polypeptide comprises an amino acid sequence of at least 90% sequence identity to an amino acid sequence according to SEQ ID NO: 1.

Embodiment 10. The multivalent particle of embodiment 1 or 2, wherein the mammalian polypeptide comprises an amino acid sequence of at least 90% sequence identity to an amino acid sequence according to SEQ ID NO: 2.

Embodiment 11. The multivalent particle of any one of embodiments 1-10, wherein the transmembrane polypeptide anchors the fusion protein to a bilayer of the multivalent particle.

Embodiment 12. The multivalent particle of any one of embodiments 1-11, wherein the transmembrane polypeptide comprises a spike glycoprotein transmembrane region, a mammalian membrane protein, an envelope protein, a nucleocapsid protein, or a cellular transmembrane protein.

Embodiment 13. The multivalent particle of any one of embodiments 1-11, wherein the transmembrane polypeptide comprises a VSVG transmembrane region, spike protein 51 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120.

Embodiment 14. The multivalent particle of embodiment 13, wherein the VSVG transmembrane region comprises full length VSVG transmembrane region or a truncated VSVG transmembrane region.

Embodiment 15. The multivalent particle of embodiment 13, wherein the transmembrane polypeptide comprises the VSVG transmembrane region and a VSVG cytoplasmic tail.

Embodiment 16. The multivalent particle of any one of embodiments 1-11, wherein the transmembrane polypeptide comprises an amino acid sequence at least about 90% identical to that set forth in SEQ ID NO: 3.

Embodiment 17. The multivalent particle of any one of embodiments 1-11, wherein the transmembrane polypeptide comprises an amino acid sequence at least about 90% identical to that set forth in SEQ ID NO: 4.

Embodiment 18. The multivalent particle of any one of embodiments 1-17, wherein the fusion protein is expressed at least about 50 copies on a surface of the multivalent particle.

Embodiment 19. The multivalent particle of any one of embodiments 1-17, wherein the fusion protein is expressed at least about 75 copies on a surface of the multivalent particle.

Embodiment 20. The multivalent particle of any one of embodiments 1-17, wherein the fusion protein is expressed at least about 100 copies on a surface of the multivalent particle.

Embodiment 21. The multivalent particle of any one of embodiments 1-17, wherein the fusion protein is expressed at least about 150 copies on a surface of the multivalent particle.

Embodiment 22. The multivalent particle of any one of embodiments 1-17, wherein the fusion protein is expressed at least about 200 copies on a surface of the multivalent particle.

Embodiment 23. The multivalent particle of embodiment 1, wherein the mammalian polypeptide comprises ACE2 and the transmembrane polypeptide comprises a VSVG transmembrane region.

Embodiment 24. The multivalent particle of embodiment 1, wherein the mammalian polypeptide comprises ACE2 and the transmembrane polypeptide comprises a spike protein S2 transmembrane region.

Embodiment 25. The multivalent particle of embodiment 1, wherein the mammalian polypeptide comprises ACE2 and the transmembrane polypeptide comprises a surface glycoprotein transmembrane region of an enveloped virus.

Embodiment 26. The multivalent particle of embodiment 1, wherein the mammalian polypeptide comprises DPP4 and the transmembrane polypeptide comprises hemagglutinin envelope protein from measles virus.

Embodiment 27. The multivalent particle of embodiment 26, wherein the hemagglutinin envelope protein from measles virus is a variant of the hemagglutinin envelope protein from measles virus.

Embodiment 28. The multivalent particle of any one of embodiments 1-27, wherein the multivalent particle further comprises a second fusion protein that comprises a second mammalian polypeptide that binds to the viral protein and a second transmembrane polypeptide wherein the second fusion protein is expressed at least about 10 copies on the surface of the multivalent particle.

Embodiment 29. The multivalent particle of embodiment 28, wherein the second mammalian polypeptide comprises a receptor that has binding specificity for the viral protein.

Embodiment 30. The multivalent particle of embodiment 29, wherein the receptor comprises a viral entry receptor or a viral attachment receptor.

Embodiment 31. The multivalent particle of embodiment 29, wherein the receptor is both a viral entry receptor and a viral attachment receptor.

Embodiment 32. The multivalent particle of embodiment 29, wherein the second mammalian polypeptide comprises an extracellular domain of the receptor.

Embodiment 33. The multivalent particle of embodiment 28, wherein the second mammalian polypeptide comprises a ligand or a secreted protein.

Embodiment 34. The multivalent particle of embodiment 28, wherein the second mammalian polypeptide comprises ACE2, TRMPSS2, DPP4, CD4, CCR5, CXCR4, CD209, or CLEC4M.

Embodiment 35. The multivalent particle of embodiment 28, wherein the second mammalian polypeptide comprises an amino acid sequence of at least 90% sequence identity to an amino acid sequence according to SEQ ID NO: 1.

Embodiment 36. The multivalent particle of embodiment 28, wherein the second mammalian polypeptide comprises an amino acid sequence of at least 90% sequence identity to an amino acid sequence according to SEQ ID NO: 2.

Embodiment 37. The multivalent particle of any one of embodiments 28-36, wherein the second transmembrane polypeptide comprises a transmembrane anchoring protein.

Embodiment 38. The multivalent particle of any one of embodiments 28-36, wherein the second transmembrane polypeptide comprises a spike glycoprotein transmembrane region, a mammalian membrane protein, an envelope protein, a nucleocapsid protein, or a cellular transmembrane protein.

Embodiment 39. The multivalent particle of any one of embodiments 28-36, wherein the second transmembrane polypeptide comprises VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120.

Embodiment 40. The multivalent particle of embodiment 39, wherein the VSVG transmembrane region comprises full length VSVG transmembrane region or a truncated VSVG transmembrane region.

Embodiment 41. The multivalent particle of embodiment 39, wherein the transmembrane polypeptide comprises a VSVG transmembrane region and a VSVG cytoplasmic tail.

Embodiment 42. The multivalent particle of any one of embodiments 28-36, wherein the second transmembrane polypeptide comprises an amino acid sequence at least about 90% identical to that set forth in SEQ ID NO: 3.

Embodiment 43. The multivalent particle of any one of embodiments 28-36, wherein the second transmembrane polypeptide comprises an amino acid sequence at least about 90% identical to that set forth in SEQ ID NO: 4.

Embodiment 44. The multivalent particle of any one of embodiments 28-43, wherein the second fusion protein is expressed at least about 50 copies on a surface of the multivalent particle.

Embodiment 45. The multivalent particle of any one of embodiments 28-43, wherein the second fusion protein is expressed at least about 75 copies on a surface of the multivalent particle.

Embodiment 46. The multivalent particle of any one of embodiments 28-43, wherein the second fusion protein is expressed at least about 100 copies on a surface of the multivalent particle.

Embodiment 47. The multivalent particle of any one of embodiments 28-43, wherein the second fusion protein is expressed at least about 150 copies on a surface of the multivalent particle.

Embodiment 48. The multivalent particle of any one of embodiments 28-43, wherein the second fusion protein is expressed at least about 200 copies on a surface of the multivalent particle.

Embodiment 49. The multivalent particle of embodiment 28, wherein the second mammalian polypeptide comprises ACE2 and the second transmembrane polypeptide comprises VSVG transmembrane region.

Embodiment 50. The multivalent particle of embodiment 28, wherein the second mammalian polypeptide comprises ACE2 and the second transmembrane polypeptide comprises spike protein S2 transmembrane region.

Embodiment 51. The multivalent particle of embodiment 28, wherein the second mammalian polypeptide comprises ACE2 and the second transmembrane polypeptide comprises a surface glycoprotein of an enveloped virus.

Embodiment 52. The multivalent particle of embodiment 28, wherein the second mammalian polypeptide comprises DPP4 and the second transmembrane polypeptide comprises hemagglutinin envelope protein from measles virus.

Embodiment 53. The multivalent particle of embodiment 52, wherein the hemagglutinin envelope protein from measles virus is a variant of the hemagglutinin envelope protein from measles virus.

Embodiment 54. The multivalent particle of embodiment 28, wherein the mammalian polypeptide comprises a viral entry receptor and the second mammalian polypeptide comprises a viral attachment receptor.

Embodiment 55. The multivalent particle of embodiment 28, wherein the mammalian polypeptide comprises ACE2, the transmembrane polypeptide comprises VSVG transmembrane region, spike protein S1 transmembrane region, spike protein S2 transmembrane region, or a surface glycoprotein of an enveloped virus, the second mammalian polypeptide comprises a heparan sulfate proteoglycan, and the second transmembrane polypeptide comprises VSVG transmembrane region, spike protein S1 transmembrane region, spike protein S2 transmembrane region, or a surface glycoprotein of an enveloped virus.

Embodiment 56. The multivalent particle of embodiment 28, wherein the mammalian polypeptide comprises CD4 and the second mammalian peptide comprises, CCR5, CXCR4, or both.

Embodiment 57. The multivalent particle of any one of embodiments 1-56, wherein the multivalent particle comprises an IC50 of less than 5 picomolar (pM) in a neutralization assay.

Embodiment 58. The multivalent particle of any one of embodiments 1-56, wherein the multivalent particle comprises an IC50 of less than 2.5 picomolar (pM) in a neutralization assay.

Embodiment 59. The multivalent particle of any one of embodiments 1-56, wherein the multivalent particle comprises an IC50 of less than 1 picomolar (pM) in a neutralization assay.

Embodiment 60. The multivalent particle of any one of embodiments 1-59, wherein the multivalent particle does not comprise viral genetic material.

Embodiment 61. The multivalent particle of any one of embodiments 1-60, wherein the multivalent particle is synthetic.

Embodiment 62. The multivalent particle of any one of embodiments 1-60, wherein the multivalent particle is recombinant.

Embodiment 63. The multivalent particle of any one of embodiments 1-60, wherein the multivalent particle is a viral-like a particle.

Embodiment 64. The multivalent particle of any one of embodiments 1-60, wherein the multivalent particle is an extracellular vesicle.

Embodiment 65. The multivalent particle of any one of embodiments 1-60, wherein the multivalent particle is an exosome.

Embodiment 66. The multivalent particle of any one of embodiments 1-60, wherein the multivalent particle is an ectosome.

Embodiment 67. The multivalent particle of any one of embodiments 1-65, wherein the fusion protein further comprises an oligomerization domain.

Embodiment 68. The multivalent particle of embodiment 66, wherein the oligomerization domain is a dimerization domain.

Embodiment 69. The multivalent particle of embodiment 68, wherein the dimerization domain comprises a leucine zipper dimerization domain.

Embodiment 70. The multivalent particle of embodiment 66, wherein the oligomerization domain is a trimerization domain.

Embodiment 71. The multivalent particle of embodiment 70, wherein the trimerization domain comprises a post-fusion oligomerization domain of viral surface protein.

Embodiment 72. The multivalent particle of embodiment 70, wherein the trimerization domain comprises a D4 post-fusion trimerization domain of VSV-G protein.

Embodiment 73. The multivalent particle of embodiment 70, wherein the trimerization domain comprises a Dengue E protein post-fusion trimerization domain.

Embodiment 74. The multivalent particle of embodiment 70, wherein the trimerization domain comprises a foldon trimerization domain.

Embodiment 75. The multivalent particle of embodiment 69, wherein the trimerization domain comprises human C-propeptide of α1(I) collagen.

Embodiment 76. The multivalent particle of embodiment 66, wherein the oligomerization domain is a tetramerization domain.

Embodiment 77. The multivalent particle of embodiment 75, wherein the tetramerization domain comprises an influenza neuraminidase stem domain.

Embodiment 78. The multivalent particle of embodiment 66, wherein the oligomerization domain comprises an amino acid sequence that has at least 95% sequence identity to an amino acid sequence according to SEQ ID NOs: 5-18, or 28.

Embodiment 79. The multivalent particle of any one of embodiments 66-78, wherein when the fusion protein is expressed on the surface of the multivalent particle, the oligomerization domain is outside of the multivalent particle.

Embodiment 80. The multivalent particle of any one of embodiments 66-78, wherein when the fusion protein is expressed on the surface of the multivalent particle, the oligomerization domain is outside of the multivalent particle and adjacent to a signal peptide.

Embodiment 81. The multivalent particle of any one of embodiments 66-78, wherein when the fusion protein is expressed on the surface of the multivalent particle, the oligomerization domain is inside of the multivalent particle.

Embodiment 82. The multivalent particle of any one of embodiments 66-78, wherein when the fusion protein is expressed on the surface of the multivalent particle, the oligomerization domain is inside of the multivalent particle and adjacent to the transmembrane polypeptide.

Embodiment 83. The multivalent particle of any one of embodiments 66-82, wherein the fusion protein comprises a signal peptide.

Embodiment 84. The multivalent particle of any one of embodiments 66-82, wherein domains of the fusion protein are arranged from the N-terminus to the C-terminus in the following orders:

(a) signal peptide, extracellular domain of a viral entry receptor which binds to a surface protein of a virus, oligomerization domain, transmembrane polypeptide, and cytosolic domain;

(b) signal peptide, extracellular domain of a viral entry receptor which binds to a surface protein of a virus, transmembrane polypeptide, oligomerization domain, and cytosolic domain; or (c) signal peptide, oligomerization domain, extracellular domain of a viral entry receptor, transmembrane polypeptide, and cytosolic domain.

Embodiment 85. A composition comprising a first nucleic acid sequence encoding a multivalent particle comprising a fusion protein that comprises an extracellular domain of a viral entry receptor that binds to a viral protein and a transmembrane polypeptide wherein the fusion protein is expressed at least about 10 copies on a surface of the multivalent particle when the multivalent particle is expressed; and an excipient.

Embodiment 86. The composition of embodiment 85, wherein the viral protein is from SARS-CoV-1, SARS-CoV-2, MERS-CoV, Respiratory syncytial virus, HIV, or combinations thereof.

Embodiment 87. The composition of embodiment 85 or 86, further comprising a second nucleic acid sequence that encodes one or more packaging viral proteins.

Embodiment 88. The composition of embodiment 87, wherein the one or more packaging viral proteins is a lentiviral protein, a retroviral protein, an adenoviral protein, or combinations thereof.

Embodiment 89. The composition of embodiment 87, wherein the one or more packaging viral proteins comprises gag, pol, pre, tat, rev, or combinations thereof.

Embodiment 90. The composition of any one of embodiments 85-89, further comprising a third nucleic acid sequence that encodes a replication incompetent viral genome, a reporter, a therapeutic molecule, or combinations thereof.

Embodiment 91. The composition of embodiment 90, wherein the viral genome is derived from vesicular stomatitis virus, measles virus, Hepatitis virus, influenza virus, or combinations thereof.

Embodiment 92. The composition of embodiment 90, wherein the reporter is a fluorescent protein or luciferase.

Embodiment 93. The composition of embodiment 92, wherein the fluorescent protein is green fluorescent protein.

Embodiment 94. The composition of embodiment 90, wherein the therapeutic molecule is an immune modulating protein, a cellular signal modulating molecule, a proliferation modulating molecule, a cell death modulating molecule, or combinations thereof.

Embodiment 95. The composition of any one of embodiments 85-94, wherein the mammalian polypeptide comprises a receptor that has binding specificity for the viral protein.

Embodiment 96. The composition of embodiment 95, wherein the receptor comprises a viral entry receptor or a viral attachment receptor.

Embodiment 97. The composition of embodiment 95, wherein the receptor is both a viral entry receptor and a viral attachment receptor.

Embodiment 98. The composition of embodiment 95, wherein the mammalian polypeptide comprises an extracellular domain of the receptor.

Embodiment 99. The composition of any one of embodiments 85-94, wherein the mammalian polypeptide comprises a ligand or a secreted protein.

Embodiment 100. The composition of any one of embodiments 85-94, wherein the mammalian polypeptide comprises ACE2, TRMPSS2, DPP4, CD4, CCR5, CXCR4, CD209, or CLEC4M.

Embodiment 101. The composition of any one of embodiments 85-94, wherein the mammalian polypeptide comprises an amino acid sequence of at least 90% sequence identity to an amino acid sequence according to SEQ ID NO: 1.

Embodiment 102. The composition of any one of embodiments 85-94, wherein the mammalian polypeptide comprises an amino acid sequence of at least 90% sequence identity to an amino acid sequence according to SEQ ID NO: 2.

Embodiment 103. The composition of any one of embodiments 85-102, wherein the transmembrane polypeptide comprises a transmembrane anchoring protein.

Embodiment 104. The composition of any one of embodiments 85-102, wherein the transmembrane polypeptide comprises a spike glycoprotein transmembrane region, a mammalian membrane protein, an envelope protein, a nucleocapsid protein, or a cellular transmembrane protein.

Embodiment 105. The composition of any one of embodiments 85-102, wherein the transmembrane polypeptide comprises VSVG transmembrane region, spike protein S1 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120.

Embodiment 106. The composition of embodiment 105, wherein the VSVG transmembrane region comprises full length VSVG transmembrane region or a truncated VSVG transmembrane region.

Embodiment 107. The composition of embodiment 105, wherein the transmembrane polypeptide comprises a VSVG transmembrane region and a VSVG cytoplasmic tail.

Embodiment 108. The composition of any one of embodiments 85-102, wherein the transmembrane polypeptide comprises an amino acid sequence at least about 90% identical to that set forth in SEQ ID NO: 3.

Embodiment 109. The composition of any one of embodiments 85-102, wherein the transmembrane polypeptide comprises a amino acid sequence at least about 90% identical to that set forth in SEQ ID NO: 4.

Embodiment 110. The composition of any one of embodiments 1-65, wherein the fusion protein further comprises an oligomerization domain.

Embodiment 111. The composition of embodiment 66, wherein the oligomerization domain is a dimerization domain.

Embodiment 112. The composition of embodiment 68, wherein the dimerization domain comprises a leucine zipper dimerization domain.

Embodiment 113. The composition of embodiment 66, wherein the oligomerization domain is a trimerization domain.

Embodiment 114. The composition of embodiment 70, wherein the trimerization domain comprises a post-fusion oligomerization domain of viral surface protein.

Embodiment 115. The composition of embodiment 70, wherein the trimerization domain comprises a D4 post-fusion trimerization domain of VSV-G protein.

Embodiment 116. The composition of embodiment 70, wherein the trimerization domain comprises a Dengue E protein post-fusion trimerization domain.

Embodiment 117. The composition of embodiment 70, wherein the trimerization domain comprises a foldon trimerization domain.

Embodiment 118. The composition of embodiment 69, wherein the trimerization domain comprises human C-propeptide of α1(I) collagen.

Embodiment 119. The composition of embodiment 66, wherein the oligomerization domain is a tetramerization domain.

Embodiment 120. The composition of embodiment 75, wherein the tetramerization domain comprises an influenza neuraminidase stem domain.

Embodiment 121. The composition of embodiment 66, wherein the oligomerization domain comprises an amino acid sequence that has at least 95% sequence identity to an amino acid sequence according to SEQ ID NOs: 5-18, or 28.

Embodiment 122. The composition of any one of embodiments 66-78, wherein when the fusion protein is expressed on the surface of the multivalent particle, the oligomerization domain is outside of the multivalent particle.

Embodiment 123. The composition of any one of embodiments 66-78, wherein when the fusion protein is expressed on the surface of the multivalent particle, the oligomerization domain is outside of the multivalent particle and adjacent to a signal peptide.

Embodiment 124. The composition of any one of embodiments 66-78, wherein when the fusion protein is expressed on the surface of the multivalent particle, the oligomerization domain is inside of the multivalent particle.

Embodiment 125. The composition of any one of embodiments 66-78, wherein when the fusion protein is expressed on the surface of the multivalent particle, the oligomerization domain is inside of the multivalent particle and adjacent to the transmembrane polypeptide.

Embodiment 126. The composition of any one of embodiments 85-109, wherein the fusion protein is expressed at least about 50 copies on a surface of the multivalent particle when it is expressed.

Embodiment 127. The composition of any one of embodiments 85-109, wherein the fusion protein is expressed at least about 75 copies on a surface of the multivalent particle when it is expressed.

Embodiment 128. The composition of any one of embodiments 85-109, wherein the fusion protein is expressed at least about 100 copies on a surface of the multivalent particle when it is expressed.

Embodiment 129. The composition of any one of embodiments 85-109, wherein the fusion protein is expressed at least about 150 copies on a surface of the multivalent particle when it is expressed.

Embodiment 130. The composition of any one of embodiments 85-109, wherein the fusion protein is expressed at least about 200 copies on a surface of the multivalent particle when it is expressed.

Embodiment 131. The composition of embodiment 85, wherein the mammalian polypeptide comprises ACE2 and the transmembrane polypeptide comprises VSVG transmembrane region.

Embodiment 132. The composition of embodiment 85, wherein the mammalian polypeptide comprises ACE2 and the transmembrane polypeptide comprises spike protein S2 transmembrane region.

Embodiment 133. The composition of embodiment 85, wherein the mammalian polypeptide comprises ACE2 and the transmembrane polypeptide comprises a surface glycoprotein of an enveloped virus.

Embodiment 134. The composition of embodiment 85, wherein the mammalian polypeptide comprises DPP4 and the transmembrane polypeptide comprises hemagglutinin envelope protein from measles virus.

Embodiment 135. The composition of embodiment 118, wherein the hemagglutinin envelope protein from measles virus is a variant of the hemagglutinin envelope protein from measles virus.

Embodiment 136. The composition of any one of embodiments 90-119, wherein the composition further comprises a fourth nucleic acid sequence encoding a second fusion protein that comprises a second mammalian polypeptide that binds to the viral protein and a second transmembrane polypeptide wherein the second fusion protein is expressed at least about 10 copies on the surface of the multivalent particle when it is expressed.

Embodiment 137. The composition of embodiment 120, wherein the second mammalian polypeptide comprises a receptor that has binding specificity for the viral protein.

Embodiment 138. The composition of embodiment 121, wherein the receptor comprises a viral entry receptor or a viral attachment receptor.

Embodiment 139. The composition of embodiment 121, wherein the receptor is both a viral entry receptor and a viral attachment receptor.

Embodiment 140. The composition of embodiment 121, wherein the second mammalian polypeptide comprises an extracellular domain of the receptor.

Embodiment 141. The composition of embodiment 120, wherein the second mammalian polypeptide comprises a ligand or a secreted protein.

Embodiment 142. The composition of embodiment 120, wherein the second mammalian polypeptide comprises ACE2, TRMPSS2, DPP4, CD4, CCR5, CXCR4, CD209, or CLEC4M.

Embodiment 143. The composition of embodiment 120, wherein the second mammalian polypeptide comprises an amino acid sequence of at least 90% sequence identity to an amino acid sequence according to SEQ ID NO: 1.

Embodiment 144. The composition of embodiment 120, wherein the second mammalian polypeptide comprises an amino acid sequence of at least 90% sequence identity to an amino acid sequence according to SEQ ID NO: 2.

Embodiment 145. The composition of any one of embodiments 120-128, wherein the second transmembrane polypeptide comprises a transmembrane anchoring protein.

Embodiment 146. The composition of any one of embodiments 120-128, wherein the second transmembrane polypeptide comprises a spike glycoprotein transmembrane region, a mammalian membrane protein, an envelope protein, a nucleocapsid protein, or a cellular transmembrane protein.

Embodiment 147. The composition of any one of embodiments 120-128, wherein the second transmembrane polypeptide comprises VSVG transmembrane region, spike protein 51 transmembrane region, spike protein S2 transmembrane region, Sindbis virus envelope (SINDBIS) protein, hemagglutinin envelope protein from measles virus, envelope glycoprotein of measles virus fusion (F) protein, RD114, BaEV, GP41, or GP120.

Embodiment 148. The composition of embodiment 131, wherein the VSVG transmembrane region comprises full length VSVG transmembrane region or a truncated VSVG transmembrane region.

Embodiment 149. The composition of embodiment 131, wherein the VSVG transmembrane region comprises a VSVG transmembrane region and a VSVG cytoplasmic tail.

Embodiment 150. The composition of any one of embodiments 120-128, wherein the second transmembrane polypeptide comprises an amino acid sequence at least about 90% identical to that set forth in SEQ ID NO: 3.

Embodiment 151. The composition of any one of embodiments 120-128, wherein the second transmembrane polypeptide comprises an amino acid sequence at least about 90% identical to that set forth in SEQ ID NO: 4.

Embodiment 152. The composition of any one of embodiments 1-65, wherein the second fusion protein further comprises an oligomerization domain.

Embodiment 153. The composition of embodiment 66, wherein the oligomerization domain is a dimerization domain.

Embodiment 154. The composition of embodiment 68, wherein the dimerization domain comprises a leucine zipper dimerization domain.

Embodiment 155. The composition of embodiment 66, wherein the oligomerization domain is a trimerization domain.

Embodiment 156. The composition of embodiment 70, wherein the trimerization domain comprises a post-fusion oligomerization domain of viral surface protein.

Embodiment 157. The composition of embodiment 70, wherein the trimerization domain comprises a D4 post-fusion trimerization domain of VSV-G protein.

Embodiment 158. The composition of embodiment 70, wherein the trimerization domain comprises a Dengue E protein post-fusion trimerization domain.

Embodiment 159. The composition of embodiment 70, wherein the trimerization domain comprises a foldon trimerization domain.

Embodiment 160. The composition of embodiment 69, wherein the trimerization domain comprises human C-propeptide of $\alpha 1(I)$ collagen.

Embodiment 161. The composition of embodiment 66, wherein the oligomerization domain is a tetramerization domain.

Embodiment 162. The composition of embodiment 75, wherein the tetramerization domain comprises an influenza neuraminidase stem domain.

Embodiment 163. The composition of embodiment 66, wherein the oligomerization domain comprises an amino acid sequence that has at least 95% sequence identity to an amino acid sequence according to SEQ ID NOs: 5-18, or 28.

Embodiment 164. The composition of any one of embodiments 66-78, wherein when the second fusion protein is expressed on the surface of the multivalent particle, the oligomerization domain is outside of the multivalent particle.

Embodiment 165. The composition of any one of embodiments 66-78, wherein when the second fusion protein is expressed on the surface of the multivalent particle, the oligomerization domain is outside of the multivalent particle and adjacent to a signal peptide.

Embodiment 166. The composition of any one of embodiments 66-78, wherein when the second fusion protein is expressed on the surface of the multivalent particle, the oligomerization domain is inside of the multivalent particle.

Embodiment 167. The composition of any one of embodiments 66-78, wherein when the second fusion protein is expressed on the surface of the multivalent particle, the oligomerization domain is inside of the multivalent particle and adjacent to the transmembrane polypeptide.

Embodiment 168. The composition of any one of embodiments 120-135, wherein the second fusion protein is expressed at least about 50 copies on a surface of the multivalent particle when it is expressed.

Embodiment 169. The composition of any one of embodiments 120-135, wherein the second fusion protein is expressed at least about 75 copies on a surface of the multivalent particle when it is expressed.

Embodiment 170. The composition of any one of embodiments 120-135, wherein the second fusion protein is expressed at least about 100 copies on a surface of the multivalent particle when it is expressed.

Embodiment 171. The composition of any one of embodiments 120-135, wherein the second fusion protein is expressed at least about 150 copies on a surface of the multivalent particle when it is expressed.

Embodiment 172. The composition of any one of embodiments 120-135, wherein the second fusion protein is expressed at least about 200 copies on a surface of the multivalent particle when it is expressed.

Embodiment 173. The composition of embodiment 120, wherein the second mammalian polypeptide comprises ACE2 and the second transmembrane polypeptide comprises VSVG transmembrane region.

Embodiment 174. The composition of embodiment 120, wherein the second mammalian polypeptide comprises ACE2 and the second transmembrane polypeptide comprises spike protein S2 transmembrane region.

Embodiment 175. The composition of embodiment 120, wherein the second mammalian polypeptide comprises ACE2 and the second transmembrane polypeptide comprises a surface glycoprotein of an enveloped virus.

Embodiment 176. The composition of embodiment 120, wherein the second mammalian polypeptide comprises DPP4 and the second transmembrane polypeptide comprises hemagglutinin envelope protein from measles virus.

Embodiment 177. The composition of embodiment 144, wherein the hemagglutinin envelope protein from measles virus is a variant of the hemagglutinin envelope protein from measles virus.

Embodiment 178. The composition of embodiment 120, wherein the mammalian polypeptide comprises a viral entry receptor and the second mammalian polypeptide comprises a viral attachment receptor.

Embodiment 179. The composition of embodiment 120, wherein the mammalian polypeptide comprises ACE2, the transmembrane polypeptide comprises VSVG transmembrane region, spike protein S1 transmembrane region, spike protein S2 transmembrane region, or a surface glycoprotein of an enveloped virus, the second mammalian polypeptide comprises a heparan sulfate proteoglycan, and the second transmembrane polypeptide comprises VSVG transmembrane region, spike protein S1 transmembrane region, spike protein S2 transmembrane region, or a surface glycoprotein of an enveloped virus.

Embodiment 180. The composition of embodiment 120, wherein the mammalian polypeptide comprises CD4 and the second mammalian peptide comprises, CCR5, CXCR4, or both.

Embodiment 181. The composition of embodiment 90, wherein the first nucleic acid sequence, the second nucleic acid sequence, and the third nucleic acid sequence are within a same vector.

Embodiment 182. The composition of embodiment 90, wherein the first nucleic acid sequence, the second nucleic acid sequence, and the third nucleic acid sequence are within different vectors.

Embodiment 183. The composition of embodiment 120, wherein the first nucleic acid sequence, the second nucleic acid sequence, the third nucleic acid sequence, and the fourth nucleic acid sequence are within a same vector.

Embodiment 184. The composition of embodiment 120, wherein the first nucleic acid sequence, the second nucleic acid sequence, third nucleic acid sequence, and the fourth nucleic acid sequence are within different vectors.

Embodiment 185. The composition of embodiment 118, wherein the nucleic acid sequence that encodes the first fusion protein and the second fusion protein and the second nucleic acid sequence and the third nucleic acid sequence are mRNAs.

Embodiment 186. The composition of embodiment 118, wherein the nucleic acid sequence that encodes the first fusion protein and the second fusion protein and the second nucleic acid sequence and the third nucleic acid sequence are DNA.

Embodiment 187. The composition of any one of embodiments 149, wherein the composition comprises a vector, wherein the vector is a lentivirus vector, an adenovirus vector, or an adeno-associated virus vector.

Embodiment 188. A pharmaceutical composition comprising the multivalent particle of any one of embodiments 1-84 and a pharmaceutically acceptable excipient.

Embodiment 189. A method of treating a viral infection in a subject in need thereof, comprising administering to the subject the multivalent particle of any one of embodiments 1-84 or the composition of any one of embodiments 85-187.

Embodiment 190. The method of embodiment 189, wherein the multivalent particle is administered intravenously.

Embodiment 191. The method of embodiment 189, wherein the multivalent particle is administered through inhalation.

Embodiment 192. The method of embodiment 189, wherein the multivalent particle is administered by an intraperitoneal injection.

Embodiment 193. The method of embodiment 189, wherein the multivalent particle is administered by a subcutaneous injection.

Embodiment 194. The method of embodiment 189, wherein the viral infection comprises an infection by SARS CoV-2, SARS CoV-1, MERS CoV.

Embodiment 195. The method of embodiment 189, wherein the composition is administered intravenously.

Embodiment 196. The method of embodiment 189, wherein the composition is administered through inhalation.

Embodiment 197. The method of embodiment 189, wherein the composition is administered by an intraperitoneal injection.

Embodiment 198. The method of embodiment 189, wherein the composition is administered by a subcutaneous injection.

Embodiment 199. The method of embodiment 189, wherein the composition comprises a liposome.

Embodiment 200. The method of embodiment 189, wherein the composition comprises an adeno-associated virus (AAV)

Embodiment 201. The method of embodiment 189, wherein the composition comprises a lipid nanoparticle.

Embodiment 202. The method of embodiment 189, wherein the composition comprises a polymer.

Embodiment 203. The method of embodiment 194, wherein the SARS CoV-2, SARS CoV-1, MERS CoV are effectively neutralized in vivo by the multivalent particle or the composition.

Embodiment 204. The method of embodiment 189, wherein the multivalent particle or the composition inhibits a respiratory symptom of the viral infection.

Embodiment 205. The method of embodiment 189, wherein the multivalent particle or the composition induces robust immunity against different strains of the viral infection.

Embodiment 206. The method of embodiment 189, wherein the viral infection comprises infection by SARS CoV-2, and the multivalent particle or the composition induces robust immunity against Delta variant of SARS CoV-2.

Embodiment 207. A method of producing immunity against a viral infection in a subject in need thereof, comprising administering to the subject the multivalent particle of any one of embodiments 1-84 or the composition of any one of embodiments 85-187 and a virus of the viral infection.

Embodiment 208. The method of embodiment 207, wherein the multivalent particle is administered intravenously.

Embodiment 209. The method of embodiment 207, wherein the multivalent particle is administered through inhalation.

Embodiment 210. The method of embodiment 207, wherein the multivalent particle is administered by an intraperitoneal injection.

Embodiment 211. The method of embodiment 207, wherein the multivalent particle is administered by a subcutaneous injection.

Embodiment 212. The method of any one of embodiments 207-211, wherein the viral infection comprises an infection by SARS CoV-2, SARS CoV-1, MERS CoV.

Embodiment 213. The method of any one of embodiments 207-212, wherein the composition is administered intravenously.

Embodiment 214. The method of any one of embodiments 207-212, wherein the composition is administered through inhalation.

Embodiment 215. The method of any one of embodiments 207-212, wherein the composition is administered by an intraperitoneal injection.

Embodiment 216. The method of any one of embodiments 207-212, wherein the composition is administered by a subcutaneous injection.

Embodiment 217. The method of any one of embodiments 207-216, wherein the composition comprises a liposome.

Embodiment 218. The method of any one of embodiments 207-217, wherein the composition comprises an adeno-associated virus (AAV)

Embodiment 219. The method of any one of embodiments 207-218, wherein the composition comprises a lipid nanoparticle.

Embodiment 220. The method of any one of embodiments 207-219, wherein the composition comprises a polymer.

Embodiment 221. The method of any one of embodiments 207-220, wherein the SARS CoV-2, SARS CoV-1, MERS CoV are effectively neutralized in vivo by the multivalent particle or the composition.

Embodiment 222. The method of any one of embodiments 207-221, wherein the multivalent particle or the composition inhibits a respiratory symptom of the viral infection.

Embodiment 223. The method of any one of embodiments 207-222, wherein the multivalent particle or the composition induces robust immunity against different strains of the viral infection.

Embodiment 224. The method of any one of embodiments 207-223, wherein the viral infection comprises infection by SARS CoV-2, and the multivalent particle or the composition induces robust immunity against Delta variant of SARS CoV-2.

---

What is claimed is:

1. A multivalent particle comprising a fusion protein that comprises a mammalian polypeptide that binds to a viral protein and a transmembrane region of a transmembrane polypeptide wherein the fusion protein is expressed at least 10 copies on a surface of the multivalent particle, wherein the transmembrane polypeptide comprises an amino acid sequence that has at least 90% sequence identity to the amino acid sequence according to SEQ ID NO: 3 (Vesicular stomatitis virus G or VSVG) or an amino acid sequence that has at least 90% sequence identity to the amino acid sequence according to SEQ ID NO: 4 (SARS-COV-2 spike protein), and wherein the mammalian polypeptide comprises an amino acid sequence that has at least 90% sequence identity to the amino acid sequence according to SEQ ID NO: 1 (angiotensin-converting enzyme 2 or ACE2).

2. The multivalent particle of claim 1, wherein the viral protein is from severe acute respiratory syndrome coronavirus 1 (SARS-CoV-1), severe acute respiratory syndrome coronavirus 2 (SARS-CoV-2), Middle East respiratory syndrome-related coronavirus (MERS-CoV), syncytial virus, human immunodeficiency virus (HIV), or combinations thereof.

3. The multivalent particle of claim 1, wherein the mammalian polypeptide comprises an amino acid sequence that has 100% sequence identity to the amino acid sequence according to SEQ ID NO: 1 (ACE2).

4. The multivalent particle of claim 1, wherein the transmembrane region of the transmembrane polypeptide anchors the fusion protein to a bilayer of the multivalent particle.

5. The multivalent particle of claim 1, wherein the transmembrane polypeptide comprises an amino acid sequence that has 100% sequence identity to the amino acid sequence according to SEQ ID NO: 3 (VSVG) or an amino acid sequence that has 100% sequence identity to the amino acid sequence according to SEQ ID NO: 4 (SARS-COV-2 spike protein).

6. The multivalent particle of claim 1, wherein the fusion protein is expressed at least 50 copies on a surface of the multivalent particle.

7. The multivalent particle of claim 1, wherein the fusion protein is expressed at least 75 copies on a surface of the multivalent particle.

8. The multivalent particle of claim 1, wherein the fusion protein is expressed at least 100 copies on a surface of the multivalent particle.

9. The multivalent particle of claim 1, wherein the fusion protein is expressed at least 150 copies on a surface of the multivalent particle.

10. The multivalent particle of claim 1, wherein the fusion protein is expressed at least 200 copies on a surface of the multivalent particle.

11. The multivalent particle of claim 1, wherein the transmembrane polypeptide comprises the amino acid sequence that has at least 90% sequence identity to the amino acid sequence according to SEQ ID NO: 3 (VSVG).

12. The multivalent particle of claim 1, wherein the transmembrane polypeptide comprises the amino acid sequence that has at least 90% sequence identity to the amino acid sequence according to SEQ ID NO: 4 (SARS-COV-2 spike protein).

13. The multivalent particle of claim 1, wherein the fusion protein further comprises an oligomerization domain.

14. The multivalent particle of claim 13, wherein the oligomerization domain is a trimerization domain, wherein the trimerization domain comprises a post-fusion oligomerization domain of viral surface protein.

15. The multivalent particle of claim 13, wherein the oligomerization domain is a trimerization domain, wherein the trimerization domain comprises a D4 post-fusion trimerization domain of VSV-G protein.

16. The multivalent particle of claim 13, wherein the oligomerization domain comprises an amino acid sequence that has at least 95% sequence identity to an amino acid sequence according to any one of SEQ ID NOs: 5-18 and 28.

* * * * *

SEQUENCE LISTING

```
<160> NUMBER OF SEQ ID NOS: 35

<210> SEQ ID NO 1
<211> LENGTH: 805
<212> TYPE: PRT
<213> ORGANISM: Homo sapiens

<400> SEQUENCE: 1

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140
```

```
Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
            165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560
```

```
Gly Lys Ser Glu Pro Trp Thr Leu Ala Leu Glu Asn Val Val Gly Ala
            565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
            610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
            770                 775                 780

Asp Ile Ser Lys Gly Glu Asn Asn Pro Gly Phe Gln Asn Thr Asp Asp
785                 790                 795                 800

Val Gln Thr Ser Phe
            805

<210> SEQ ID NO 2
<211> LENGTH: 766
<212> TYPE: PRT
<213> ORGANISM: Homo sapiens

<400> SEQUENCE: 2

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
            35                  40                  45

Leu Lys Asn Thr Tyr Arg Leu Lys Leu Tyr Ser Leu Arg Trp Ile Ser
            50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
            85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
            115                 120                 125
```

```
Thr Ala Ser Tyr Asp Ile Tyr Asp Leu Asn Lys Arg Gln Leu Ile Thr
        130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
        340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
        370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
        530                 535                 540
```

```
Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 3
<211> LENGTH: 495
<212> TYPE: PRT
<213> ORGANISM: Indiana vesiculovirus

<400> SEQUENCE: 3

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
                20                  25                  30

His Asn Asp Leu Ile Gly Thr Ala Leu Gln Val Lys Met Pro Lys Ser
            35                  40                  45

His Lys Ala Ile Gln Ala Asp Gly Trp Met Cys His Ala Ser Lys Trp
        50                  55                  60

Val Thr Thr Cys Asp Phe Arg Trp Tyr Gly Pro Lys Tyr Ile Thr His
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
                100                 105                 110

Ser Cys Gly Tyr Ala Thr Val Thr Asp Ala Glu Ala Val Ile Val Gln
            115                 120                 125

Val Thr Pro His His Val Leu Val Asp Glu Tyr Thr Gly Glu Trp Val
        130                 135                 140

Asp Ser Gln Phe Ile Asn Gly Lys Cys Ser Asn Tyr Ile Cys Pro Thr
145                 150                 155                 160
```

Val His Asn Ser Thr Thr Trp His Ser Asp Tyr Lys Val Lys Gly Leu
            165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
            195                 200                 205

Tyr Phe Ala Tyr Glu Thr Gly Gly Lys Ala Cys Lys Met Gln Tyr Cys
            210                 215                 220

Lys His Trp Gly Val Arg Leu Pro Ser Gly Val Trp Phe Glu Met Ala
225                 230                 235                 240

Asp Lys Asp Leu Phe Ala Ala Arg Phe Pro Glu Cys Pro Glu Gly
            245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
            275                 280                 285

Ser Lys Ile Arg Ala Gly Leu Pro Ile Ser Pro Val Asp Leu Ser Tyr
            290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
            325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
            355                 360                 365

Gly Pro Asn Gly Val Leu Arg Thr Ser Ser Gly Tyr Lys Phe Pro Leu
            370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
            405                 410                 415

Leu Pro Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
            435                 440                 445

Ile Ala Ser Phe Phe Phe Ile Ile Gly Leu Ile Ile Gly Leu Phe Leu
            450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
            485                 490                 495

<210> SEQ ID NO 4
<211> LENGTH: 1273
<212> TYPE: PRT
<213> ORGANISM: Severe acute respiratory syndrome coronavirus 2

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu

```
                  35                  40                  45
His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880
```

```
Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
        900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270
```

-continued

```
<210> SEQ ID NO 5
<211> LENGTH: 150
<212> TYPE: PRT
<213> ORGANISM: Indiana vesiculovirus

<400> SEQUENCE: 5

Ile Gly Thr Ala Leu Gln Val Lys Met Pro Lys Ser His Lys Ala Ile
1               5                   10                  15

Gln Ala Asp Gly Trp Met Cys His Ala Ser Lys Trp Val Thr Thr Cys
            20                  25                  30

Asp Phe Arg Trp Tyr Gly Pro Lys Tyr Ile Thr His Ser Ile Arg Ser
        35                  40                  45

Phe Thr Pro Ser Val Glu Gln Cys Lys Glu Ser Ile Glu Gln Thr Lys
    50                  55                  60

Gln Gly Thr Trp Leu Asn Pro Gly Phe Pro Pro Gln Ser Cys Gly Tyr
65                  70                  75                  80

Ala Thr Val Thr Asp Ala Glu Ala Val Ile Val Gln Val Thr Pro His
                85                  90                  95

His Val Leu Val Asp Glu Tyr Thr Gly Glu Trp Val Asp Ser Gln Phe
            100                 105                 110

Ile Asn Gly Lys Cys Ser Asn Tyr Ile Cys Pro Thr Val His Asn Ser
        115                 120                 125

Thr Thr Trp His Ser Asp Tyr Lys Val Lys Gly Leu Cys Asp Ser Asn
130                 135                 140

Leu Ile Ser Met Asp Ile
145                 150

<210> SEQ ID NO 6
<211> LENGTH: 130
<212> TYPE: PRT
<213> ORGANISM: Indiana vesiculovirus

<400> SEQUENCE: 6

Ile Gln Ala Asp Gly Trp Met Cys His Ala Ser Lys Trp Val Thr Thr
1               5                   10                  15

Cys Asp Phe Arg Trp Tyr Gly Pro Lys Tyr Ile Thr His Ser Ile Arg
            20                  25                  30

Ser Phe Thr Pro Ser Val Glu Gln Cys Lys Glu Ser Ile Glu Gln Thr
        35                  40                  45

Lys Gln Gly Thr Trp Leu Asn Pro Gly Phe Pro Pro Gln Ser Cys Gly
    50                  55                  60

Tyr Ala Thr Val Thr Asp Ala Glu Ala Val Ile Val Gln Val Thr Pro
65                  70                  75                  80

His His Val Leu Val Asp Glu Tyr Thr Gly Glu Trp Val Asp Ser Gln
                85                  90                  95

Phe Ile Asn Gly Lys Cys Ser Asn Tyr Ile Cys Pro Thr Val His Asn
            100                 105                 110

Ser Thr Thr Trp His Ser Asp Tyr Lys Val Lys Gly Leu Cys Asp Ser
        115                 120                 125

Asn Leu
    130

<210> SEQ ID NO 7
<211> LENGTH: 115
<212> TYPE: PRT
<213> ORGANISM: Indiana vesiculovirus

<400> SEQUENCE: 7
```

```
Ile Gln Ala Asp Gly Trp Met Cys His Ala Ser Lys Trp Val Thr Thr
1               5                   10                  15

Cys Asp Phe Arg Trp Tyr Gly Pro Lys Tyr Ile Thr His Ser Ile Arg
                20                  25                  30

Ser Phe Thr Pro Ser Val Glu Gln Cys Lys Glu Ser Ile Glu Gln Thr
            35                  40                  45

Lys Gln Gly Thr Trp Leu Asn Pro Gly Phe Pro Pro Gln Ser Cys Gly
        50                  55                  60

Tyr Ala Thr Val Thr Asp Ala Glu Ala Val Ile Val Gln Val Thr Pro
65                  70                  75                  80

His His Val Leu Val Asp Glu Tyr Thr Gly Glu Trp Val Asp Ser Gln
                85                  90                  95

Phe Ile Asn Gly Lys Cys Ser Asn Tyr Ile Cys Pro Thr Val His Asn
                100                 105                 110

Ser Thr Thr
        115
```

```
<210> SEQ ID NO 8
<211> LENGTH: 100
<212> TYPE: PRT
<213> ORGANISM: Indiana vesiculovirus

<400> SEQUENCE: 8

Ile Gln Ala Asp Gly Trp Met Cys His Ala Ser Lys Trp Val Thr Thr
1               5                   10                  15

Cys Asp Phe Arg Trp Tyr Gly Pro Lys Tyr Ile Thr His Ser Ile Arg
                20                  25                  30

Ser Phe Thr Pro Ser Val Glu Gln Cys Lys Glu Ser Ile Glu Gln Thr
            35                  40                  45

Lys Gln Gly Thr Trp Leu Asn Pro Gly Phe Pro Pro Gln Ser Cys Gly
        50                  55                  60

Tyr Ala Thr Val Thr Asp Ala Glu Ala Val Ile Val Gln Val Thr Pro
65                  70                  75                  80

His His Val Leu Val Asp Glu Tyr Thr Gly Glu Trp Val Asp Ser Gln
                85                  90                  95

Phe Ile Asn Gly
            100
```

```
<210> SEQ ID NO 9
<211> LENGTH: 84
<212> TYPE: PRT
<213> ORGANISM: Indiana vesiculovirus

<400> SEQUENCE: 9

Ile Gln Ala Asp Gly Trp Met Cys His Ala Ser Lys Trp Val Thr Thr
1               5                   10                  15

Cys Asp Phe Arg Trp Tyr Gly Pro Lys Tyr Ile Thr His Ser Ile Arg
                20                  25                  30

Ser Phe Thr Pro Ser Val Glu Gln Cys Lys Glu Ser Ile Glu Gln Thr
            35                  40                  45

Lys Gln Gly Thr Trp Leu Asn Pro Gly Phe Pro Pro Gln Ser Cys Gly
        50                  55                  60

Tyr Ala Thr Val Thr Asp Ala Glu Ala Val Ile Val Gln Val Thr Pro
65                  70                  75                  80

His His Val Leu
```

<210> SEQ ID NO 10
<211> LENGTH: 27
<212> TYPE: PRT
<213> ORGANISM: Unknown
<220> FEATURE:
<223> OTHER INFORMATION: Description of Unknown:
      Foldon sequence

<400> SEQUENCE: 10

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 11
<211> LENGTH: 33
<212> TYPE: PRT
<213> ORGANISM: Unknown
<220> FEATURE:
<223> OTHER INFORMATION: Description of Unknown:
      Leucine Zipper V1 sequence

<400> SEQUENCE: 11

Arg Met Lys Gln Leu Glu Asp Lys Val Glu Glu Leu Leu Ser Lys Gln
1               5                   10                  15

Tyr His Leu Glu Asn Glu Val Ala Arg Leu Lys Lys Leu Val Gly Glu
            20                  25                  30

Arg

<210> SEQ ID NO 12
<211> LENGTH: 33
<212> TYPE: PRT
<213> ORGANISM: Unknown
<220> FEATURE:
<223> OTHER INFORMATION: Description of Unknown:
      Leucine Zipper V2 sequence

<400> SEQUENCE: 12

Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val Gly Glu
            20                  25                  30

Arg

<210> SEQ ID NO 13
<211> LENGTH: 40
<212> TYPE: PRT
<213> ORGANISM: Influenza virus

<400> SEQUENCE: 13

Met Asn Pro Asn Gln Lys Ile Ile Thr Ile Gly Ser Ile Cys Leu Val
1 5 10 15

Val Gly Leu Ile Ser Leu Ile Leu Gln Ile Gly Asn Ile Ile Ser Ile
20 25 30

Trp Ile Ser His Ser Ile Gln Thr
35 40

<210> SEQ ID NO 14
<211> LENGTH: 75
<212> TYPE: PRT
<213> ORGANISM: Influenza virus

<400> SEQUENCE: 14

```
Met Asn Pro Asn Gln Lys Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
            35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn
65                  70                  75

<210> SEQ ID NO 15
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Leu Cys Ile Glu Ala Lys Ile Ser Asn Thr Thr Thr Asp Ser Arg
1               5                   10                  15

Cys Pro Thr Gln Gly Glu Ala Thr Leu Val Glu Glu Gln Asp Thr Asn
            20                  25                  30

Phe Val Cys Arg Arg Thr Phe Val Asp Arg Gly His Gly Asn Gly Cys
            35                  40                  45

Gly Leu Phe Gly Lys Gly Ser Leu Ile Thr Cys Ala Lys Phe Lys Cys
    50                  55                  60

Val Thr Lys Leu
65

<210> SEQ ID NO 16
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile Glu Leu Leu Lys Thr Glu Val Thr Asn Pro Ala Val Leu Arg Lys
1               5                   10                  15

Leu Cys Ile Glu Ala Lys Ile Ser Asn Thr Thr Thr Asp Ser Arg Cys
            20                  25                  30

Pro Thr Gln Gly Glu Ala Thr Leu Val Glu Glu Gln Asp Thr Asn Phe
            35                  40                  45

Val Cys Arg Arg Thr Phe Val Asp Arg Gly His Gly Asn Gly Cys Gly
    50                  55                  60

Leu Phe Gly Lys Gly Ser Leu Ile Thr Cys Ala Lys Phe Lys Cys Val
65                  70                  75                  80

Thr Lys Leu

<210> SEQ ID NO 17
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 17

Lys Leu Cys Ile Glu Ala Lys Ile Ser Asn Thr Thr Thr Asp Ser Arg
1               5                   10                  15

Cys Pro Thr Gln Gly Glu Ala Thr Leu Val Glu Glu Gln Asp Thr Asn
            20                  25                  30

Phe Val Cys Arg Arg Thr Phe Val Asp Arg Gly His Gly Asn Gly Cys
        35                  40                  45

Gly Leu Phe Gly Lys Gly Ser Leu Ile Thr Cys Ala Lys Phe Lys Cys
    50                  55                  60

Val Thr Lys Leu Glu Gly Lys Ile Val Gln Tyr Glu Asn Leu Lys Tyr
65                  70                  75                  80

Ser Val Ile

<210> SEQ ID NO 18
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ala Lys Ile Ser Asn Thr Thr Thr Asp Ser Arg Cys Pro Thr Gln
1               5                   10                  15

Gly Glu Ala Thr Leu Val Glu Glu Gln Asp Thr Asn Phe Val Cys Arg
            20                  25                  30

Arg Thr Phe Val Asp Arg Gly His Gly Asn Gly Cys Gly Leu Phe Gly
        35                  40                  45

Lys Gly Ser Leu Ile Thr Cys Ala Lys Phe Lys
    50                  55

<210> SEQ ID NO 19
<211> LENGTH: 22
<212> TYPE: PRT
<213> ORGANISM: Indiana vesiculovirus

<400> SEQUENCE: 19

Ile Ala Ser Phe Phe Phe Ile Ile Gly Leu Ile Ile Gly Leu Phe Leu
1               5                   10                  15

Val Leu Arg Val Gly Ile
            20

<210> SEQ ID NO 20
<211> LENGTH: 37
<212> TYPE: PRT
<213> ORGANISM: Indiana vesiculovirus

<400> SEQUENCE: 20

Pro Ile Glu Leu Val Glu Gly Trp Phe Ser Ser Trp Lys Ser Ser Ile
1               5                   10                  15

Ala Ser Phe Phe Phe Ile Ile Gly Leu Ile Ile Gly Leu Phe Leu Val
            20                  25                  30

Leu Arg Val Gly Ile
        35

<210> SEQ ID NO 21
<211> LENGTH: 53
<212> TYPE: PRT
<213> ORGANISM: Indiana vesiculovirus
```

```
<400> SEQUENCE: 21

Asp Asp Glu Ser Leu Phe Phe Gly Asp Thr Gly Leu Ser Lys Asn Pro
1               5                   10                  15

Ile Glu Leu Val Glu Gly Trp Phe Ser Ser Trp Lys Ser Ser Ile Ala
            20                  25                  30

Ser Phe Phe Phe Ile Ile Gly Leu Ile Ile Gly Leu Phe Leu Val Leu
        35                  40                  45

Arg Val Gly Ile His
    50

<210> SEQ ID NO 22
<211> LENGTH: 81
<212> TYPE: PRT
<213> ORGANISM: Indiana vesiculovirus

<400> SEQUENCE: 22

Gly Met Leu Asp Ser Asp Leu His Leu Ser Ser Lys Ala Gln Val Phe
1               5                   10                  15

Glu His Pro His Ile Gln Asp Ala Ala Ser Gln Leu Pro Asp Asp Glu
            20                  25                  30

Ser Leu Phe Phe Gly Asp Thr Gly Leu Ser Lys Asn Pro Ile Glu Leu
        35                  40                  45

Val Glu Gly Trp Phe Ser Ser Trp Lys Ser Ser Ile Ala Ser Phe Phe
    50                  55                  60

Phe Ile Ile Gly Leu Ile Ile Gly Leu Phe Leu Val Leu Arg Val Gly
65                  70                  75                  80

Ile

<210> SEQ ID NO 23
<211> LENGTH: 25
<212> TYPE: PRT
<213> ORGANISM: Indiana vesiculovirus

<400> SEQUENCE: 23

His Leu Cys Ile Lys Leu Lys His Thr Lys Lys Arg Gln Ile Tyr Thr
1               5                   10                  15

Asp Ile Glu Met Asn Arg Leu Gly Lys
            20                  25

<210> SEQ ID NO 24
<211> LENGTH: 23
<212> TYPE: PRT
<213> ORGANISM: Influenza virus

<400> SEQUENCE: 24

Ile Ile Thr Ile Gly Ser Val Cys Met Thr Ile Gly Met Ala Asn Leu
1               5                   10                  15

Ile Leu Gln Ile Gly Asn Ile
            20

<210> SEQ ID NO 25
<211> LENGTH: 23
<212> TYPE: PRT
<213> ORGANISM: Influenza virus

<400> SEQUENCE: 25

Leu Ala Ile Tyr Ser Thr Val Ala Ser Ser Leu Val Leu Val Val Ser
1               5                   10                  15

Leu Gly Ala Ile Ser Phe Trp
```

20

<210> SEQ ID NO 26
<211> LENGTH: 52
<212> TYPE: PRT
<213> ORGANISM: Dengue virus

<400> SEQUENCE: 26

Ala Tyr Gly Val Leu Phe Ser Gly Val Ser Trp Thr Met Lys Ile Gly
1 5 10 15

Ile Gly Ile Leu Leu Thr Trp Leu Gly Leu Asn Ser Arg Ser Thr Ser
20 25 30

Leu Ser Met Thr Cys Ile Ala Val Gly Met Val Thr Leu Tyr Leu Gly
35 40 45

Val Met Val Gln
50

<210> SEQ ID NO 27
<211> LENGTH: 21
<212> TYPE: PRT
<213> ORGANISM: Human immunodeficiency virus

<400> SEQUENCE: 27

Phe Ile Met Ile Val Gly Gly Leu Val Gly Leu Arg Ile Val Phe Ala
1 5 10 15

Val Leu Ser Ile Val
20

<210> SEQ ID NO 28
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Glu Thr Gly His His His His His His Ser Ala Asp Glu Pro Met Asp
1 5 10 15

Phe Lys Ile Asn Thr Asp Glu Ile Met Thr Ser Leu Lys Ser Val Asn
20 25 30

Gly Gln Ile Glu Ser Leu Ile Ser Pro Asp Gly Ser Arg Lys Asn Pro
35 40 45

Ala Arg Asn Cys Arg Asp Leu Lys Phe Cys His Pro Glu Leu Lys Ser
50 55 60

Gly Glu Tyr Trp Val Asp Pro Asn Gln Gly Cys Lys Leu Asp Ala Ile
65 70 75 80

Lys Val Phe Cys Asn Met Glu Thr Gly Glu Thr Cys Ile Ser Ala Asn
85 90 95

Pro Leu Asn Val Pro Arg Lys His Trp Trp Thr Asp Ser Ser Ala Glu
100 105 110

Lys Lys His Val Trp Phe Gly Glu Ser Met Asp Gly Gly Phe Gln Phe
115 120 125

Ser Tyr Gly Asn Pro Glu Leu Pro Glu Asp Val Leu Asp Val Gln Leu
130 135 140

Ala Phe Leu Arg Leu Leu Ser Ser Arg Ala Ser Gln Gln Ile Thr Tyr
145 150 155 160

His Cys Lys Asn Ser Ile Ala Tyr Met Asp Gln Ala Ser Gly Asn Val
165 170 175

```
Lys Lys Ala Leu Lys Leu Met Gly Ser Asn Glu Gly Glu Phe Lys Ala
            180                 185                 190

Glu Gly Asn Ser Lys Phe Thr Tyr Thr Val Leu Glu Asp Gly Cys Thr
        195                 200                 205

Lys His Thr Gly Glu Trp Ser Lys Thr Val Phe Glu Tyr Arg Thr Arg
    210                 215                 220

Lys Ala Val Arg Leu Pro Ile Val Asp Ile Ala Pro Tyr Asp Ile Gly
225                 230                 235                 240

Gly Pro Asp Gln Glu Phe Gly Val Asp Val Gly Pro Val Cys Phe Leu
                245                 250                 255

<210> SEQ ID NO 29
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
```

```
            275                 280                 285
Pro Asn Ile Asp Val Thr Asp Ala Met Val Asp Gln Ala Trp Asp Ala
            290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
                355                 360                 365
Phe Leu Thr Ala His His Glu Met Gly His Ile Gln Tyr Asp Met Ala
            370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Gly
            435                 440                 445
Thr Leu Pro Phe Thr Tyr Met Leu Glu Lys Trp Arg Trp Met Val Phe
450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
                500                 505                 510
Ile Arg Tyr Tyr Thr Arg Thr Leu Tyr Gln Phe Gln Phe Gln Glu Ala
            515                 520                 525
Leu Cys Gln Ala Ala Lys His Glu Gly Pro Leu His Lys Cys Asp Ile
            530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
                580                 585                 590
Thr Trp Leu Lys Asp Gln Asn Lys Asn Ser Phe Val Gly Trp Ser Thr
            595                 600                 605
Asp Trp Ser Pro Tyr Ala Asp Gln Ser Ile Lys Val Arg Ile Ser Leu
            610                 615                 620
Lys Ser Ala Leu Gly Asp Lys Ala Tyr Glu Trp Asn Asp Asn Glu Met
625                 630                 635                 640
Tyr Leu Phe Arg Ser Ser Val Ala Tyr Ala Met Arg Gln Tyr Phe Leu
                645                 650                 655
Lys Val Lys Asn Gln Met Ile Leu Phe Gly Glu Glu Asp Val Arg Val
                660                 665                 670
Ala Asn Leu Lys Pro Arg Ile Ser Phe Asn Phe Phe Val Thr Ala Pro
            675                 680                 685
Lys Asn Val Ser Asp Ile Ile Pro Arg Thr Glu Val Glu Lys Ala Ile
            690                 695                 700
```

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ser Arg Gly Met Leu Asp Ser Asp Leu His Leu Ser
            740                 745                 750

Ser Lys Ala Gln Val Phe Glu His Pro His Ile Gln Asp Ala Ala Ser
        755                 760                 765

Gln Leu Pro Asp Asp Glu Ser Leu Phe Phe Gly Asp Thr Gly Leu Ser
    770                 775                 780

Lys Asn Pro Ile Glu Leu Val Glu Gly Trp Phe Ser Ser Trp Lys Ser
785                 790                 795                 800

Ser Ile Ala Ser Phe Phe Phe Ile Ile Gly Leu Ile Ile Gly Leu Phe
                805                 810                 815

Leu Val Leu Arg Val Gly Ile His Leu Cys Ile Lys Leu Lys His Thr
            820                 825                 830

Lys Lys Arg Gln Ile Tyr Thr Asp Ile Glu Met Asn Arg Leu Gly Lys
        835                 840                 845

<210> SEQ ID NO 30
<211> LENGTH: 1344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu

```
                210                 215                 220
Asp Val Glu His Thr Phe Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
                275                 280                 285

Pro Asn Ile Asp Val Thr Asp Ala Met Val Asp Gln Ala Trp Asp Ala
                290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
                370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
                435                 440                 445

Thr Leu Pro Phe Thr Tyr Met Leu Glu Lys Trp Arg Trp Met Val Phe
                450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Gln Ser Ile Lys Val Arg Ile Ser Leu
                610                 615                 620

Lys Ser Ala Leu Gly Asp Lys Ala Tyr Glu Trp Asn Asp Asn Glu Met
625                 630                 635                 640
```

```
Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Asp Ile Gly Gly Ser Val Ala Ser Gln Ser Ile
                740                 745                 750

Ile Ala Tyr Thr Met Ser Leu Gly Ala Glu Asn Ser Val Ala Tyr Ser
                755                 760                 765

Asn Asn Ser Ile Ala Ile Pro Thr Asn Phe Thr Ile Ser Val Thr Thr
770                 775                 780

Glu Ile Leu Pro Val Ser Met Thr Lys Thr Ser Val Asp Cys Thr Met
785                 790                 795                 800

Tyr Ile Cys Gly Asp Ser Thr Glu Cys Ser Asn Leu Leu Leu Gln Tyr
                805                 810                 815

Gly Ser Phe Cys Thr Gln Leu Asn Arg Ala Leu Thr Gly Ile Ala Val
                820                 825                 830

Glu Gln Asp Lys Asn Thr Gln Glu Val Phe Ala Gln Val Lys Gln Ile
                835                 840                 845

Tyr Lys Thr Pro Pro Ile Lys Asp Phe Gly Gly Phe Asn Phe Ser Gln
                850                 855                 860

Ile Leu Pro Asp Pro Ser Lys Pro Ser Lys Arg Ser Phe Ile Glu Asp
865                 870                 875                 880

Leu Leu Phe Asn Lys Val Thr Leu Ala Asp Ala Gly Phe Ile Lys Gln
                885                 890                 895

Tyr Gly Asp Cys Leu Gly Asp Ile Ala Ala Arg Asp Leu Ile Cys Ala
                900                 905                 910

Gln Lys Phe Asn Gly Leu Thr Val Leu Pro Pro Leu Leu Thr Asp Glu
                915                 920                 925

Met Ile Ala Gln Tyr Thr Ser Ala Leu Leu Ala Gly Thr Ile Thr Ser
930                 935                 940

Gly Trp Thr Phe Gly Ala Gly Ala Ala Leu Gln Ile Pro Phe Ala Met
945                 950                 955                 960

Gln Met Ala Tyr Arg Phe Asn Gly Ile Gly Val Thr Gln Asn Val Leu
                965                 970                 975

Tyr Glu Asn Gln Lys Leu Ile Ala Asn Gln Phe Asn Ser Ala Ile Gly
                980                 985                 990

Lys Ile Gln Asp Ser Leu Ser Ser  Thr Ala Ser Ala Leu  Gly Lys Leu
                995                 1000                1005

Gln Asp Val Val Asn Gln Asn  Ala Gln Ala Leu Asn  Thr Leu Val
        1010                1015                1020

Lys Gln Leu Ser Ser Asn Phe  Gly Ala Ile Ser Ser  Val Leu Asn
        1025                1030                1035

Asp Ile Leu Ser Arg Leu Asp  Lys Val Glu Ala Glu  Val Gln Ile
        1040                1045                1050
```

-continued

```
Asp Arg Leu Ile Thr Gly Arg Leu Gln Ser Leu Gln Thr Tyr Val
    1055                1060                1065

Thr Gln Gln Leu Ile Arg Ala Ala Glu Ile Arg Ala Ser Ala Asn
    1070                1075                1080

Leu Ala Ala Thr Lys Met Ser Glu Cys Val Leu Gly Gln Ser Lys
    1085                1090                1095

Arg Val Asp Phe Cys Gly Lys Gly Tyr His Leu Met Ser Phe Pro
    1100                1105                1110

Gln Ser Ala Pro His Gly Val Val Phe Leu His Val Thr Tyr Val
    1115                1120                1125

Pro Ala Gln Glu Lys Asn Phe Thr Thr Ala Pro Ala Ile Cys His
    1130                1135                1140

Asp Gly Lys Ala His Phe Pro Arg Glu Gly Val Phe Val Ser Asn
    1145                1150                1155

Gly Thr His Trp Phe Val Thr Gln Arg Asn Phe Tyr Glu Pro Gln
    1160                1165                1170

Ile Ile Thr Thr Asp Asn Thr Phe Val Ser Gly Asn Cys Asp Val
    1175                1180                1185

Val Ile Gly Ile Val Asn Asn Thr Val Tyr Asp Pro Leu Gln Pro
    1190                1195                1200

Glu Leu Asp Ser Phe Lys Glu Glu Leu Asp Lys Tyr Phe Lys Asn
    1205                1210                1215

His Thr Ser Pro Asp Val Asp Leu Gly Asp Ile Ser Gly Ile Asn
    1220                1225                1230

Ala Ser Val Val Asn Ile Gln Lys Glu Ile Asp Arg Leu Asn Glu
    1235                1240                1245

Val Ala Lys Asn Leu Asn Glu Ser Leu Ile Asp Leu Gln Glu Leu
    1250                1255                1260

Gly Lys Tyr Glu Gln Tyr Ile Lys Trp Pro Trp Tyr Ile Trp Leu
    1265                1270                1275

Gly Phe Ile Ala Gly Leu Ile Ala Ile Val Met Val Thr Ile Met
    1280                1285                1290

Leu Cys Cys Met Thr Ser Cys Cys Ser Cys Leu Lys Gly Cys Cys
    1295                1300                1305

Ser Cys Gly Ser Cys Cys Lys Phe Asp Glu Asp Ser Glu Pro
    1310                1315                1320

Val Leu Lys Gly Val Lys Leu His Tyr Thr Tyr Thr Asp Ile Glu
    1325                1330                1335

Met Asn Arg Leu Gly Lys
    1340

<210> SEQ ID NO 31
<211> LENGTH: 1355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
                20                  25                  30

Gly Leu Leu Ala Ile Ala Gly Ile Arg Leu His Arg Ala Ala Ile Tyr
            35                  40                  45
```

```
Thr Ala Glu Ile His Lys Ser Leu Ser Thr Asn Leu Asp Val Thr Asn
     50                  55                  60

Ser Ile Glu His Gln Val Lys Asp Val Leu Thr Pro Leu Phe Lys Ile
 65                  70                  75                  80

Ile Gly Asp Glu Val Gly Leu Arg Thr Pro Gln Arg Phe Thr Asp Leu
                 85                  90                  95

Val Lys Phe Ile Ser Asp Lys Ile Lys Phe Leu Asn Pro Asp Arg Glu
                100                 105                 110

Tyr Asp Phe Arg Asp Leu Thr Trp Cys Ile Asn Pro Glu Arg Ile
                115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
                180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
                340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
    370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415

Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Ala Leu
    450                 455                 460
```

```
Phe Asn Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
                500                 505                 510

Thr Ser Ala Val Glu His Ala Val Val Tyr Val Tyr Ser Pro Ser
            515                 520                 525

Arg Ser Phe Ser Tyr Phe Tyr Pro Phe Arg Leu Pro Ile Lys Gly Val
        530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
                580                 585                 590

Glu Gly Gly Gly Ser Lys Gly Thr Asp Asp Ala Thr Ala Asp Ser Arg
        595                 600                 605

Lys Thr Tyr Thr Leu Thr Asp Tyr Leu Lys Asn Thr Tyr Arg Leu Lys
        610                 615                 620

Leu Tyr Ser Leu Arg Trp Ile Ser Asp His Glu Tyr Leu Tyr Lys Gln
625                 630                 635                 640

Glu Asn Asn Ile Leu Val Phe Asn Ala Glu Tyr Gly Asn Ser Ser Val
                645                 650                 655

Phe Leu Glu Asn Ser Thr Phe Asp Glu Phe Gly His Ser Ile Asn Asp
                660                 665                 670

Tyr Ser Ile Ser Pro Asp Gly Gln Phe Ile Leu Leu Glu Tyr Asn Tyr
            675                 680                 685

Val Lys Gln Trp Arg His Ser Tyr Thr Ala Ser Tyr Asp Ile Tyr Asp
            690                 695                 700

Leu Asn Lys Arg Gln Leu Ile Thr Glu Glu Arg Ile Pro Asn Asn Thr
705                 710                 715                 720

Gln Trp Val Thr Trp Ser Pro Val Gly His Lys Leu Ala Tyr Val Trp
                725                 730                 735

Asn Asn Asp Ile Tyr Val Lys Ile Glu Pro Asn Leu Pro Ser Tyr Arg
                740                 745                 750

Ile Thr Trp Thr Gly Lys Glu Asp Ile Ile Tyr Asn Gly Ile Thr Asp
            755                 760                 765

Trp Val Tyr Glu Glu Glu Val Phe Ser Ala Tyr Ser Ala Leu Trp Trp
            770                 775                 780

Ser Pro Asn Gly Thr Phe Leu Ala Tyr Ala Gln Phe Asn Asp Thr Glu
785                 790                 795                 800

Val Pro Leu Ile Glu Tyr Ser Phe Tyr Ser Asp Glu Ser Leu Gln Tyr
                805                 810                 815

Pro Lys Thr Val Arg Val Pro Tyr Pro Lys Ala Gly Ala Val Asn Pro
            820                 825                 830

Thr Val Lys Phe Phe Val Val Asn Thr Asp Ser Leu Ser Ser Val Thr
            835                 840                 845

Asn Ala Thr Ser Ile Gln Ile Thr Ala Pro Ala Ser Met Leu Ile Gly
            850                 855                 860

Asp His Tyr Leu Cys Asp Val Thr Trp Ala Thr Gln Glu Arg Ile Ser
865                 870                 875                 880

Leu Gln Trp Leu Arg Arg Ile Gln Asn Tyr Ser Val Met Asp Ile Cys
```

-continued

```
                885                 890                 895
Asp Tyr Asp Glu Ser Ser Gly Arg Trp Asn Cys Leu Val Ala Arg Gln
            900                 905                 910
His Ile Glu Met Ser Thr Thr Gly Trp Val Gly Arg Phe Arg Pro Ser
            915                 920                 925
Glu Pro His Phe Thr Leu Asp Gly Asn Ser Phe Tyr Lys Ile Ile Ser
    930                 935                 940
Asn Glu Glu Gly Tyr Arg His Ile Cys Tyr Phe Gln Ile Asp Lys Lys
945                 950                 955                 960
Asp Cys Thr Phe Ile Thr Lys Gly Thr Trp Glu Val Ile Gly Ile Glu
            965                 970                 975
Ala Leu Thr Ser Asp Tyr Leu Tyr Tyr Ile Ser Asn Glu Tyr Lys Gly
            980                 985                 990
Met Pro Gly Gly Arg Asn Leu Tyr  Lys Ile Gln Leu Ser  Asp Tyr Thr
            995                 1000                1005
Lys Val  Thr Cys Leu Ser Cys  Glu Leu Asn Pro Glu  Arg Cys Gln
    1010                1015                1020
Tyr Tyr  Ser Val Ser Phe Ser  Lys Glu Ala Lys Tyr  Tyr Gln Leu
    1025                1030                1035
Arg Cys  Ser Gly Pro Gly Leu  Pro Leu Tyr Thr Leu  His Ser Ser
    1040                1045                1050
Val Asn  Asp Lys Gly Leu Arg  Val Leu Glu Asp Asn  Ser Ala Leu
    1055                1060                1065
Asp Lys  Met Leu Gln Asn Val  Gln Met Pro Ser Lys  Lys Leu Asp
    1070                1075                1080
Phe Ile  Ile Leu Asn Glu Thr  Lys Phe Trp Tyr Gln  Met Ile Leu
    1085                1090                1095
Pro Pro  His Phe Asp Lys Ser  Lys Lys Tyr Pro Leu  Leu Leu Asp
    1100                1105                1110
Val Tyr  Ala Gly Pro Cys Ser  Gln Lys Ala Asp Thr  Val Phe Arg
    1115                1120                1125
Leu Asn  Trp Ala Thr Tyr Leu  Ala Ser Thr Glu Asn  Ile Ile Val
    1130                1135                1140
Ala Ser  Phe Asp Gly Arg Gly  Ser Gly Tyr Gln Gly  Asp Lys Ile
    1145                1150                1155
Met His  Ala Ile Asn Arg Arg  Leu Gly Thr Phe Glu  Val Glu Asp
    1160                1165                1170
Gln Ile  Glu Ala Ala Arg Gln  Phe Ser Lys Met Gly  Phe Val Asp
    1175                1180                1185
Asn Lys  Arg Ile Ala Ile Trp  Gly Trp Ser Tyr Gly  Gly Tyr Val
    1190                1195                1200
Thr Ser  Met Val Leu Gly Ser  Gly Ser Gly Val Phe  Lys Cys Gly
    1205                1210                1215
Ile Ala  Val Ala Pro Val Ser  Arg Trp Glu Tyr Tyr  Asp Ser Val
    1220                1225                1230
Tyr Thr  Glu Arg Tyr Met Gly  Leu Pro Thr Pro Glu  Asp Asn Leu
    1235                1240                1245
Asp His  Tyr Arg Asn Ser Thr  Val Met Ser Arg Ala  Glu Asn Phe
    1250                1255                1260
Lys Gln  Val Glu Tyr Leu Leu  Ile His Gly Thr Ala  Asp Asp Asn
    1265                1270                1275
Val His  Phe Gln Gln Ser Ala  Gln Ile Ser Lys Ala  Leu Val Asp
    1280                1285                1290
```

Val Gly Val Asp Phe Gln Ala Met Trp Tyr Thr Asp Glu Asp His
    1295                1300                1305

Gly Ile Ala Ser Ser Thr Ala His Gln His Ile Tyr Thr His Met
    1310                1315                1320

Ser His Phe Ile Lys Gln Cys Phe Ser Leu Pro Ala Ala Ala Arg
    1325                1330                1335

Gly Ser Gly Leu Asn Asp Ile Phe Glu Ala Gln Lys Ile Glu Trp
    1340                1345                1350

His Glu
    1355

<210> SEQ ID NO 32
<211> LENGTH: 737
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Gly Thr Asp Asp Ala Thr Ala Asp Ser Arg Lys Thr Tyr Thr Leu
1               5                   10                  15

Thr Asp Tyr Leu Lys Asn Thr Tyr Arg Leu Lys Leu Tyr Ser Leu Arg
            20                  25                  30

Trp Ile Ser Asp His Glu Tyr Leu Tyr Lys Gln Glu Asn Asn Ile Leu
        35                  40                  45

Val Phe Asn Ala Glu Tyr Gly Asn Ser Ser Val Phe Leu Glu Asn Ser
50                  55                  60

Thr Phe Asp Glu Phe Gly His Ser Ile Asn Asp Tyr Ser Ile Ser Pro
65                  70                  75                  80

Asp Gly Gln Phe Ile Leu Leu Glu Tyr Asn Tyr Val Lys Gln Trp Arg
                85                  90                  95

His Ser Tyr Thr Ala Ser Tyr Asp Ile Tyr Asp Leu Asn Lys Arg Gln
            100                 105                 110

Leu Ile Thr Glu Glu Arg Ile Pro Asn Asn Thr Gln Trp Val Thr Trp
        115                 120                 125

Ser Pro Val Gly His Lys Leu Ala Tyr Val Trp Asn Asn Asp Ile Tyr
    130                 135                 140

Val Lys Ile Glu Pro Asn Leu Pro Ser Tyr Arg Ile Thr Trp Thr Gly
145                 150                 155                 160

Lys Glu Asp Ile Ile Tyr Asn Gly Ile Thr Asp Trp Val Tyr Glu Glu
                165                 170                 175

Glu Val Phe Ser Ala Tyr Ser Ala Leu Trp Trp Ser Pro Asn Gly Thr
            180                 185                 190

Phe Leu Ala Tyr Ala Gln Phe Asn Asp Thr Glu Val Pro Leu Ile Glu
        195                 200                 205

Tyr Ser Phe Tyr Ser Asp Glu Ser Leu Gln Tyr Pro Lys Thr Val Arg
    210                 215                 220

Val Pro Tyr Pro Lys Ala Gly Ala Val Asn Pro Thr Val Lys Phe Phe
225                 230                 235                 240

Val Val Asn Thr Asp Ser Leu Ser Ser Val Thr Asn Ala Thr Ser Ile
                245                 250                 255

Gln Ile Thr Ala Pro Ala Ser Met Leu Ile Gly Asp His Tyr Leu Cys
            260                 265                 270

Asp Val Thr Trp Ala Thr Gln Glu Arg Ile Ser Leu Gln Trp Leu Arg

-continued

```
                275                 280                 285
Arg Ile Gln Asn Tyr Ser Val Met Asp Ile Cys Asp Tyr Asp Glu Ser
290                 295                 300

Ser Gly Arg Trp Asn Cys Leu Val Ala Arg Gln His Ile Glu Met Ser
305                 310                 315                 320

Thr Thr Gly Trp Val Gly Arg Phe Arg Pro Ser Glu Pro His Phe Thr
                325                 330                 335

Leu Asp Gly Asn Ser Phe Tyr Lys Ile Ile Ser Asn Glu Glu Gly Tyr
                340                 345                 350

Arg His Ile Cys Tyr Phe Gln Ile Asp Lys Lys Asp Cys Thr Phe Ile
                355                 360                 365

Thr Lys Gly Thr Trp Glu Val Ile Gly Ile Glu Ala Leu Thr Ser Asp
370                 375                 380

Tyr Leu Tyr Tyr Ile Ser Asn Glu Tyr Lys Gly Met Pro Gly Gly Arg
385                 390                 395                 400

Asn Leu Tyr Lys Ile Gln Leu Ser Asp Tyr Thr Lys Val Thr Cys Leu
                405                 410                 415

Ser Cys Glu Leu Asn Pro Glu Arg Cys Gln Tyr Tyr Ser Val Ser Phe
                420                 425                 430

Ser Lys Glu Ala Lys Tyr Tyr Gln Leu Arg Cys Ser Gly Pro Gly Leu
                435                 440                 445

Pro Leu Tyr Thr Leu His Ser Ser Val Asn Asp Lys Gly Leu Arg Val
450                 455                 460

Leu Glu Asp Asn Ser Ala Leu Asp Lys Met Leu Gln Asn Val Gln Met
465                 470                 475                 480

Pro Ser Lys Lys Leu Asp Phe Ile Ile Leu Asn Glu Thr Lys Phe Trp
                485                 490                 495

Tyr Gln Met Ile Leu Pro Pro His Phe Asp Lys Ser Lys Lys Tyr Pro
                500                 505                 510

Leu Leu Leu Asp Val Tyr Ala Gly Pro Cys Ser Gln Lys Ala Asp Thr
                515                 520                 525

Val Phe Arg Leu Asn Trp Ala Thr Tyr Leu Ala Ser Thr Glu Asn Ile
530                 535                 540

Ile Val Ala Ser Phe Asp Gly Arg Gly Ser Gly Tyr Gln Gly Asp Lys
545                 550                 555                 560

Ile Met His Ala Ile Asn Arg Arg Leu Gly Thr Phe Glu Val Glu Asp
                565                 570                 575

Gln Ile Glu Ala Ala Arg Gln Phe Ser Lys Met Gly Phe Val Asp Asn
                580                 585                 590

Lys Arg Ile Ala Ile Trp Gly Trp Ser Tyr Gly Gly Tyr Val Thr Ser
                595                 600                 605

Met Val Leu Gly Ser Gly Ser Gly Val Phe Lys Cys Gly Ile Ala Val
610                 615                 620

Ala Pro Val Ser Arg Trp Glu Tyr Tyr Asp Ser Val Tyr Thr Glu Arg
625                 630                 635                 640

Tyr Met Gly Leu Pro Thr Pro Glu Asp Asn Leu Asp His Tyr Arg Asn
                645                 650                 655

Ser Thr Val Met Ser Arg Ala Glu Asn Phe Lys Gln Val Glu Tyr Leu
                660                 665                 670

Leu Ile His Gly Thr Ala Asp Asp Asn Val His Phe Gln Gln Ser Ala
                675                 680                 685

Gln Ile Ser Lys Ala Leu Val Asp Val Gly Val Asp Phe Gln Ala Met
                690                 695                 700
```

```
Trp Tyr Thr Asp Glu Asp His Gly Ile Ala Ser Ser Thr Ala His Gln
705                 710                 715                 720

His Ile Tyr Thr His Met Ser His Phe Ile Lys Gln Cys Phe Ser Leu
                725                 730                 735

Pro

<210> SEQ ID NO 33
<211> LENGTH: 848
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320
```

```
Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His Ala Glu Met Gly Ala Ile Gln Tyr Asp Met Ala
            370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
            565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
            610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735
```

```
Pro Pro Val Ser Ser Arg Gly Met Leu Asp Ser Asp Leu His Leu Ser
            740                 745                 750

Ser Lys Ala Gln Val Phe Glu His Pro His Ile Gln Asp Ala Ala Ser
        755                 760                 765

Gln Leu Pro Asp Asp Glu Ser Leu Phe Phe Gly Asp Thr Gly Leu Ser
    770                 775                 780

Lys Asn Pro Ile Glu Leu Val Glu Gly Trp Phe Ser Ser Trp Lys Ser
785                 790                 795                 800

Ser Ile Ala Ser Phe Phe Phe Ile Ile Gly Leu Ile Ile Gly Leu Phe
                805                 810                 815

Leu Val Leu Arg Val Gly Ile His Leu Cys Ile Lys Leu Lys His Thr
            820                 825                 830

Lys Lys Arg Gln Ile Tyr Thr Asp Ile Glu Met Asn Arg Leu Gly Lys
        835                 840                 845

<210> SEQ ID NO 34
<211> LENGTH: 978
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ser Ser Ser Trp Leu Leu Leu Ser Leu Val Ala Val Thr Ala Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255
```

-continued

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

```
Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
            725                 730                 735

Pro Pro Val Ser Ser Arg Ile Gln Ala Asp Gly Trp Met Cys His Ala
            740                 745                 750

Ser Lys Trp Val Thr Thr Cys Asp Phe Arg Trp Tyr Gly Pro Lys Tyr
            755                 760                 765

Ile Thr His Ser Ile Arg Ser Phe Thr Pro Ser Val Glu Gln Cys Lys
            770                 775                 780

Glu Ser Ile Glu Gln Thr Lys Gln Gly Thr Trp Leu Asn Pro Gly Phe
785                 790                 795                 800

Pro Pro Gln Ser Cys Gly Tyr Ala Thr Val Thr Asp Ala Glu Ala Val
            805                 810                 815

Ile Val Gln Val Thr Pro His His Val Leu Val Asp Glu Tyr Thr Gly
            820                 825                 830

Glu Trp Val Asp Ser Gln Phe Ile Asn Gly Lys Cys Ser Asn Tyr Ile
            835                 840                 845

Cys Pro Thr Val His Asn Ser Thr Thr Trp His Ser Asp Tyr Lys Val
            850                 855                 860

Lys Gly Leu Cys Asp Ser Asn Leu Gly Met Leu Asp Ser Asp Leu His
865                 870                 875                 880

Leu Ser Ser Lys Ala Gln Val Phe Glu His Pro His Ile Gln Asp Ala
            885                 890                 895

Ala Ser Gln Leu Pro Asp Asp Glu Ser Leu Phe Phe Gly Asp Thr Gly
            900                 905                 910

Leu Ser Lys Asn Pro Ile Glu Leu Val Glu Gly Trp Phe Ser Ser Trp
            915                 920                 925

Lys Ser Ser Ile Ala Ser Phe Phe Phe Ile Ile Gly Leu Ile Ile Gly
            930                 935                 940

Leu Phe Leu Val Leu Arg Val Gly Ile His Leu Cys Ile Lys Leu Lys
945                 950                 955                 960

His Thr Lys Lys Arg Gln Ile Tyr Thr Asp Ile Glu Met Asn Arg Leu
            965                 970                 975

Gly Lys

<210> SEQ ID NO 35
<211> LENGTH: 978
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45
```

-continued

```
Asn Tyr Asn Thr Asn Ile Thr Glu Glu Asn Val Gln Asn Met Asn Asn
 50                  55                  60
Ala Gly Asp Lys Trp Ser Ala Phe Leu Lys Glu Gln Ser Thr Leu Ala
 65                  70                  75                  80
Gln Met Tyr Pro Leu Gln Glu Ile Gln Asn Leu Thr Val Lys Leu Gln
                 85                  90                  95
Leu Gln Ala Leu Gln Gln Asn Gly Ser Ser Val Leu Ser Glu Asp Lys
            100                 105                 110
Ser Lys Arg Leu Asn Thr Ile Leu Asn Thr Met Ser Thr Ile Tyr Ser
        115                 120                 125
Thr Gly Lys Val Cys Asn Pro Asp Asn Pro Gln Glu Cys Leu Leu Leu
    130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
        195                 200                 205
Val Asn Gly Val Asp Gly Tyr Asp Tyr Ser Arg Gly Gln Leu Ile Glu
    210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
        275                 280                 285
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His Ala Glu Met Gly Ala Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
```

```
              465                 470                 475                 480
Lys Arg Glu Ile Val Gly Val Glu Pro Val Pro His Asp Glu Thr
                    485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
        610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ser Arg Ile Gln Ala Asp Gly Trp Met Cys His Ala
                740                 745                 750

Ser Lys Trp Val Thr Thr Cys Asp Phe Arg Trp Tyr Gly Pro Lys Tyr
            755                 760                 765

Ile Thr His Ser Ile Arg Ser Phe Thr Pro Ser Val Glu Gln Cys Lys
        770                 775                 780

Glu Ser Ile Glu Gln Thr Lys Gln Gly Thr Trp Leu Asn Pro Gly Phe
785                 790                 795                 800

Pro Pro Gln Ser Cys Gly Tyr Ala Thr Val Thr Asp Ala Glu Ala Val
                805                 810                 815

Ile Val Gln Val Thr Pro His His Val Leu Val Asp Glu Tyr Thr Gly
                820                 825                 830

Glu Trp Val Asp Ser Gln Phe Ile Asn Gly Lys Cys Ser Asn Tyr Ile
            835                 840                 845

Cys Pro Thr Val His Asn Ser Thr Thr Trp His Ser Asp Tyr Lys Val
        850                 855                 860

Lys Gly Leu Cys Asp Ser Asn Leu Gly Met Leu Asp Ser Asp Leu His
865                 870                 875                 880

Leu Ser Ser Lys Ala Gln Val Phe Glu His Pro His Ile Gln Asp Ala
                885                 890                 895
```

```
Ala Ser Gln Leu Pro Asp Asp Glu Ser Leu Phe Phe Gly Asp Thr Gly
            900             905                 910

Leu Ser Lys Asn Pro Ile Glu Leu Val Glu Gly Trp Phe Ser Ser Trp
        915             920             925

Lys Ser Ser Ile Ala Ser Phe Phe Phe Ile Ile Gly Leu Ile Ile Gly
        930             935             940

Leu Phe Leu Val Leu Arg Val Gly Ile His Leu Cys Ile Lys Leu Lys
945             950             955             960

His Thr Lys Lys Arg Gln Ile Tyr Thr Asp Ile Glu Met Asn Arg Leu
            965             970             975

Gly Lys
```